(12) United States Patent
Booth

(10) Patent No.: US 12,234,217 B2
(45) Date of Patent: Feb. 25, 2025

(54) METHOD FOR PREPARING N-PHENYLPYRAZOLE-1-CARBOXAMIDES

(71) Applicants: FMC CORPORATION, Philadelphia, PA (US); FMC AGRO SINGAPORE PTE. LTD., Singapore (SG)

(72) Inventor: Steven T. Booth, Wilmington, DE (US)

(73) Assignees: FMC CORPORATION, Philadelphia, PA (US); FMC AGRO SINGAPORE PTE. LTD., Singapore (SG)

( * ) Notice: Subject to any disclaimer, the term of this patent is extended or adjusted under 35 U.S.C. 154(b) by 763 days.

(21) Appl. No.: 17/299,391

(22) PCT Filed: Nov. 22, 2019

(86) PCT No.: PCT/US2019/062778
§ 371 (c)(1),
(2) Date: Jun. 3, 2021

(87) PCT Pub. No.: WO2020/117493
PCT Pub. Date: Jun. 11, 2020

(65) Prior Publication Data
US 2022/0056007 A1 Feb. 24, 2022

Related U.S. Application Data

(60) Provisional application No. 62/774,436, filed on Dec. 3, 2018.

(51) Int. Cl.
C07D 401/04 (2006.01)
(52) U.S. Cl.
CPC .................. C07D 401/04 (2013.01)
(58) Field of Classification Search
CPC .................................. C07D 401/04
USPC .................................... 546/275.4
See application file for complete search history.

(56) References Cited

U.S. PATENT DOCUMENTS

| | | | | |
|---|---|---|---|---|
| 7,528,260 B2 * | 5/2009 | Shapiro | ................. | C07C 255/58 562/622 |
| 8,034,968 B2 * | 10/2011 | Annis | ................. | C07D 231/14 558/415 |
| 8,217,179 B2 * | 7/2012 | Li | ................. | C07D 401/04 546/275.4 |
| 8,242,279 B2 * | 8/2012 | Dumas | ................. | C07D 231/16 546/275.4 |
| 8,247,570 B2 * | 8/2012 | Dumas | ................. | C07D 231/16 546/276.1 |
| 8,748,630 B2 * | 6/2014 | Bruening | ............. | C07D 231/14 548/374.1 |
| 9,162,973 B2 * | 10/2015 | Kristjansdottir | ...... | C07C 231/10 |
| 9,301,529 B2 * | 4/2016 | Wang | ................. | C07D 413/14 |
| 9,332,756 B2 * | 5/2016 | Gutsche | ................. | A01N 63/40 |
| 2010/0137374 A1 * | 6/2010 | Annan | ................. | A01N 25/14 514/616 |
| 2023/0286939 A1 * | 9/2023 | Søndergaard | ........ | C07D 401/04 |

FOREIGN PATENT DOCUMENTS

| | | | |
|---|---|---|---|
| CN | 103130770 | * | 6/2013 |
| CN | 103601718 | * | 2/2014 |
| WO | 2003/015518 | | 2/2003 |
| WO | 2003/016283 | | 2/2003 |
| WO | 2004/011453 | | 2/2004 |
| WO | 2005/077934 | | 8/2005 |
| WO | 2006/062978 | | 6/2006 |
| WO | 2007/144100 | | 12/2007 |
| WO | 2008/072745 | | 6/2008 |
| WO | 2010/069502 | | 6/2010 |
| WO | 2015/162260 | | 10/2015 |

OTHER PUBLICATIONS

International Search Report of corresponding PCT/US2019/062778 application mailed Jun. 11, 2020.

* cited by examiner

*Primary Examiner* — Niloofar Rahmani

(57) ABSTRACT

A method is disclosed for preparing compounds of Formula 1 by combining compounds of Formulae 2 and 3 and a sulfonyl chloride in a continuous process.

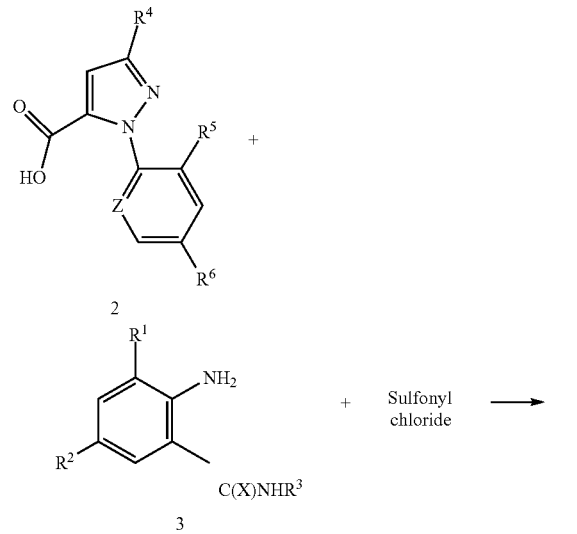

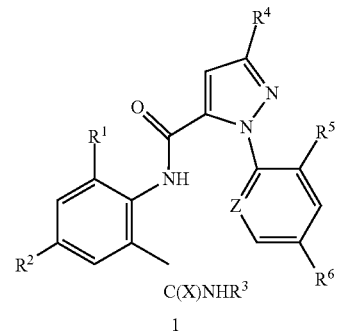

19 Claims, 8 Drawing Sheets

METHOD FOR PREPARING N-PHENYLPYRAZOLE-1-CARBOXAMIDES

FIELD OF THE INVENTION

This present disclosure relates to a method for preparing N-phenylpyrazole-1-carboxamides or N-pyridinylpyrazole-1-carboxamides by coupling carboxylic acids with anthranilamides in a continuous process.

BACKGROUND OF THE INVENTION

PCT Patent Publication WO 2003/015518 discloses the utility of N-acyl anthranilic acid derivatives of Formula i as arthropodicides

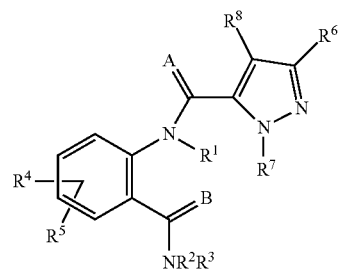

wherein A and B are independently O or S; $R^1$ is H; $R^2$ is H, $C_1$-$C_6$ alkyl, $C_2$-$C_6$ alkoxycarbonyl or $C_2$-$C_6$ alkylcarbonyl; $R^3$ is, inter alia, H or $C_1$-$C_6$ alkyl; $R^4$ is, inter alia, H or $C_1$-$C_6$ alkyl; $R^5$ is H, $C_1$-$C_6$ alkyl or halogen; $R^6$ is H, $C_1$-$C_6$ alkyl, $C_1$-$C_6$ haloalkyl, halogen, CN, $C_1$-$C_4$ alkoxy or $C_1$-$C_4$ haloalkoxy; $R^7$ is, inter alia, a phenyl ring, a benzyl ring, a 5- or 6-membered heteroaromatic ring, a napthyl ring system, each ring or ring system optionally substituted with 1-3 substituents; and $R^8$ is, inter alia, H.

WO 2006/062978 discloses a method for preparing N-phenylpyrazole-1-carboxamides or N-pyridinylpyrazole-1-carboxamides by coupling carboxylic acids with anthranilamides. See also WO 2003/016283, WO 2004/011453, WO 2005/077934, WO 2007/144100, WO 2008/072745 and WO 2010/069502.

While the methods disclosed in the preceding references can provide the desired compounds, continuous improvements are sought, particularly in the development of methods to provide materials on a commercial scale. Therefore, the need continues for new methods that are less costly, more efficient, more flexible, or more convenient to operate.

SUMMARY OF THE INVENTION

This disclosure is directed to a process for preparing compounds of Formula 1 (including all stereoisomers and N-oxides of such compounds, and salts of such compounds):

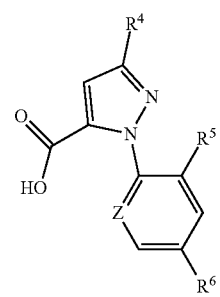

wherein
X is O or S;
Z is $CR^7$ or N;
$R^1$ is H, $CH_3$, Cl or Br;
$R^2$ is H, Br, Cl or CN;
$R^3$ is H, $C_1$-$C_4$ alkyl or $C_4$-$C_{10}$ cycloalkylalkyl;
$R^4$ is Cl, Br, $OCF_2H$, $OCH_2CF_3$; or $C_1$-$C_4$ alkyl optionally substituted with halogen; or $C_1$-$C_4$ alkyl substituted with Q;
$R^5$ is F, Cl or Br;
$R^6$ is H, F or $C_1$;
$R^7$ is H, F, Cl or Br, and
Q is a 5- or 6-membered aromatic heterocyclic ring optionally substituted with one or more substituents independently selected from the group consisting of halogen, $C_1$-$C_6$ alkyl, $C_3$-$C_6$ cycloalkyl and $C_1$-$C_6$ haloalkyl;

including:
combining (1) a carboxylic acid compound of Formula 2,

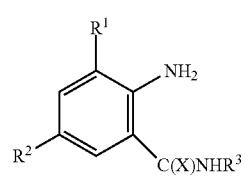

wherein Z, $R^4$, $R^1$, $R^6$, $R^7$, and Q are as defined for the compound of Formula 1
(2) an aniline compound of Formula 3,

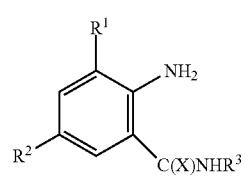

wherein X, $R^1$, $R^2$ and $R^3$ are as defined for the compound of Formula 1; and (3) a sulfonyl chloride to form the compound of Formula 1; wherein the method includes a continuous process.

DETAILED DESCRIPTION OF THE INVENTION

Figure 1:
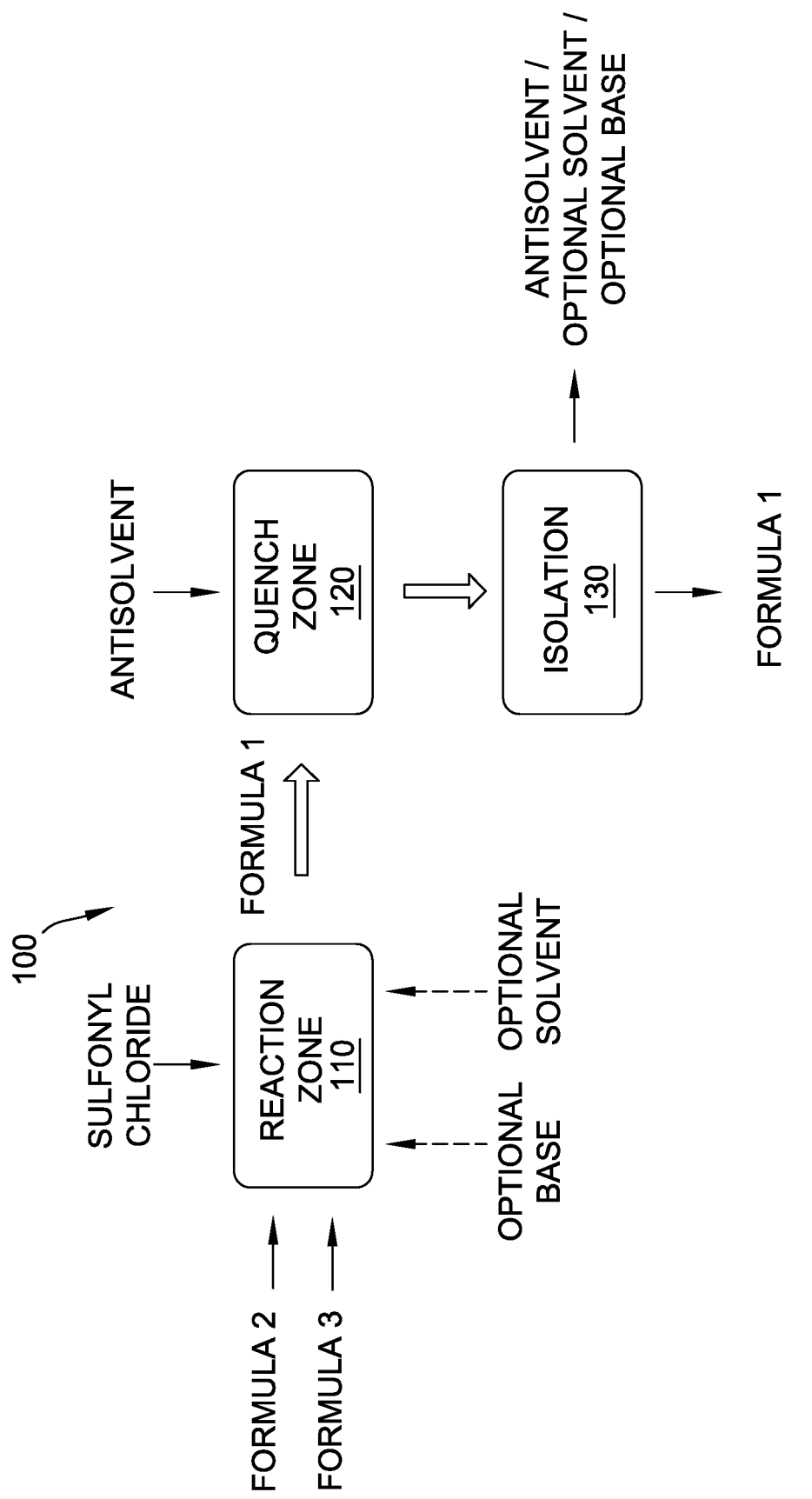
FIG. 1 shows a flow diagram illustrating a continuous process for preparing a compound of Formula 1 including continuously charging a compound of Formula 2, a compound of Formula 3, sulfonyl chloride, an optional base and an optional solvent into a reaction zone; transferring the resultant mixture including a compound of Formula 1 to a quench zone wherein an antisolvent is introduced; and transferring the quenched mixture including a compound of Formula 1 to an isolation zone wherein the antisolvent, the optional solvent and the optional base are removed.

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Combining chemicals refers to contacting the chemicals with each other.

"Carbon-based radical" refers to a monovalent molecular component including a carbon atom that connects the radical to the remainder of the chemical structure through a single bond. Carbon-based radicals can optionally include saturated, unsaturated and aromatic groups, chains, rings and ring systems, and heteroatoms. Although carbon-based radicals are not subject to any specific limit in size, in the context of the present disclosure they typically include 1 to 16 carbon atoms and 0 to 3 heteroatoms. Of note are carbon-based radicals selected from $C_1$-$C_6$ alkyl, $C_1$-$C_4$ haloalkyl and phenyl optionally substituted with 1-3 substituents selected from $C_1$-$C_3$ alkyl, halogen and nitro.

In the recitations herein, the abbreviation "Ph" means phenyl. Alkyl can be straight chain or branched. "Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopropylethyl, cyclopentylethyl, and other cycloalkyl moieties bonded to straight-chain or branched alkyl groups. The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $BrCH_2$, $CF_3CH_2$ and $CF_3CCl_2$.

As noted above, Q is a 5- or 6-membered aromatic heterocyclic ring, optionally substituted with one or more substituents selected from a group of substituents as defined in the Summary of the Invention. When Q is a 5- or 6-membered nitrogen-containing heterocyclic ring, it may be attached to the remainder of Formula 1 though any available carbon or nitrogen ring atom, unless otherwise described. Examples of a 5- or 6-membered aromatic heterocyclic ring optionally substituted with from one or more substituents include the rings U-2 through U-63 illustrated in Exhibit 1 wherein $R^v$ is any substituent as defined in the Summary of the Invention for Q and r is an integer from 0 to 4, limited by the number of available positions on each U group. As U-29, U-30, U-36, U-37, U-38, U-39, U-40, U-41, U-42, U-43, U-49 and U-50 have only one available position, for these U groups r is limited to the integers 0 or 1, and r being 0 means that the U group is unsubstituted and a hydrogen is present at the position indicated by $(R^v)_r$.
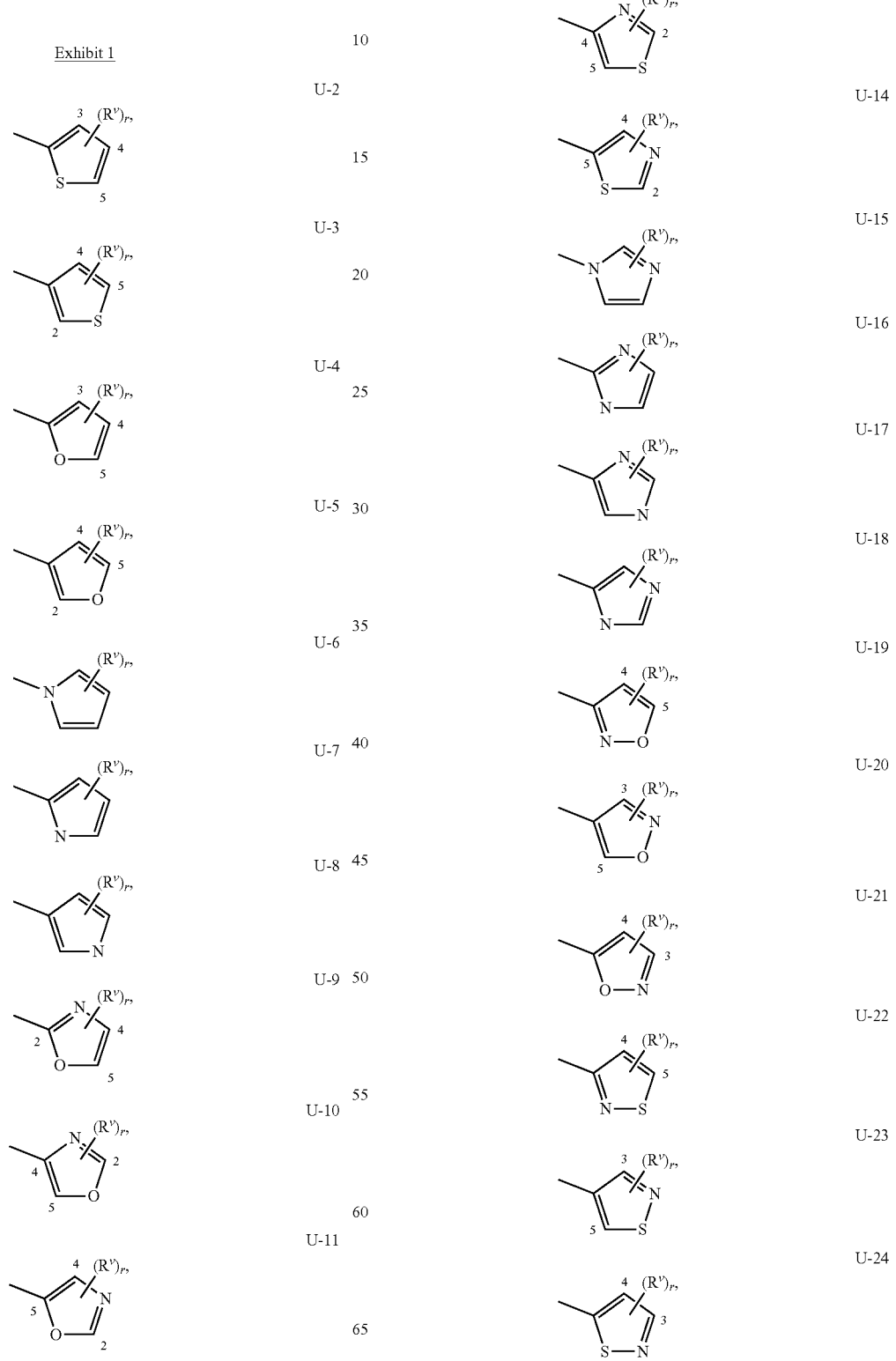

| | |
|---|---|
| U-25 | 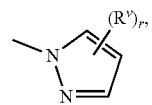 |
| U-26 | 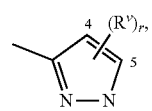 |
| U-27 | 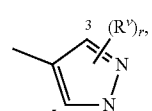 |
| U-28 | 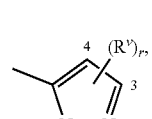 |
| U-29 | 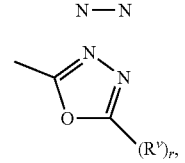 |
| U-30 | 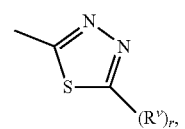 |
| U-31 | 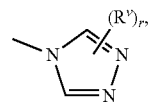 |
| U-32 | 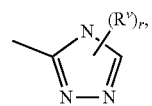 |
| U-33 | 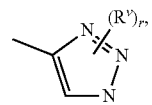 |
| U-34 | 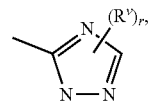 |
| U-35 | 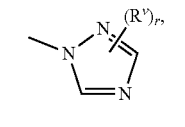 |
| U-36 | 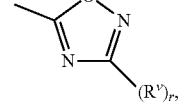 |
| U-37 | 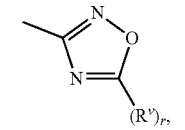 |
| | |
|---|---|
| U-38 | 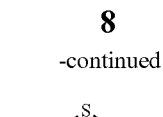 |
| U-39 | 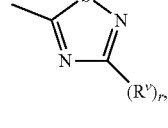 |
| U-40 | 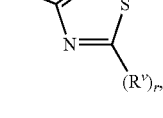 |
| U-41 | 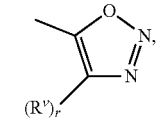 |
| U-42 | 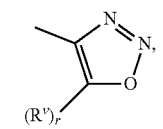 |
| U-43 | 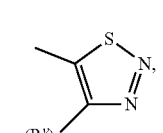 |
| U-44 | 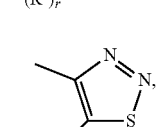 |
| U-45 | 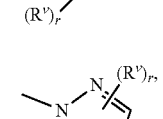 |
| U-46 | 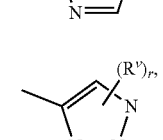 |
| U-47 | 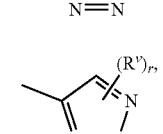 |
| U-48 | 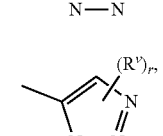 |
| U-49 | 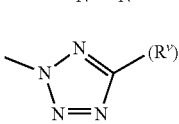 |

-continued

U-50 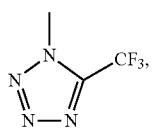

U-51 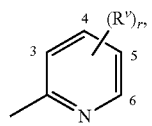

U-52 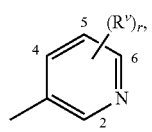

U-53 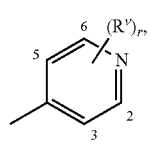

U-54 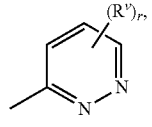

U-55 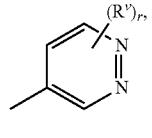

U-56 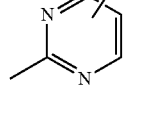

U-57 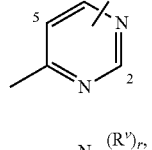

U-58 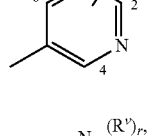

U-59 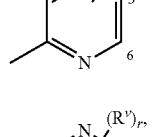

U-60 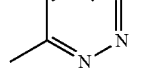

-continued

U-61 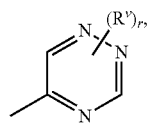

U-62 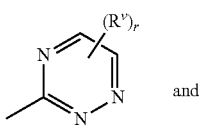

and

U-63 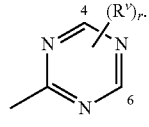

In various embodiments, Q groups include U-49 and U-50. In various embodiments, U-49 groups include U-49 substituted with tert-butyl, cyclopropyl, $CF_2H$, $CF_3$, $CF_2CF_3$, $CF_2CF_2CF_3$ or $CF(CF_3)_2$. In various embodiments, U-50 groups include U-50 substituted with $CF_2H$, $CF_3$, $CF_2CF_3$ or $CF(CF_3)_2$. In some embodiments, Q group is U-49 substituted with $CF_3$.

Using a continuous process to produce N-phenylpyrazole-1-carboxamides provides multiple advantages over the batch process that is practiced in WO 2006/062978. Running continuously allows for faster throughput for a given reactor and helps improve the safety of the process by minimizing the amounts of reactive chemicals that could lead to a runaway reaction. While not all processes can be run in a continuous mode, due to impurity formation or handling issues, for example, it was discovered that the process described herein can be run in a continuous process in high yields and without the formation of new impurities, which is significant to meet the current global pesticide registration needs.

In addition, it was discovered that running in a continuous mode, particularly when feeding into a reaction zone of partially converted material, can be advantageous for the final product particle size, which improves its ease of filtration and product concentration. In a typical batch process, it is desirable to run with high concentrations of starting material, which often leads to the production of undissolved starting material solids that will impact the final product crystallization, resulting in small, hard to filter particles of product. By running continuously into a reaction zone of partially converted material, these solid starting materials quickly dissolve upon entering the reaction zone, essentially eliminating their impact on the crystallization. It was also discovered that the final product has higher solubility in the reaction media as the level of conversion to the compound of Formula 1 increases, which also benefits crystallization and particle size by reducing the amount of supersaturation during crystallization.

Embodiments of the disclosure may include the following.

Embodiment M1. The method including:
(a) combining a compound of Formula 2 with a compound of Formula 3 and a sulfonyl chloride; and
(b) isolating the compound of Formula 1, wherein the combining step (a) is conducted in a continuous process.

Embodiment M1a. The method of Embodiment M1 wherein combining a compound of Formula 2 with a compound of Formula 3 and a sulfonyl chloride may be done in the presence of a base and/or solvent.

Embodiment M2. The method of Embodiment M1 wherein in the combining step (a) the compound of Formula 2, the compound of Formula 3 and the sulfonyl chloride may be continuously charged into a reaction zone; and the isolating step (b) may include continuously removing the compound of Formula 1 from the reaction zone after it is formed.

Embodiment M2a. The method of Embodiment M2 wherein an optional solvent and/or base may also be continuously charged into the reaction zone.

Embodiment M3. The method of Embodiment M1 or Embodiment M2 wherein the rates of charging the compound of Formula 2, the compound of Formula 3 and the sulfonyl chloride and the rate of removal of the compound of Formula 1 may be regulated to provide an average residence time in the reaction zone of two hours or less.

Embodiment M3a. The method of Embodiment M3 wherein optional solvent and/or base are continuously charged into the reaction zone and removed from the reaction zone and the rates are regulated to provide an average residence time in the reaction zone of two hours or less.

Embodiment M4. The method of Embodiment M3 or Embodiment 3a wherein the average residence time in the reaction zone is about 15 minutes or less.

Embodiment M5. The method of any of Embodiments M1 through M4 wherein at least a portion of the compound of Formula 1 may be isolated from the process medium.

Embodiment M6. The method of any of Embodiments M1 through M5 wherein the isolating step may include (b1) quenching the reaction of the compounds of Formulae 2, 3 and the sulfonyl chloride to precipitate the compound of Formula 1 and (b2) filtering the compound of Formula 1 from the process medium.

Embodiment M7. The method of Embodiment M6 wherein the quenching step (b1) may be conducted by adding an antisolvent, such as water, to the reaction stream in a quenching zone.

Embodiment M8. The method of Embodiment M7 wherein the added water may be characterized by a pH value that is neutral, acidic, or basic, or may be present sequentially at different pH values in a plurality of separate quenching zones.

Embodiment M9. The method of any one of Embodiments M1 to M8 further includes drying the compound of Formula 1.

Embodiment M10. The method of any one of Embodiments M1 to M9 wherein the combining step (a) may be conducted under atmospheric pressure in an inert atmosphere.

Embodiment M11. The method of any one of Embodiments M1 to M10 wherein the reaction zone may include a single reactor vessel.

Embodiment M12. The method of any of Embodiments M1 through M10 wherein the reaction zone includes a plurality of reaction subzones with an independent average residence time and temperature for each subzone.

Embodiment M13. The method of M12 wherein the reaction zone includes a first reactor vessel and a second reactor vessel.

Embodiment M14. The method of any one of Embodiments M1 to M13 wherein the reaction zone includes a plug flow reactor, a continual stirred tank reactor, or a combination thereof.

Embodiment M15. The method of any one of Embodiments M1 to M14 wherein the molar ratio of the compound of Formula 2 to the compound of Formula 3 is from about 1.2:1 to about 1:1.2.

Embodiment M16. The method of Embodiment M15 wherein the molar ratio of the compound of Formula 2 to the compound of Formula 3 is from about 1:1 to about 1:1.2.

Embodiment M17. The method of Embodiment M15 wherein the molar ratio of the compound of Formula 2 to the compound of Formula 3 is about 1:1.1.

Embodiment M18. The method of any one of Embodiments M1 to M17 wherein the molar ratio of the sulfonyl chloride to the compound of Formula 2 is at least about 1:1.

Embodiment M19. The method of Embodiment M18 wherein the molar ratio of the sulfonyl chloride to the compound of Formula 2 is from about 1:1 to about 2.5:1.

Embodiment M20. The method of Embodiment M19 wherein the molar ratio of the sulfonyl chloride to the compound of Formula 2 is from about 1.1:1 to about 1.4:1.

Embodiment M21. The method of any one of Embodiments M1 to M18 wherein when $R^2$ is Br or Cl, then the molar ratio of the sulfonyl chloride to the compound of Formula 2 is about 1.2:1. Embodiment M22. The method of any one of Embodiments M1 to M18 wherein when $R^2$ is CN, then the molar ratio of the sulfonyl chloride to the compound of Formula 2 is about 1.4:1. Embodiment M23. The method of any of Embodiments M1 to M22 wherein the sulfonyl chloride is of Formula 4

$$R^8S(O)_2Cl \qquad\qquad 4$$

wherein $R^8$ is a carbon-based radical.

Embodiment M24. The method of Embodiment M23 wherein $R^8$ is $C_1$-$C_4$ alkyl, $C_1$-$C_2$ haloalkyl, or phenyl optionally substituted with 1-3 substituents selected from the group consisting of halogen, $C_1$-$C_3$ alkyl and nitro.

Embodiment M25. The method of Embodiment M24 wherein $R^8$ is $C_1$-$C_2$ alkyl, $CF_3$, phenyl or 4-methylphenyl.

Embodiment M26. The method of Embodiment M25 wherein $R^8$ is $C_1$-$C_2$ alkyl, phenyl or 4-methylphenyl.

Embodiment M27. The method of Embodiment M26 wherein $R^8$ is $CH_3$.

Embodiment M28. The method of any one of Embodiments M1 to M27 wherein the carboxylic acid of Formula 2, aniline of Formula 3 and sulfonyl chloride are combined at a temperature is between about −70 and about 100° C.

Embodiment M29. The method of Embodiment M28 wherein the temperature is between about −20 and about 40° C.

Embodiment M30. The method of Embodiment M26 wherein the temperature is between about −10 and about 30° C.

Embodiment M31. The method of any one of Embodiments M1 to M30 wherein the carboxylic acid of Formula 2 may be combined with the aniline of Formula 3 to form a mixture, and then the mixture is combined with the sulfonyl chloride.

Embodiment M32. The method of any one of Embodiments M1 to M31 wherein a base may be combined with the compounds of Formulae 2 and 3 and the sulfonyl chloride.

Embodiment M33. The method of Embodiment M32 wherein a base may be combined with the mixture either before or after combining with the sulfonyl chloride.

Embodiment M34. The method of Embodiment M33 wherein a base is combined with the compounds of Formulae 2 and 3 to form the mixture before combining with the sulfonyl chloride.

Embodiment M35. The method of any of Embodiments M32 through M34 wherein the amount of the base is at least about 2 equivalents relative to the sulfonyl chloride.

Embodiment M36. The method of Embodiment M35 wherein the amount of base is at least about 2.1 equivalents relative to the sulfonyl chloride. Embodiment M37. The method of Embodiment M36 wherein the amount of the base is from about 2.1 to 2.2 equivalents relative to the sulfonyl chloride.

Embodiment M38. The method of any one of Embodiments M32 to M37 wherein the base is selected from tertiary amines, including optionally substituted pyridines).

Embodiment M39. The method of Embodiment M38 wherein the base is selected from optionally substituted pyridines and mixtures thereof.

Embodiment M40. The method of Embodiment M39 wherein the base is selected from 2-picoline, 3-picoline, 2,6-lutidine, pyridine and mixtures of the foregoing.

Embodiment M41. The method of Embodiment M40 wherein the base is 3-picoline.

Embodiment M42. The method of any one of Embodiments M1 to M41 wherein a solvent may be combined with the compounds of Formulae 2 and 3 and the sulfonyl chloride.

Embodiment M43. The method of Embodiment M42 wherein the solvent is combined with the compounds of Formulae 2 and 3 to form a mixture before combining with the sulfonyl chloride.

Embodiment M44. The method of Embodiment M43 wherein a base is combined with the compounds of Formulae 2 and 3 and the solvent and heated to form a solution before combining with the sulfonyl chloride.

Embodiment M45. The method of Embodiment M43 wherein a base is combined with the compounds of Formulae 2 and 3 and the solvent to form a slurry before combining with the sulfonyl chloride. Embodiment M46. The method of any one of Embodiments M42 through M45 wherein the solvent may be selected from nitriles (e.g., acetonitrile, propionitrile), esters (e.g., methyl acetate, ethyl acetate, butyl acetate), ketones (e.g., acetone, methyl ethyl ketone, methyl butyl ketone, haloalkanes (e.g., dichloromethane, trichloromethane), ethers (e.g., ethyl ether, methyl tert-butyl ether, tetrahydrofuran, p-dioxane), aromatic hydrocarbons (e.g., benzene, toluene, chlorobenzene, dichlorobenzene), tertiary amines (e.g., trialkylamines, dialkylanthranilamides, optionally substituted pyridines), and mixtures thereof Embodiment M47. The method of Embodiment M46 wherein the solvent is selected from tertiary amines (e.g., trialkylamines, dialkylanthranilamides, optionally substituted pyridines) and mixtures thereof.

Embodiment M48. The method of Embodiment M46 wherein the solvent is selected from nitriles (e.g., acetonitrile, propionitrile), esters (e.g., methyl acetate, ethyl acetate, butyl acetate), ketones (e.g., acetone, methyl ethyl ketone, methyl butyl ketone, haloalkanes (e.g., dichloromethane, trichloromethane), ethers (e.g., ethyl ether, methyl tert-butyl ether, tetrahydrofuran, p-dioxane), aromatic hydrocarbons (e.g., benzene, toluene, chlorobenzene, dichlorobenzene), and mixtures thereof.

Embodiment M49. The method of Embodiment M48 wherein the solvent is acetonitrile.

Embodiment M50. The method of any one of Embodiments M1 to M49 further including treating a compound of Formula 1 wherein $R^1$ is H with a halogenating agent to provide a compound of Formula 1 wherein $R^1$ is Cl or Br. Embodiment M51. The method of any one of Embodiments M1 to M49 further including treating a compound of Formula 1 wherein $R^2$ is H with a halogenating agent to provide a compound of Formula 1 wherein $R^2$ is Cl or Br.

In various embodiments, the method of the disclosure may be used to prepare compounds of Formula 1. Accordingly, the invention includes the following Embodiments.

Embodiment C1. The method of Embodiments M1 to M51 used to prepare compounds of Formula 1

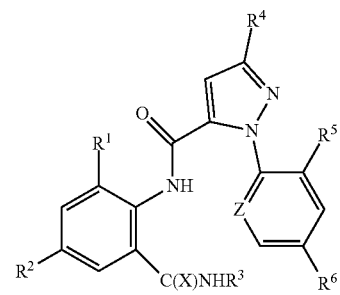

wherein

X is O or S;

Z is $CR^7$ or N;

$R^1$ is H, $CH_3$, Cl or Br, $R^2$ is H, Br, Cl or CN;

$R^3$ is H, $C_1$-$C_4$ alkyl or $C_4$-$C_{10}$ cycloalkylalkyl;

$R^4$ is Cl, Br, $OCF_2H$, $OCH_2CF_3$; or $C_1$-$C_4$ alkyl optionally substituted with halogen; or $C_1$-$C_4$ alkyl substituted with Q;

$R^5$ is F, Cl or Br, $R^6$ is H, F or $C_1$;

$R^7$ is H, F, Cl or Br; and

Q is a 5- or 6-membered aromatic heterocyclic ring optionally substituted with one or more substituents independently selected from the group consisting of halogen, $C_1$-$C_6$ alkyl, $C_3$-$C_6$ cycloalkyl and $C_1$-$C_6$ haloalkyl.

Embodiment $C_2$. The method of any one of Embodiments M1 to M51 wherein in the compound of Formula 3, X is O.

Embodiment $C_3$. The method of any one of Embodiments M1 to M51 wherein in the compound of Formula 3, X is S.

Embodiment $C_4$. The method of any one of Embodiments $C_1$ to $C_3$ wherein in the compound of Formula 3, $R^1$ is Cl.

Embodiment $C_5$. The method of any one of Embodiments $C_1$ to $C_3$ wherein in the compound of Formula 3, $R^1$ is Br.

Embodiment $C_6$. The method of any one of Embodiments $C_1$ to $C_3$ wherein in the compound of Formula 3, $R^1$ is H.

Embodiment $C_7$. The method of any one of Embodiments $C_1$ to $C_6$ wherein in the compound of Formula 3, $R^2$ is Br or Cl.

Embodiment $C_8$. The method of any one of Embodiments $C_1$ to $C_6$ wherein in the compound of Formula 3, $R^2$ is H.

Embodiment $C_9$. The method of any one of Embodiments $C_1$ to $C_6$ wherein in the compound of Formula 3, $R^2$ is CN.

Embodiment C10. The method of any one of Embodiments $C_1$ to $C_9$ wherein in the compound of Formula 3, $R^3$ is $C_1$-$C_4$ alkyl.

Embodiment C11. The method of Embodiment C10 wherein $R^3$ is methyl.

Embodiment C12. The method of Embodiment C10 wherein $R^3$ is, ethyl.

Embodiment C13. The method of Embodiment C10 wherein $R^3$ is isopropyl.

Embodiment C14. The method of any one of Embodiments C1 to C9 wherein in the compound of Formula 3, $R^3$ is $C_4$-$C_{10}$ cycloalkylalkyl.

Embodiment C15. The method of Embodiment C14 wherein $R^3$ is 1-(cyclopropyl)ethyl.

Embodiment C16. The method of any one of Embodiments C1 to C15 wherein in the compound of Formula 2, Z is N.

Embodiment C17. The method of any one of Embodiments C1 to C16 wherein in the compound of Formula 2, $R^4$ is Cl or Br.

Embodiment C18. The method of any one of Embodiments C1 to $C_{16}$ wherein in the compound of Formula 2, $R^4$ is $C_1$-$C_4$ alkyl optionally substituted with halogen or $C_1$-$C_4$ alkyl substituted with Q.

Embodiment C19. The method of C18 wherein $R^4$ is $C_1$-$C_4$ alkyl.

Embodiment C20. The method of C19 wherein $R^4$ is methyl.

Embodiment C21. The method of C18 wherein $R^4$ is $C_1$-$C_4$ alkyl substituted with halogen. Embodiment $C_{22}$. The method of $C_{21}$ wherein $R^4$ is $CF_3$.

Embodiment C23. The method of $C_{21}$ wherein $R^4$ is $CH_2Br$. Embodiment C24. The method of C18 wherein $R^4$ is $C_1$-$C_4$ alkyl substituted with a 5-membered aromatic heterocycle optionally substituted with one or more substituents independently selected from the group consisting of halogen, $C_1$-$C_6$ alkyl, $C_3$-$C_6$ cycloalkyl and $C_1$-$C_6$ haloalkyl.

Embodiment C25. The method of C24 wherein $R^4$ is 5-(trifluoromethyl)-2H-tetrazol-2-ylmethyl.

Embodiment C26. The method of any one of Embodiments C1 to C25 wherein in the compound of Formula 2, $R^5$ is Cl.

Embodiment C27. The method of any one of Embodiments C1 to C26 wherein in the compound of Formula 2, $R^6$ is H.

Embodiment C28. The method of any one of Embodiments C1 to C27 wherein in the compound of Formula 2, $R^6$ is Cl.

Embodiment C29. The method of C1 wherein in the compound of Formula 1, X is O.

Embodiment C30. The method of C1 wherein in the compound of Formula 1, X is S.

Embodiment C31. The method of any one of Embodiments C29 to C30 wherein in the compound of Formula 1, $R^1$ is Cl.

Embodiment C32. The method of any one of Embodiments C29 to C30 wherein in the compound of Formula 1, $R^1$ is Br.

Embodiment C33. The method of any one of Embodiments C29 to C30 wherein in the compound of Formula 1, $R^1$ is H.

Embodiment C34. The method of any one of Embodiments C29 to C33 wherein in the compound of Formula 1, $R^2$ is Br or Cl.

Embodiment C35. The method of any one of Embodiments C29 to C33 wherein in the compound of Formula 1, $R^2$ is H.

Embodiment C36. The method of any one of Embodiments C29 to C33 wherein in the compound of Formula 1, $R^2$ is CN.

Embodiment C37. The method of any one of Embodiments C29 to C36 wherein in the compound of Formula 1, $R^3$ is $C_4$-$C_4$ alkyl.

Embodiment C38. The method of Embodiment C37 wherein $R^3$ is methyl.

Embodiment C39. The method of Embodiment C37 wherein $R^3$ is ethyl.

Embodiment C40. The method of Embodiment C37 wherein $R^3$ is isopropyl.

Embodiment C41. The method of any one of Embodiments C29 to C36 wherein in the compound of Formula 1, $R^3$ is $C_4$-$C_{10}$ cycloalkylalkyl.

Embodiment C42. The method of Embodiment C41 wherein $R^3$ is 1-(cyclopropyl)ethyl.

Embodiment C43. The method of any one of Embodiments C29 to C42 wherein in the compound of Formula 1, Z is N.

Embodiment C44. The method of any one of Embodiments C29 to C43 wherein in the compound of Formula 1, $R^4$ is Cl or Br.

Embodiment C45. The method of any one of Embodiments C29 to C43 wherein in the compound of Formula 1, $R^4$ is $C_1$-$C_4$ alkyl optionally substituted with halogen or $C_1$-$C_4$ alkyl substituted with a 5- or 6-membered aromatic heterocycle optionally substituted with $C_1$-$C_2$ haloalkyl.

Embodiment C46. The method of C45 wherein $R^4$ is $C_1$-$C_4$ alkyl.

Embodiment C47. The method of C46 wherein $R^4$ is methyl.

Embodiment C48. The method of C45 wherein $R^4$ is $C_1$-$C_4$ alkyl substituted with halogen.

Embodiment C49. The method of C48 wherein $R^4$ is $CF_3$.

Embodiment C50. The method of C48 wherein $R^4$ is $CH_2Br$.

Embodiment C51. The method of C45 wherein $R^4$ is $C_1$-$C_4$ alkyl substituted with a 5-membered aromatic heterocycle optionally substituted with $C_1$-$C_2$ haloalkyl.

Embodiment C52. The method of C51 wherein $R^4$ is 5-(trifluoromethyl)-2H-tetrazol-2-ylmethyl.

Embodiment C53. The method of any one of Embodiments C29 to C52 wherein in the compound of Formula 1, $R^5$ is Cl.

Embodiment C54. The method of any one of Embodiments C29 to C53 wherein in the compound of Formula 1, $R^6$ is H.

Embodiment C55. The method of any one of Embodiments C29 to C53 wherein in the compound of Formula 1, $R^6$ is Cl.

Embodiments of this invention, including Embodiments M1 to M51 and C1 to C55 above as well as any other embodiments described herein, can be combined in any manner, and the descriptions of variables in the embodiments pertain not only to the compounds of Formula 1 but also to the starting compounds and intermediate compounds useful for preparing the compounds of Formula 1, including compounds of Formulae 2, 3 and 4. In addition, embodiments of this invention, including Embodiments M1 to M51 and C1 to C55 above as well as any other embodiments described herein, and any combination thereof, pertain to the compositions and methods of the present invention.

Embodiment A1. The method of any one of Embodiments M1 to M51 including compounds of Formula 3 wherein X is O; $R^1$ is $CH_3$; $R^2$ is H, $C_1$, Br or CN; and $R^3$ is $CH_3$ or $CH_2CH_3$.

Embodiment A2. The method of Embodiment A1 including compounds of Formula 3 wherein X is O; $R^1$ is $CH_3$; $R^2$ is Cl or CN; and $R^3$ is $CH_3$.

Embodiment A3. The method of Embodiment A1 including compounds of Formula 3 wherein X is O; $R^1$ is $CH_3$; $R^2$ is H or Br, and $R^3$ is $CH_3$ or $CH_2CH_3$.

Embodiment A4. The method of any one of Embodiments M1 to M51 including compounds of Formula 3 wherein X is O or S; $R^1$ is Cl; $R^2$ is Cl; and $R^3$ is $CH(CH_3)_2$.

Embodiment A5. The method of any one of Embodiments M1 to M51 including compounds of Formula 3 wherein X is O; $R^1$ is H or Br, $R^2$ is Cl; and $R^3$ is 1-(cyclopropyl)ethyl.

Embodiment A6. The method of any one of Embodiments M1 to M51 including compounds of Formula 2 wherein Z is N; $R^4$ is Br, $R^5$ is Cl; and $R^6$ is H or Cl.

Embodiment A7. The method of any one of Embodiments M1 to M51 including compounds of Formula 2 wherein Z is N; $R^3$ is $CH_3$, $CH_2Br$ or 5-(trifluoromethyl)-2H-tetrazol-2-ylmethyl; $R^5$ is Cl; and $R^6$ is H.

Embodiment A8. The method of any one of Embodiments M1 to M51 including compounds of Formula 1 wherein X is O; $R^1$ is $CH_3$; $R^2$ is H, $C_1$, Br or CN; and $R^3$ is $CH_3$ or $CH_2CH_3$.

Embodiment A9. The method of Embodiment A8 including compounds of Formula 1 wherein X is O; $R^1$ is $CH_3$; $R^2$ is Cl or CN; and $R^3$ is $CH_3$.

Embodiment A10. The method of Embodiment A8 including compounds of Formula 1 wherein X is O; $R^1$ is $CH_3$; $R^2$ is H or Br, and $R^3$ is $CH_3$ or $CH_2CH_3$.

Embodiment A11. The method of any one of Embodiments M1 to M51 including compounds of Formula 1 wherein X is O or S; $R^1$ is Cl; $R^2$ is Cl; and $R^3$ is $CH(CH_3)_2$.

Embodiment A12. The method of any one of Embodiments M1 to M51 including compounds of Formula 1 wherein X is O; $R^1$ is H or Br, $R^2$ is Cl; and $R^3$ is 1-(cyclopropyl)ethyl.

Embodiment A13. The method of any one of Embodiments M1 to M51 including compounds of Formula 1 wherein Z is N; $R^4$ is Br, $R^5$ is Cl; and $R^6$ is H or Cl.

Embodiment A14. The method of any one of Embodiments M1 to M51 including compounds of Formula 1 wherein Z is N; $R^3$ is $CH_3$, $CH_2Br$ or 5-(trifluoromethyl)-2H-tetrazol-2-ylmethyl; $R^5$ is Cl; and $R^6$ is H.

Embodiment A15. The method of any one of Embodiments M1 to M51 including compounds of Formula 1 wherein X is O; Z is N; $R^1$ is $CH_3$; $R^2$ is H, $C_1$, Br or CN; $R^3$ is $CH_3$ or $CH_2CH_3$; $R^4$ is Br, $R^5$ is Cl; and $R^6$ is H.

Embodiment A16. The method of any one of Embodiments M1 to M51 including compounds of Formula 1 wherein X is O or S; Z is N; $R^1$ is Cl; $R^2$ is Cl; $R^3$ is $CH_3$ or $CH(CH_3)_2$; $R^4$ is Br; $R^5$ is Cl; and $R^6$ is H or Cl.

Specific Embodiments of the Invention include the method of any one of Embodiments M1 to M51, C1 to C55 and A1 to A16 used to prepare a compound of Formula 1 selected from the group consisting of:

3-bromo-N-[4-chloro-2-methyl-6-[(methylamino)carbonyl]phenyl]-1-(3-chloro-2-pyridinyl)-1H-pyrazole-5-carboxamide (also known as chlorantraniliprole), 3-bromo-1-(3-chloro-2-pyridinyl)-N-[4-cyano-2-methyl-6-[(methylamino)carbonyl]phenyl]-1H-pyrazole-5-carboxamide (also known as cyantraniliprole), 1-(3-chloro-2-pyridinyl)-N-[4-cyano-2-methyl-6-[(methylamino)carbonyl]phenyl]-3-[[5-(trifluoromethyl)-2H-tetrazol-2-yl]methyl]-1H-pyrazole-5-carboxamide (also known as tetraniliprole), and 3-bromo-N-[2-bromo-4-chloro-6-[[(1-cyclopropylethyl]amino]carbonyl]phenyl-1-(3-chloro-2-pyridinyl)-1H-pyrazole-5-carboxamide (also known as cyclaniliprole).

In the following Schemes the definitions of Q, X, Z, $R^1$, $R^2$, $R^3$, $R^4$, $R^5$, $R^6$ and $R^7$ in the compounds of Formulae 1 through 41 below are as defined above in the Summary of the Invention and description of embodiments unless otherwise indicated. Compounds of Formulae 2a through 2f are subsets of Formula 2 and compounds of Formulae 3a through 3c are subsets of Formula 3.

As shown in Scheme 1, this disclosure relates to a method for preparing compounds of Formula 1 by coupling carboxylic acids of Formula 2 with anilines of Formula 3 using a sulfonyl chloride, typically in the presence of a base and a solvent.

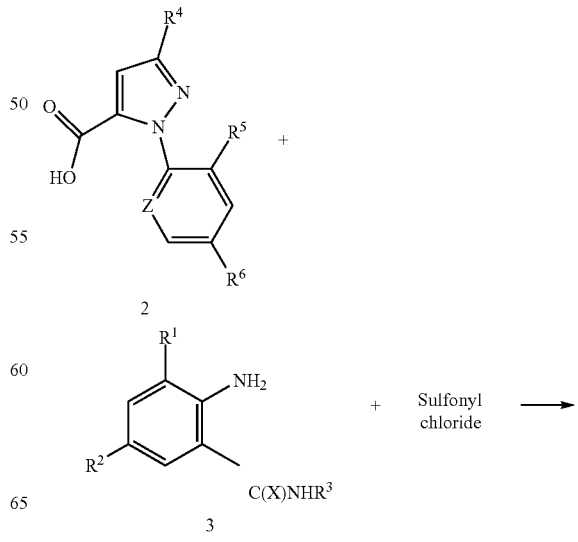

Scheme 1

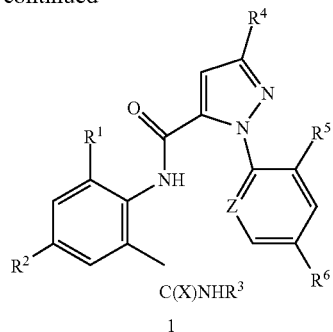

Thus, in the present method a pyrazolecarboxylic acid of Formula 2, an aniline of Formula 3 and a sulfonyl chloride are combined (i.e. contacted) in a continuous process to provide the corresponding N-phenylpyrazole-1-carboxamide of Formula 1.

As shown in FIG. 1, the continuous process 100 includes continuously charging a compound of Formula 2, a compound of Formula 3 and a sulfonyl chloride into a reaction zone 110 where they can combine to provide the corresponding compound of Formula 1. As used herein, the term "reaction zone" refers to a locus in the continuous process stream wherein a compound of Formula 2, a compound of Formula 3, a sulfonyl chloride and/or any moieties derived therefrom are in sufficient proximity that they can contact each other and combine to form the compound of Formula 1. As described in more detail below, an optional solvent and/or an optional base may also be continuously charged into the reaction zone to facilitate the reaction.

In various embodiments, at least a portion of the compound of Formula 1 may then be continuously removed from the reaction zone 110 to a quench zone 120 where it is contacted with an antisolvent, as described in more detail below. Suitable antisolvents may include any solvent capable of precipitating a compound of Formula 1. In some embodiments, suitable antisolvents include water. Following quenching, the compound of Formula 1 may be isolated in an isolation step 130 from the liquid process components and water-soluble reaction byproducts by, for example, crystallization and/or filtration.

In other embodiments, at least a portion of the compound of Formula 1 may be directly isolated using any suitable isolation technique known to a person of skill in the art, such as crystallization or filtration, bypassing any quenching step.

Figure 2:
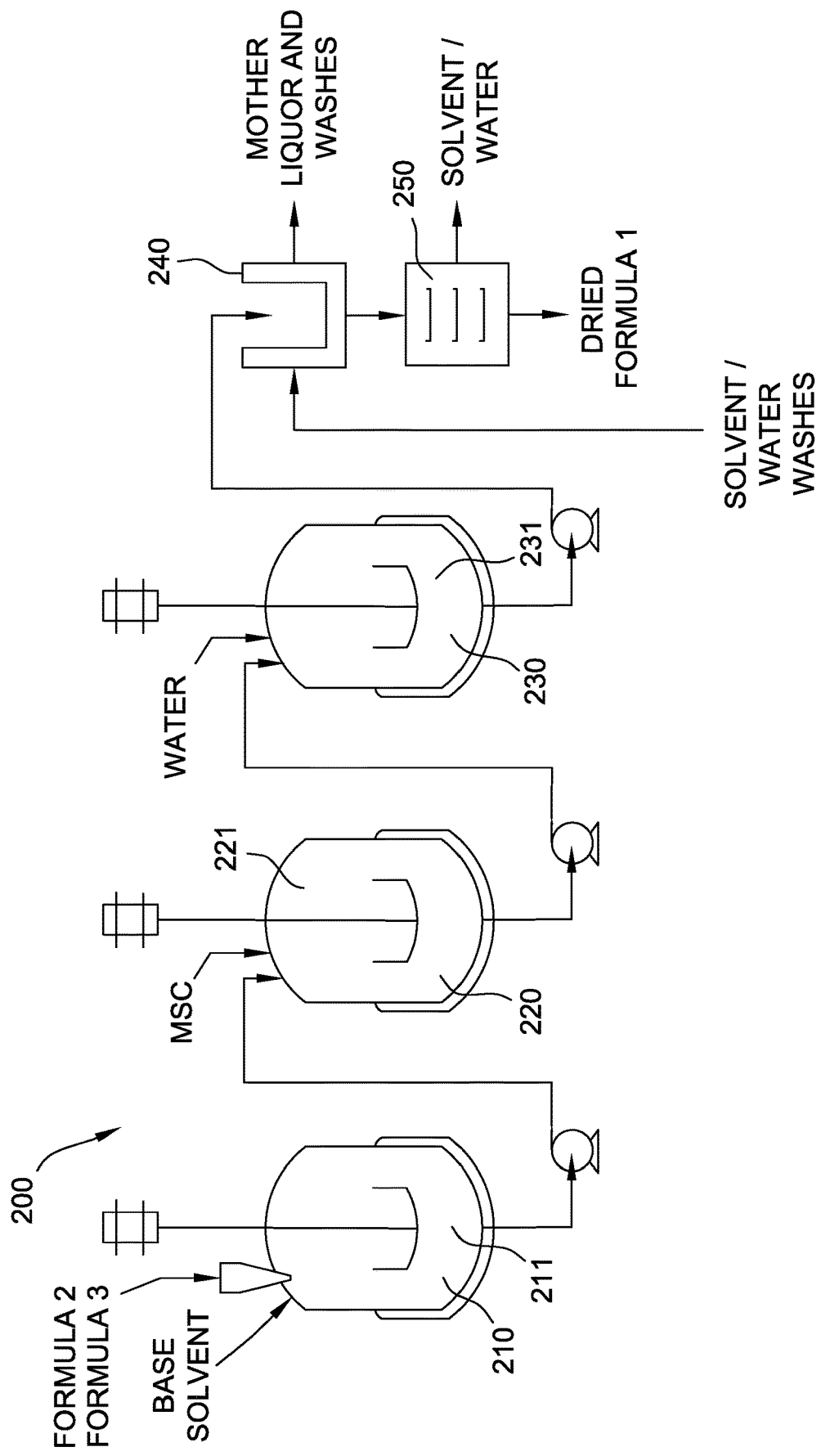
FIG. 2 shows a schematic drawing of a series of reactors, e.g. Reaction CSTR and Quench CSTR, suitable for preparing a compound of Formula 1 by the continuous process of the disclosure.

A simplified schematic drawing of a processing system 200 suitable for conducting the continuous process 100 illustrated in FIG. 1 is shown in FIG. 2. The processing system 200 includes a series of three continuous stirred tank reactors (CSTRs) 210, 220, 230. In various embodiments, a CSTR is defined as a reactor wherein the contents of the reactor are generally well mixed (for example, by stirring, agitation, gassed mixing, or fluid impingement), but can range from "highly mixed", where substantially no variations in chemical concentration and temperature can be observed in the reactor, to a level of mixedness approaching "nonmixed", which means high variations in local concentration and temperatures may occur. The first CSTR 210 includes a batch mixing zone 211 where the compound of Formula 2, the compound of Formula 3, solvent and base are mixed. Compounds of Formula 2 and Formula 3 are generally solids and may be added as such by well-known powder addition methods such as from a hopper and/or via a metering screw feed. Alternatively, one or both may be dissolved in a solvent prior to introduction into the mixing zone. In some embodiments the batch mixture optionally may be heated if necessary to provide a solution wherein the base, compound of Formula 2, and compound of Formula 3 are all dissolved in the solvent. In other embodiments, one or more of the base compound of Formula 2 and compound of Formula 3 remains as a solid suspended in the solvent, providing a slurry.

After mixing, the solution or slurry is continuously pumped into a second CSTR 220, having a reaction zone 221 therein, including the reaction zone 221 wherein a sulfonyl chloride, such as methyl sulfonyl chloride (MSC), is continuously added to the mixture. In the second CSTR 220, the sulfonyl chloride, compound of Formula 2 and compound of Formula 3 are combined to form a compound of Formula 1. In various embodiments, substantially all of compound of Formula 2 and compound of Formula 3 are consumed to form the compound of Formula 1. In some embodiments, at least a portion of the compound of Formula 1 may precipitate from the reaction mixture after its formation. In various embodiments, the compound of Formula 1 may be continuously removed from the reaction zone, such as in a slurry in the solvent, and continuously charged into a third CSTR 230 that includes a quench zone 231. The compound of Formula 1 may then be transferred to a separation device 240, such as a centrifuge or continuous filter, and dried in a drying zone 250, such as a continuous dryer.

Following an initial start-up period for filling the reaction zone reactor(s) to the desired volume(s), the rates of introduction and removal may be substantially constant or variable (e.g. introduction and/or removal may be intermittent), but are balanced on average to reach a desired residence time in the reaction zone. For example, the rates of introduction and removal are not simultaneously zero during the continuous process. Alternatively, intermittent introduction and/or removal may be useful for coupling the continuous process to upstream (e.g. batch charging of one or more reactants) or downstream batch processing equipment and/or steps. Desirably the rates of introduction of compounds of Formulae 2 and 3 into the reaction zone and removal of the compound of Formula 1 may be regulated so that moieties derived from compounds of Formulae 2 and 3 and incorporated into the compound of Formula 1 have an average residence time in the reaction zone of sufficient duration to provide conversion rates of greater than about 85, 90, 95, or 98%. For example, the average residence time in the reaction zone may range from about 15 minutes to about 2 hours, such as about two hours or less, or about one hour or less, about 30 minutes or less, or about 15 minutes or less. The average residence time is defined as the average amount of time a given molecule spends in the reaction zone (or quench zone as discussed below). While the residence time distribution may be very broad (i.e., some molecules can exit the reaction zone quickly while others in the same reaction zone remain for longer periods time), the average residence time is generally defined as the volume of the reactor(s) in the reaction zone (or quench zone) divided by the average flow rate of feed stream. While the reaction of compounds of Formulae 2 and 3 and sulfonyl chloride is relatively rapid, in some embodiments, it may be desirable to have average residence times longer than needed to achieve the desired level of conversion, in order to provide reduced fouling of equipment, improved interface with other processes, improved crystal properties, e.g., that allow for more efficient recovery of the resulting compound of Formula 1, or for other reasons. In various embodiments, each reactor in the reaction zone is operated at an independent residence time and temperature.

A wide range of equipment may be used to carry out the continuous reaction. This process may include the use of and is not limited to: continuous stirred tank reactors (CSTR), plug flow reactors (PFR), fluidized bed reactors, packed bed reactors, continuous crystallizers, static mixers, reactive distillation columns, and any combination of these thereof. Examples of CSTRs may be anything from a traditional agitated vessel to a pumping zone of a centrifugal pump. A plug flow reactor (PFR) may be as simple as flow through a pipe, or more complex, e.g., like a shell and tube exchanger or a plate and frame exchanger. In general, a PFR has distinct differences between inlet and outlet concentrations of the reactor.

Figure 3:
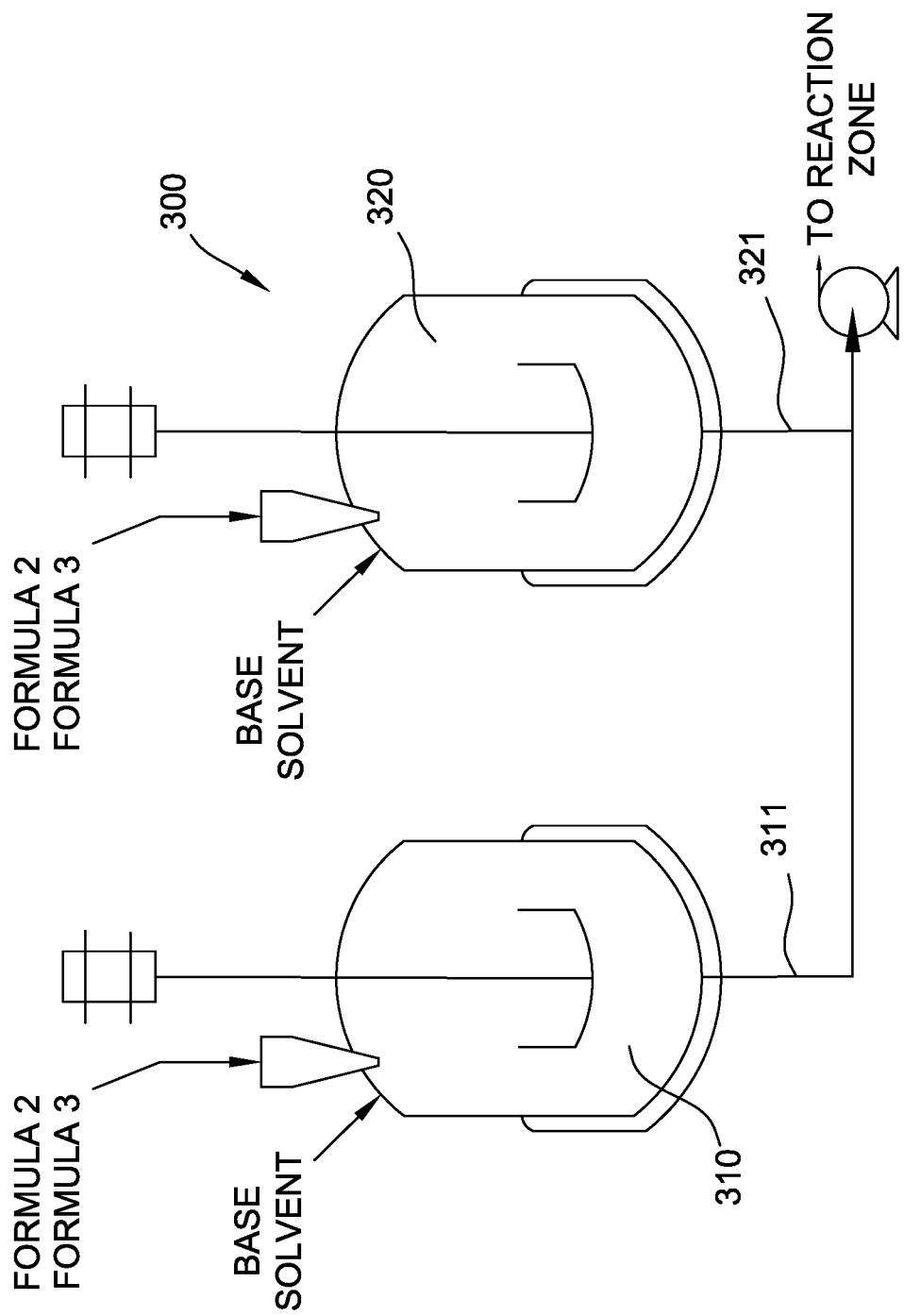
FIG. 3 shows a schematic drawing of a plurality of batch mix tanks suitable for mixing a compound of Formula 2, a compound of Formula 3, a solvent and a base for introduction into a reaction zone of the continuous process of the disclosure.

As discussed above with reference to FIG. 2, compounds of Formulae 2 and 3 may be mixed, optionally with solvent and/or base, prior to their introduction into the reaction zone. FIG. 3 shows a schematic drawing of a plurality of batch mix tanks 300 suitable for mixing a compound of Formula 2, a compound of Formula 3, solvent and base for introduction into the reaction zone of a continuous process of this disclosure. The plurality of batch mix tanks 300 allows for a first batch mix tank 310 to be charged, and optionally heated, to provide a first batch mixture 311 for introduction into the reaction zone. While the contents of the first batch mix tank are being discharged into the reaction zone, a second batch mix tank 320 can be charged, and optionally heated, to prepare a second batch mixture 321 for subsequent introduction into the reaction zone.

Figure 4:
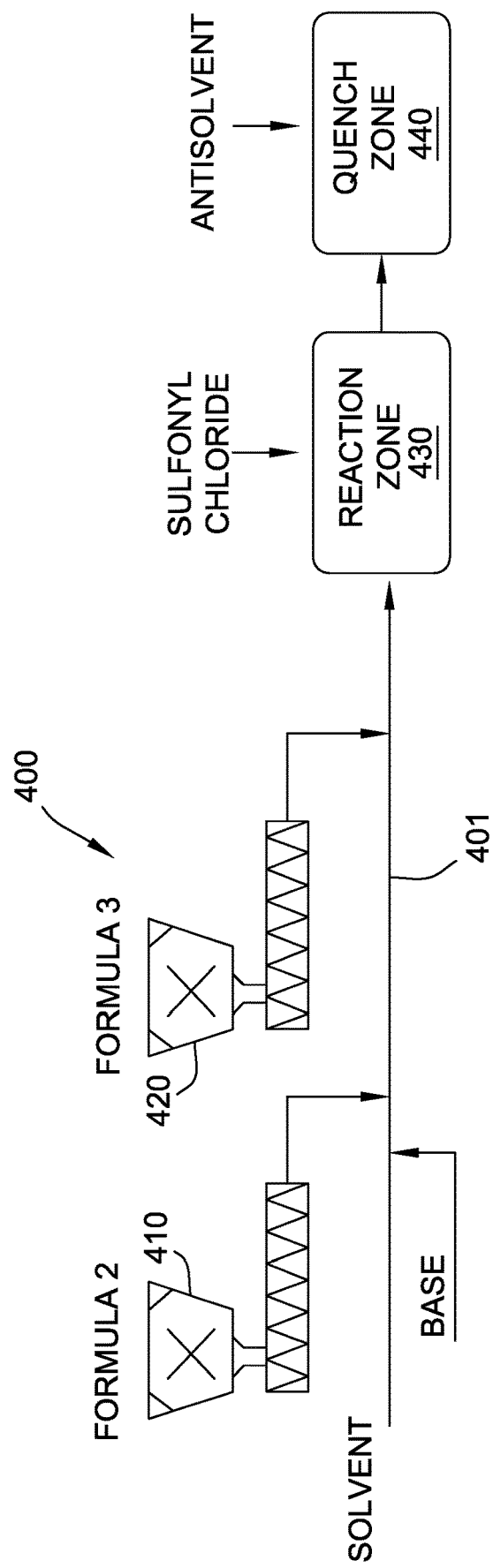
FIG. 4 shows a schematic drawing of a charging system suitable for powder mixing a compound of Formula 2, a compound of Formula 3, a solvent and a base for introduction into a reaction zone of the continuous process of the disclosure.

FIG. 4 shows a schematic drawing of an alternative charging system 400 suitable for powder mixing a compound of Formula 2, a compound of Formula 3, solvent and base for introduction into the reaction zone of a continuous process of this disclosure. In this embodiment, base is introduced into a flow of solvent 401 through the process equipment followed by the downstream introduction of the compound of Formula 2 fed substantially continuously (e.g. from a metering screw feed) from a first solids hopper 410 into the solvent flow 401. Similarly, the compound of Formula 3 is fed from a second solids hopper 420 into the solvent flow 401 downstream of the first solids hopper 410, prior to entry into the reaction zone 430. There the sulfonyl chloride is fed into the solvent stream where it can react with the compound of Formula 2 to form an intermediate that reacts with the compound of Formula 3 to provide the compound of Formula 1. In various embodiments, base may also be added at further points downstream in the solvent flow, as well as directly into the reaction zone 430. From the reaction zone 430, the compound of Formula 1 may then be transferred to a quench zone 440.

Figure 5:
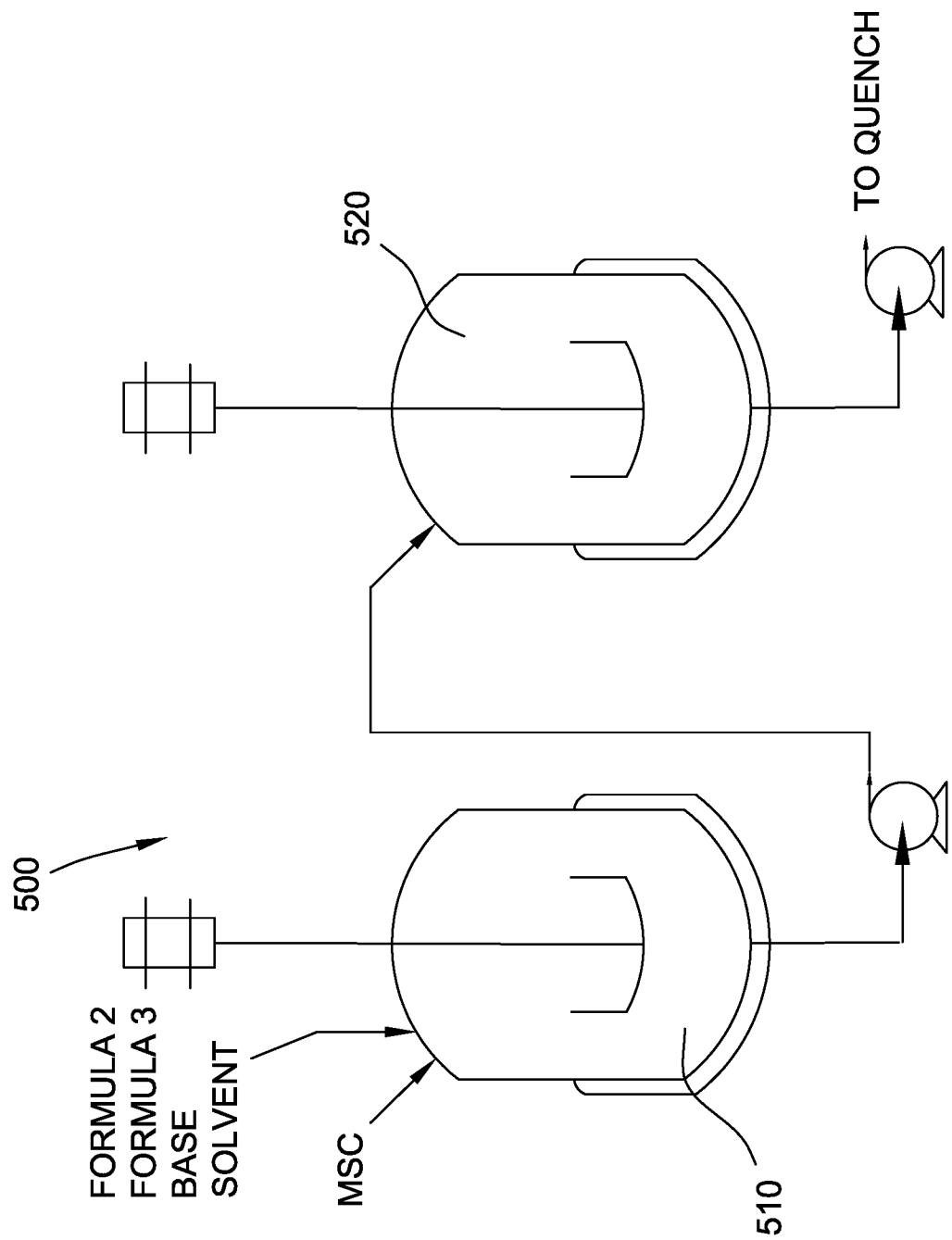
FIG. 5 shows a schematic drawing of a reaction zone of the continuous process of the disclosure, said reaction zone including a series of two continuous stirred tank reactors (CSTRs) that provide a combination of a first reaction subzone within the first CSTR, wherein a mixture of a compound of Formula 2, a compound of Formula 3, a solvent and a base is introduced and wherein sulfonyl chloride, e.g. methanesulfonyl chloride (MSC), is introduced, and a second reaction subzone within the second CSTR, wherein the reaction of the mixture and the MSC is finished.

FIG. 5 shows a schematic drawing of a series of two continuous stirred tank reactors 500 that provide a combination of a first reaction subzone 510 and a second reaction subzone 520, each including a continuous stirred tank reactor, in the reaction zone of a continuous process of this disclosure. As used herein, the term "subzone" refers to a locus (such as a vessel) within the reaction zone or the quench zone (see below in which a given set of process parameters applies). In the first reaction subzone 510, all the components of the reaction mixture are introduced, mixed, and at least partially reacted. In the second reaction subzone 520, the reaction can proceed to completion (i.e. to the desired conversion level) and provide the compound of Formula 1 in a form that facilitates its isolation, such as formation of crystal size that provides for rapid filtration. Because of this, the second reaction subzone 520 may also be known as a finishing zone. The volume, average residence time, temperature, mixing and/or other process parameters may be the same or different in the first and second reaction subzones 510, 520. For example, the temperature in the first reaction subzone 510 may be hotter than in the second reaction subzone 520.

Figure 6:
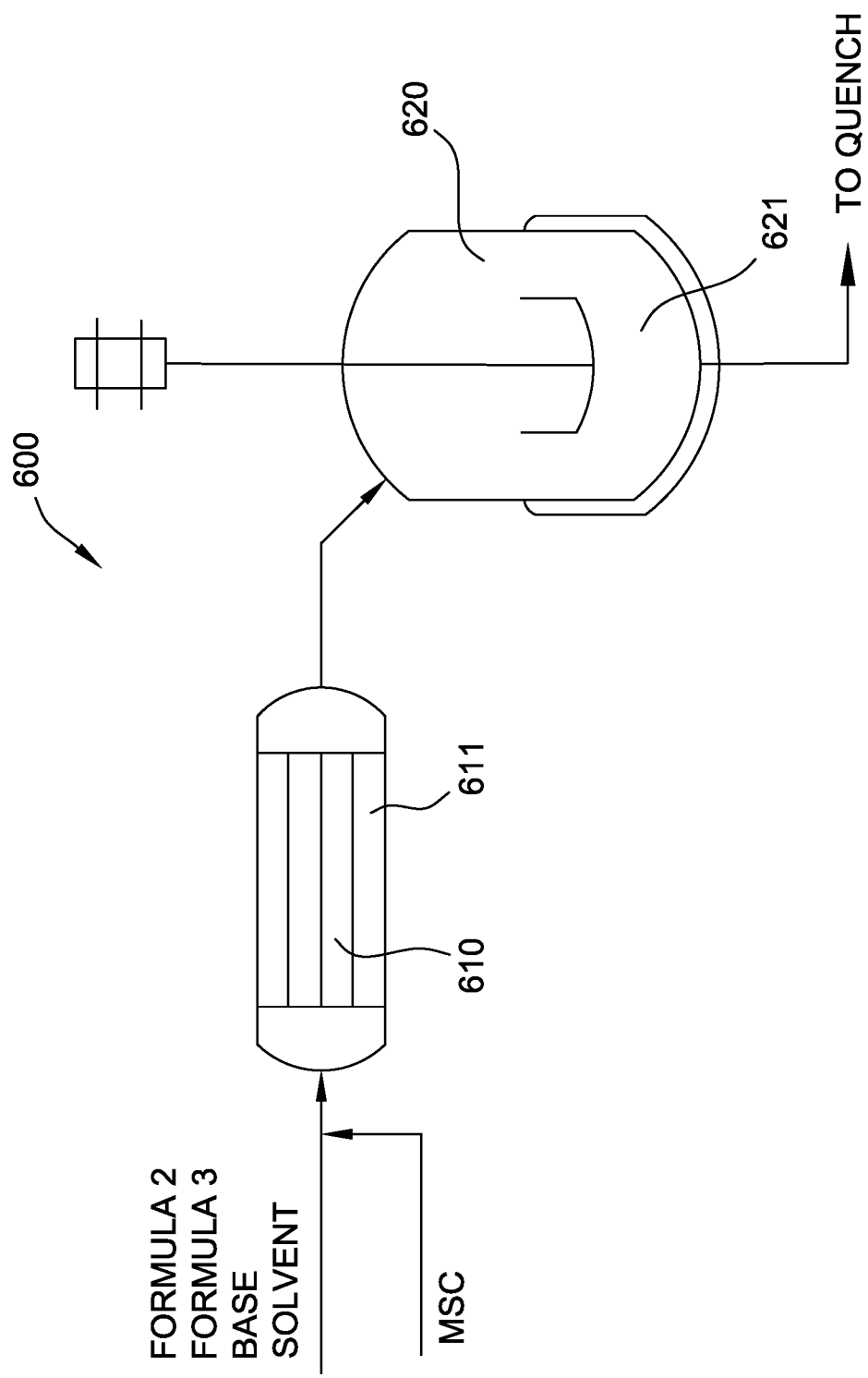
FIG. 6 shows a schematic drawing of a reaction zone of the continuous process of the disclosure, said reaction zone including a combination of a plug flow reactor and a continuous stirred tank reactor that provide a first reaction subzone within the plug flow reactor, wherein a mixture of a compound of Formula 2, a compound of Formula 3, a solvent and a base is introduced, and wherein sulfonyl chloride, e.g. methanesulfonyl chloride (MSC) is introduced, and a second reaction subzone within the continuous stirred tank reactor wherein the reaction of the mixture and the MSC is finished.

FIG. 6 shows a schematic drawing of a combination of a first reaction subzone 610 including a plug flow reactor 611 and a second reaction subzone 620 including a continuous stirred tank reactor 621 in the reaction zone 600 of a continuous process of this disclosure. As discussed with reference to FIG. 5, the first reaction subzone 610 provides for mixing of the components of the process and at least partial conversion, while the second reaction subzone 620 can provide finishing conditions.

Figure 7:
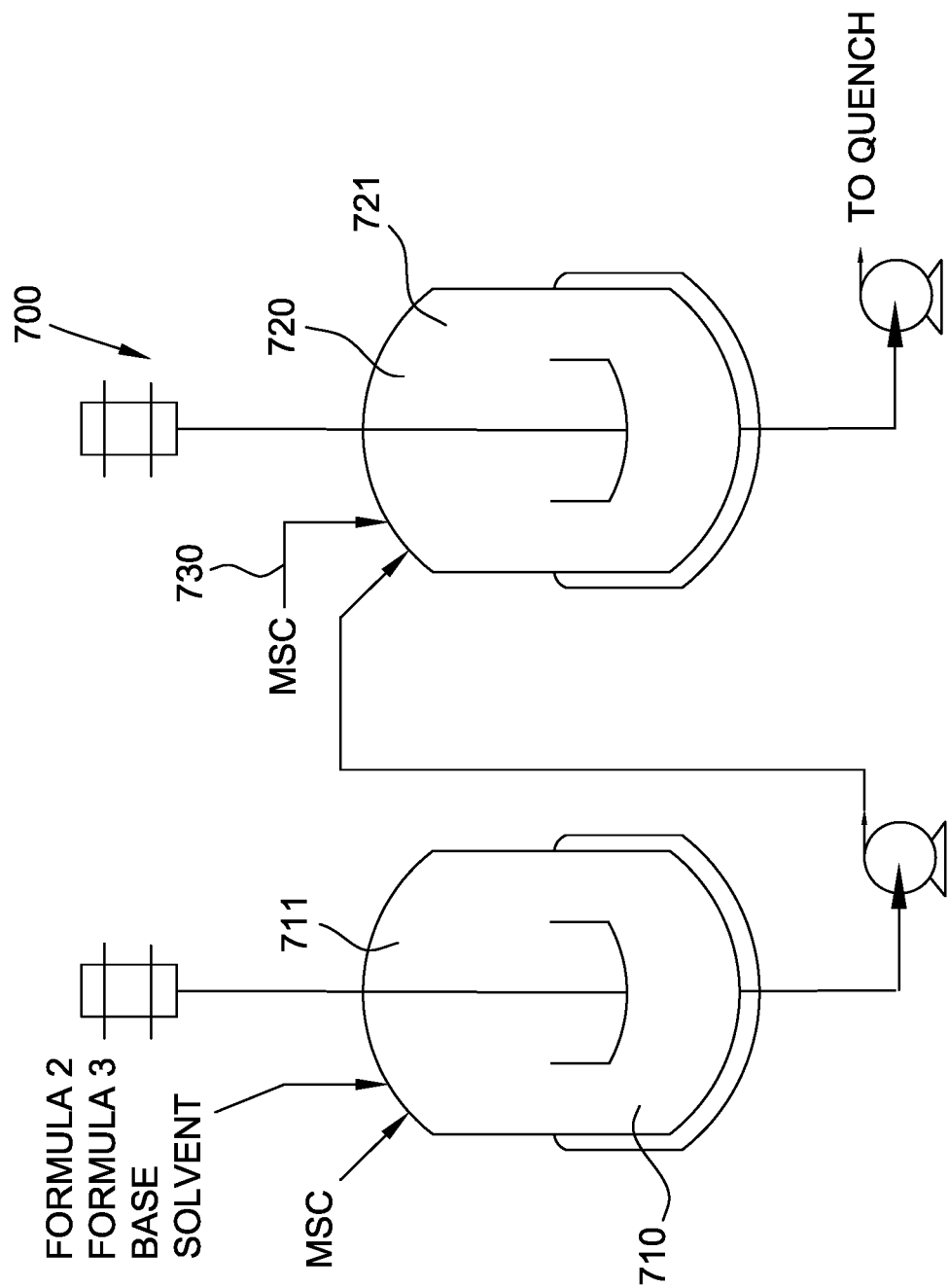
FIG. 7 shows a schematic drawing of a reaction zone of the continuous process of the disclosure, the reaction zone including a series of two continuous stirred tank reactors (CSTRs) that provide a combination of a first reaction subzone within the first CSTR, wherein a mixture of a compound of Formula 2, a compound of Formula 3, a solvent and a base is introduced and wherein methyl sulfonyl chloride (MSC) is introduced and a second reaction subzone within the second CSTR having an additional methyl sulfonyl chloride feed stream.

FIG. 7 shows a schematic drawing of a series of two continuous stirred tank reactors 700 to provide a combination of a first reaction subzone 710 including a continuous stirred tank reactor 711 and a second reaction subzone 720 including a continuous stirred tank reactor 721 with an additional sulfonyl chloride feed stream 730 in the reaction zone of a continuous process of this disclosure. This may allow for more controlled addition of the sulfonyl chloride. It may also allow for additional sulfonyl chloride to be added if some is consumed in formation of a compound of cyclo-1 (see below).

In any combination of first and second reaction subzones, transfer between the zones may allow for in-line monitoring (not shown in FIG. 5, 6, or 7) of the progress of the reaction and allow for adjustment of process parameters in the second subzone.

Figure 8:
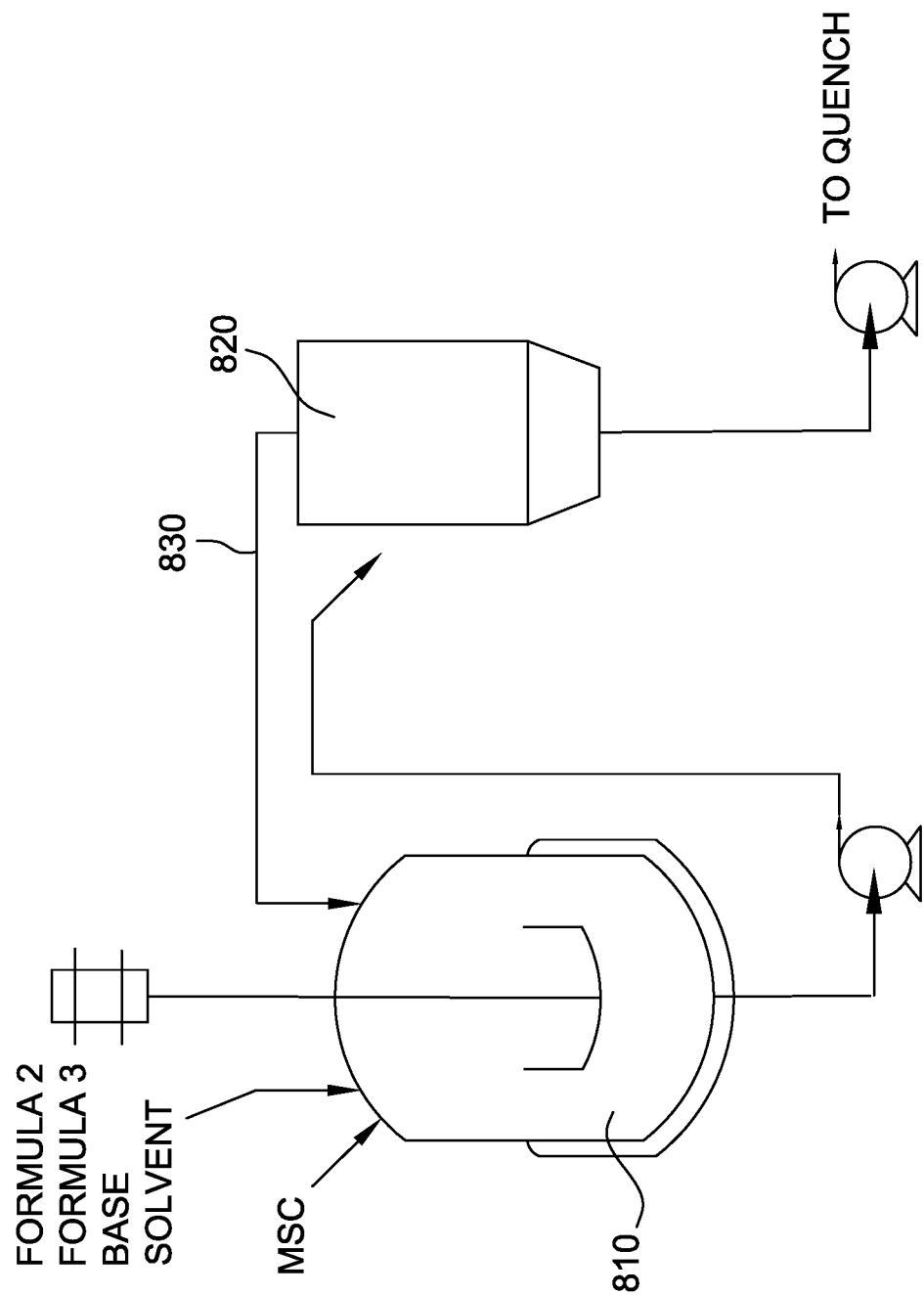
FIG. 8 shows a schematic drawing of an apparatus useful in a process of the present disclosure including a continuous stirred tank reactor combined with a solids concentrator (e.g. hydrocyclone) that allows removal of solids to a quench zone and recycling of reaction solution back to the continuous stirred tank reactor.

FIG. 8 shows a schematic drawing of a continuous stirred tank reactor with a solids concentrator 820 (e.g. hydrocyclone) that allows preferential removal of solids (e.g. the compound of Formula 1) to the quench zone while sending a recycle stream 820 of reaction solution back to the continuous stirred tank reactor reaction zone 810. This recycle loop may allow for running the reaction at lower reactant concentrations without the yield losses associated with running in dilute conditions, which can be advantageous for reaction selectivity, crystal formation, and slurry handling. It may also allow for in-line monitoring of the reaction.

Although a wide range of reactant ratios is possible, the nominal mole ratio of the Formula 3 compound to the Formula 2 compound is typically from about 0.9 to 1.1, or about 1.0 so that both compounds can be fully consumed. The present method can be conducted over a wide range of temperatures, for example at temperatures ranging from −70° C. to +100° C. or from −20° C. to +40° C., or from −10° C. to +30° C. for reasons of convenient operation, favorable reaction rate and selectivity, and high process yield. In some embodiments, temperatures are from 30° C. to 60° C.

The sulfonyl chloride compound is used as a reactant to facilitate coupling of the carboxylic acid of Formula 2 with the aniline of Formula 3 to form the N-phenylpyrazole-1-carboxamide of Formula 1. The nominal mole ratio of the sulfonyl chloride to the Formula 2 compound is typically from about 1.0 to 2.5, or from about 1.1 to 1.4 when the cyclization side reaction described below occurs to no more than a small extent (i.e. 0-10%). Sulfonyl chlorides are generally of the formula $R^8S(O)_2Cl$ (Formula 4) wherein $R^8$ is a carbon-based radical. Typically for the present method $R^8$ is $C_1$-$C_4$ alkyl, $C_1$-$C_2$ haloalkyl, or phenyl optionally substituted with 1-3 substituents selected from the group consisting of halogen, $C_1$-$C_3$ alkyl and nitro. Sulfonyl chloride compounds suitable for the present method because of their commercial availability include methanesulfonyl chloride ($R^8$ is $CH_3$), propanesulfonyl chloride ($R^8$ is $(CH_2)_2CH_3$), benzenesulfonyl chloride ($R^8$ is Ph), and p-toluenesulfonyl chloride ($R^8$ is 4-$CH_3$-Ph). In some embodiments, methanesulfonyl chloride is used for reasons of lower cost, ease of addition and/or less waste.

In the present method, the sulfonyl chloride is combined with the pyrazolecarboxylic acid of Formula 2 and the aniline of Formula 3. The reactants can be combined in a variety of orders, such as combining the sulfonyl chloride with the carboxylic acid of Formula 2 to form a mixture and then combining the mixture with the aniline of Formula 3. However, in various embodiments for preparing the particular N-phenylpyrazole-1-carboxamides of Formula 1, the order of combination may include combining the carboxylic acid of Formula 2 with the aniline of Formula 3 to form a mixture and then combining the sulfonyl chloride with the mixture (e.g., adding the sulfonyl chloride to the mixture of the compounds of Formulae 2 and 3), because this order of addition allows convenient control of the coupling process. The rate of reaction is readily controlled by controlling the rate of addition of the sulfonyl chloride compound. Therefore, one embodiment of the present method includes the sequential steps of (1) combining a carboxylic acid of Formula 2 and an aniline of Formula 3 to form a mixture, and (2) then combining the mixture with a sulfonyl chloride. Although addition of the sulfonyl chloride to the mixture containing the aniline of Formula 2 potentially could result in undesirable side reactions, the stereoelectronic profiles of the compounds of Formulae 2 and 3 facilitate obtaining remarkably high yields of compounds of Formula 1 using the present method.

The compound of Formula 1 is formed when the starting compounds of Formulae 2 and 3 and the sulfonyl chloride are contacted with each other in a combined liquid phase, in which each is at least partially soluble. Particularly as the starting materials of Formulae 2 and 3 are typically solids at ordinary ambient temperatures, the method is most satisfactorily conducted using a solvent in which the starting compounds have significant solubility. Thus, typically the method is conducted in a liquid phase including a solvent. In some cases, the carboxylic acid of Formula 2 may have only slight solubility but its salt with added base may have more solubility in the solvent. Suitable solvents for this method include nitriles such as acetonitrile and propionitrile; esters such as methyl acetate, ethyl acetate, and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF), and p-dioxane; aromatic hydrocarbons such as benzene, toluene, chlorobenzene, and dichlorobenzene; tertiary amines such as trialkylamines, dialkylanilines, and optionally substituted pyridines; and mixtures of the foregoing. Solvents of note include acetonitrile, propionitrile, ethyl acetate, acetone, MEK, dichloromethane, methyl tert-butyl ether, THF, p-dioxane, toluene, and chlorobenzene. Acetonitrile is a particularly notable solvent, as it often provides products in superior yield and/or purity.

As the reaction of the present method generates hydrogen chloride as a byproduct, which would otherwise bind to basic centers on the compounds of Formulae 1, 2 and 3, the method is most satisfactorily conducted in the presence of at least one added base. The base may also facilitate constructive interaction of the carboxylic acid with the sulfonyl chloride compound and the aniline. Reaction of an added base with the carboxylic acid of Formula 2 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as solvent the nominal mole ratio of the base charged to the sulfonyl chloride charged is typically from about 2.0 to 2.2, or from about 2.1 to 2.2. Suitable bases include tertiary amines, including substituted pyridines. In various embodiments, suitable bases include 2-picoline, 3-picoline, 2,6-lutidine, and pyridine. In one embodiment, a suitable base is 3-picoline, as its salts with carboxylic acids of Formula 2 are often highly soluble in solvents such as acetonitrile.

The features of the present method provide efficient production of the N-phenylpyrazole-1-carboxamide of Formula 1 while limiting the amounts of the carboxylic acid, the sulfonyl chloride and the aniline that are consumed during the formation of the N-phenylpyrazole-1-carboxamide and reducing waste. The present method allows convenient control of the coupling process and provides a method involving fewer and simpler operations as compared to previously known processes for producing N-phenylpyrazole-1-carboxamides such as Formula 1.

In one embodiment of the present method, the pyrazolecarboxylic acid of Formula 2, the amide of Formula 3, and a suitable base may be combined in a suitable solvent, followed by the addition of the sulfonyl chloride compound (either alone or mixed with a suitable solvent).

Following the reaction of Formula 2 and Formula 3 to form the compound of Formula 1, the reaction mixture may be quenched in a quenching zone by the addition of an antisolvent, such as water. The water converts any unconsumed sulfonyl chloride to its corresponding acid or salt with any excess base present. Addition of water also facilitates complete precipitation of Formula 1 from the reaction medium. The quench water may be neutral, acidic or basic. In some embodiments, the quench water may include portions of water having different pH values, added sequentially in a plurality of separate quenching subzones. As discussed in more detail below, adjustment of the pH of the quench water minimizes the amount of Formula cyclo-1 recovered from the process.

The rates of introduction into and/or removal from the quench zone of the compound of Formula 1 may be substantially constant or variable (e.g. introduction and/or removal may be intermittent), but are balanced on average to reach a desired residence time in the quench zone. For example, the rates of introduction and removal are not simultaneously zero during the continuous process. Alternatively, intermittent introduction and/or removal may be useful for coupling the continuous process to upstream or downstream batch processing equipment and/or steps (e.g. batch filtration). For example, the average residence time in the quench zone may range from about 15 minutes to about 2 hours, such as two hours or less, one hour or less, 30 minutes or less, or 15 minutes or less. While quenching of the reaction is relatively rapid, in some embodiments, it may be desirable to have longer average residence times to provide reduced equipment fouling, improved interface with other processes, crystal properties that allow for more efficient recovery of the compound of Formula 1, or for other reasons. For example, it may be desirable to have a longer residence time in the quench zone to provide an average crystal size suitable for efficient filtering of the compound of Formula 1.

The product N-phenylpyrazole-1-carboxamides of Formula 1 can be isolated from the reaction mixtures by methods known to those skilled in the art, including crystallization, filtration, and extraction. As shown in FIGS. 2 and 8, isolation of the compound of Formula 1 as a solid can be accomplished with a wide variety of process equipment, including for example but not limitation, solids concentrators, centrifuges, hydrocyclones, continuous filters, dryers and the like. After isolation, the compound of Formula 1 may be further processed, such as for example but not limited to, washing with a solvent and/or water, recrystallization, conversion of a compound of cyclo-1, if present (see below), to the compound of Formula 1. The compound of Formula 1 can be combined with additional materials including other active ingredients and/or formulation adjuvants for use as insecticides.

As shown in Scheme 2, in some cases, partial cyclization of amides 1 to iminobenzoxazines of Formula cyclo-1 occurs under the conditions of the coupling reaction.

base can facilitate completion of the coupling reaction. The cyclization side reaction stoichiometrically consumes an equivalent of sulfonyl chloride in addition to the equivalent of sulfonyl chloride consumed in the coupling reaction. Therefore if 100% cyclization were to occur, a 2:1 mole ratio of sulfonyl chloride to Formula 2 compound would stoichiometrically be needed to achieve complete consumption of starting materials, and typically up to about a 2.5:1 mole ratio of sulfonyl chloride to Formula 2 compound would be used, in contrast to an about 1.4:1 mole ratio of sulfonyl chloride to Formula 2 compound when the cyclization occurs only to the extent of 5-10% (as is typical with most bases when $R^2$ is CN) and an about 1.2:1 mole ratio of sulfonyl chloride to Formula 2 compound when the cyclization side reaction is negligible (as is typical with most bases when $R^2$ is Br, Cl or H). The additional quantities of sulfonyl chloride and base can be added while the reaction is in progress if the cyclization reaction is observed to be occurring.

The above illustrates a valuable feature of this continuous process, which is that additional quantities of any of the components of the process can be continuously added as Scheme 2

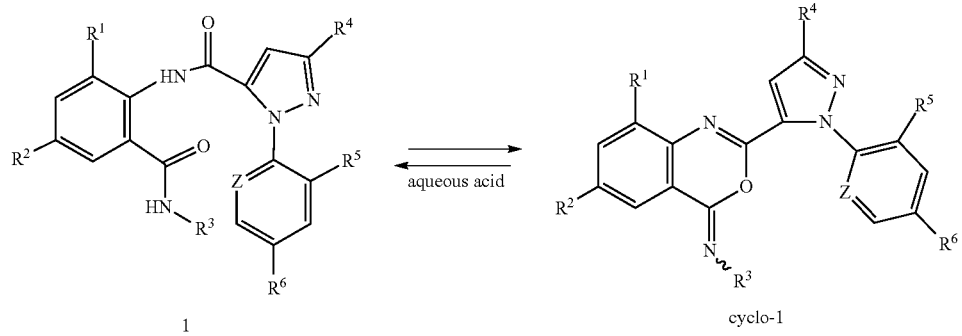

In these cases, it is often advantageous to convert the Formula cyclo-1 compound back to the amide of Formula 1 prior to isolation of the reaction product. This conversion can be accomplished by treatment of the reaction mixture with aqueous acid. Treatment of the reaction mixture with aqueous acid can be carried out by quenching the reaction mixture with dilute aqueous acid or by addition of acid to the process stream after quenching. Alternatively, the mixture of the iminobenzoxazine of Formula cyclo-1 and amide of Formula 1 can be isolated and this mixture can then be converted to the amide of Formula 1, for example by treatment with dilute aqueous acid, optionally in the presence of a suitable organic solvent.

In various embodiments of conditions of this process, the cyclization side reaction converting the desired product of Formula 1 to the Formula cyclo-1 compound usually occurs to only a minor extent, if at all, in which cases the suitable ratios of sulfonyl chloride and base are sufficient to complete the coupling reaction. However, for some pyrazolecarboxylic acids of Formula 2, anthranilic acids of Formula 3 (such as when $R^2$ is CN) and conditions of the reaction (e.g., using sterically hindered substituted pyridines such as 2,6-lutidine as bases), the conversion of the desired product of Formula 1 to the Formula cyclo-1 compound can occur to a more significant extent or can be the predominant reaction. In these cases, the use of larger ratios of sulfonyl chloride and required to complete the conversion. Completion of the coupling of the compound of Formula 2 and the compound of Formula 3 to form a compound of Formula 1 can be detected by analysis of the reaction mixture using any of a variety of methods that are generally known and available, including FTIR, HPLC and NMR. The analysis can be conducted by sampling the reaction mixture or portion thereof as it transits the reaction zone or a sampling loop. The ratio of the components of the mixture can be corrected by adjusting the amount of the appropriate component introduced to the reaction mixture by either adjusting the concentration of the component in the reaction flow or by adjusting the flow rate of its introduction.

Once the rates of combining a specific compound of Formula 2 and a specific compound of Formula 3 are optimized to form a specific compound of Formula 1 with high yield and/or purity, the rates of introduction of the compound of Formula 2, the compound of Formula 3, the sulfonyl chloride, and optional solvent and/or optional base (if present), and the rate of removal of the compound of Formula 1 from the reaction zone, may be held substantially constant during the duration of a continuous process run. One can appreciate that the rates of introduction and removal may be different when different compounds of Formula 1 are prepared.

A compound of Formula 1 wherein $R^1$ is H can be treated with a halogenating agent to provide a compound of Formula 1 wherein $R^1$ is Cl or Br. The reaction may be carried out by treating the compound of Formula 1 wherein $R^1$ is H with a halogenating agent such as chlorine or bromine, usually in the presence of a base and a solvent. The base may be selected from metal hydroxides such as sodium hydroxide, lithium hydroxide, potassium hydroxide and calcium hydroxide, alkali metal hydrides such as sodium hydride and potassium hydride, and alkali metal alkoxides such as sodium methoxide, sodium ethoxide and potassium tert-butoxide. The base can be used in an amount of from 0.8 to 5 times by mol, or from 1 to 3.5 times by mol, to the compound of the Formula 1. The solvent may be selected from ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; ketones such as acetone, methyl ethyl ketone and cyclohexanone; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone. The reaction can be carried out usually at from −20 to 120° C., or from 0 to 80° C., and the reaction time is usually from about 0.5 to about 48 hours, or from about 1 to about 24 hours. Representative halogenations are described in WO 2008/072745. Similarly, a compound of Formula 1 wherein $R^2$ is H can be treated with a halogenating agent to provide a compound of Formula 1 wherein $R^2$ is Cl or Br.

Pyrazolecarboxylic acids of Formula 2 can be prepared using methods of heterocyclic synthesis known in the literature, including references found in the following compendia: *Rodd's Chemistry of Chemistry of Carbon Compounds*, Vol. IVa to IVI, S. Coffey editor, Elsevier Scientific Publishing, New York, 1973; *Comprehensive Heterocyclic Chemistry*, Vol. 1-7, A. R. Katritzky and C. W. Rees editors, Pergamon Press, New York, 1984; *Comprehensive Heterocyclic Chemistry II*, Vol. 1-9, A. R. Katritzky, C. W. Rees, and E. F. Scriven editors, Pergamon Press, New York, 19%; and the series, *The Chemistry of Heterocyclic Compounds*, E. C. Taylor, editor, Wiley, New York. A variety of heterocyclic acids (including pyrazolecarboxylic acids) and general methods for their synthesis are found in PCT Patent Publications WO 98/57397.

One embodiment of a procedure for preparing pyrazolecarboxylic acids of Formula 2a is shown in Scheme 3.

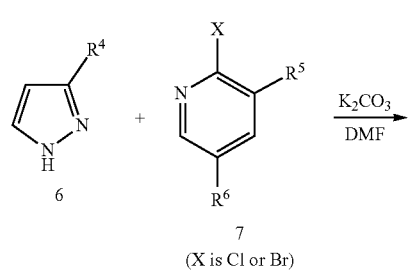

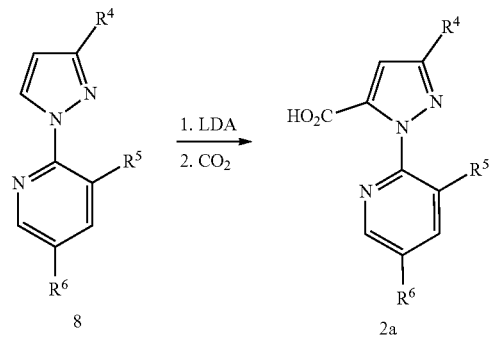

Reaction of a pyrazole of Formula 6 with a 2-halopyridine of Formula 7 affords good yields of the 1-pyridinylpyrazole of Formula 8 with good specificity for the desired regiochemistry. Metallation of the compound of Formula 8 with lithium diisopropylamide (LDA) followed by quenching of the lithium salt with carbon dioxide affords the 1-(2-pyridinyl)pyrazolecarboxylic acid of Formula 2a. For a leading reference to this method see PCT Patent Publication WO 03/015519.

As shown in Scheme 4, pyrazolecarboxylic acids of Formula 2b can be prepared via 3+2 cycloaddition of an appropriately substituted iminohalide of Formula 9 with either substituted propiolates of Formula 10 or acrylates of Formula 11.

Scheme 4

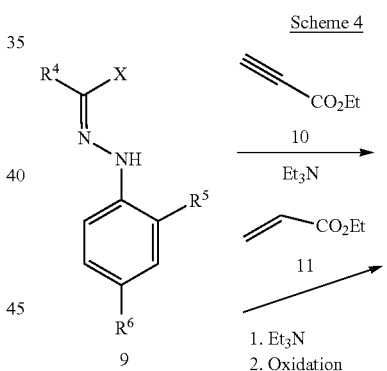

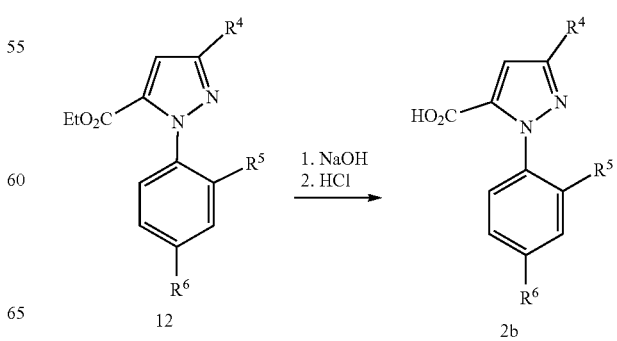

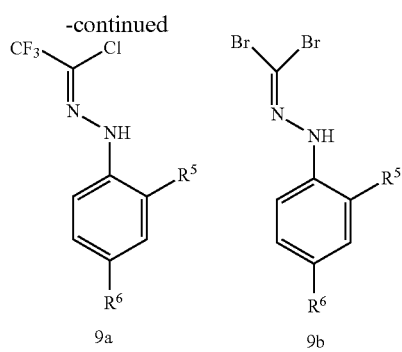

9a    9b

Cycloaddition with acrylates requires additional oxidation of the intermediate pyrazoline to the pyrazole. Hydrolysis of the ester of Formula 12 affords the pyrazolecarboxylic acids of Formula 2b. Suitable iminohalides for this reaction include the trifluoromethyl iminochloride of Formula 9a and the iminodibromide of Formula 9b. Compounds such as Formula 9a are known (*J. Heterocycl. Chem.* 1985, 22(2), 565-8). Other compounds of Formula 9 such as Formula 9b are available by known methods (*Tetrahedron Letters* 1999, 40, 2605).

Another method for preparation of pyrazolecarboxylic acids of Formula 2b is shown in Scheme 5.

Pyrazoles of Formula 13 can be condensed with aryl iodides using methods such as those reported by A. Klapars, J. C. Antilla, X. Huang and S. L. Buchwald, *J. Am. Chem. Soc.* 152001, 123, 7727-7729, or with aryl boronic acids using methods such as those reported by P. Y. S. Lam, C. G. Clark, S. Saubern, J. Adams, M. P. Winters, D. M. T. Chan and A. Combs, *Tetrahedron Len.* 1998, 39, 2941-2944. The resulting adducts of Formula 15 can be oxidized with oxidizing agents such as potassium permanganate to afford the pyrazolecarboxylic acids of Formula 2b.

The starting pyrazoles of Formulae 6 and 13 are known compounds or can be prepared according to known methods. For example, the pyrazole of Formula 6a (the compound of Formula 6 wherein $R^4$ is $CF_3$) can be prepared by literature procedures (*J. Fluorine Chem.* 1991, 53(1), 61-70). The pyrazoles of Formula 6b (compounds of Formula 6 wherein $R^4$ is Cl or Br) can be prepared by the procedure described in *Chem. Ber.* 1966, 99(10), 3350-7.

A useful alternative method for the preparation of a compound of Formula 6b is depicted in Scheme 6.

Scheme 6

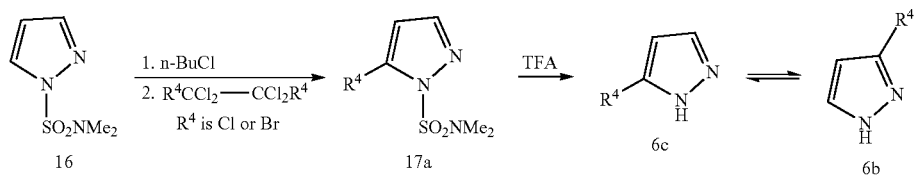

Metallation of the sulfamoylpyrazole of Formula 16 with n-butyllithium followed by direct halogenation of the anion with either hexachloroethane (for $R^4$ being Cl) or 1,2-dibromotetrachloroethane (for $R^4$ being Br) affords the halogenated derivatives of Formula 17a. Removal of the sulfamoyl group with trifluoroacetic acid (TFA) at room temperature proceeds cleanly and in good yield to afford the pyrazoles of Formula 6c. One of ordinary skill in the art will recognize that Formula 6c is a tautomer of Formula 6b.

Pyrazolecarboxylic acids 2 can also be prepared by oxidation of the pyrazoline of Formula 18 to give the pyrazole of Formula 19 followed by hydrolysis to the carboxylic acid as shown in Scheme 7.

Scheme 5

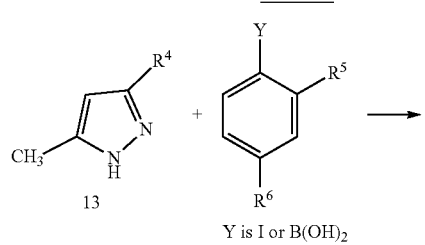

Y is I or B(OH)$_2$

14

Scheme 7

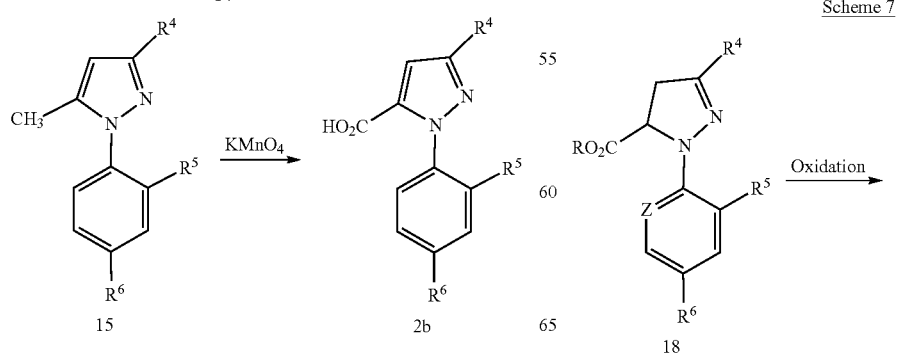

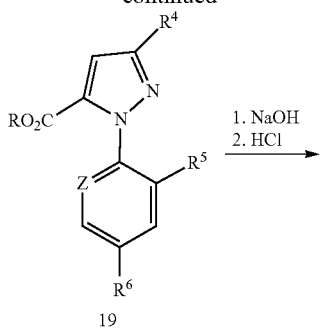

19

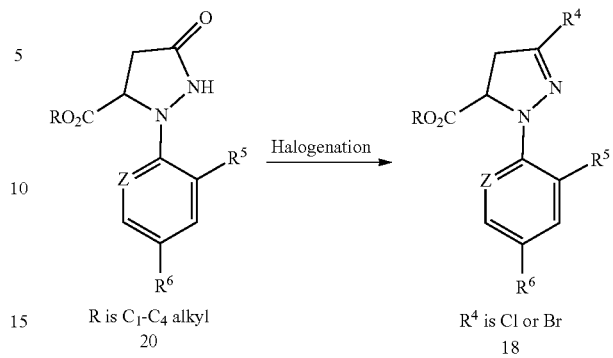

Scheme 8

R is $C_1$-$C_4$ alkyl
20

$R^4$ is Cl or Br
18

Halogenating reagents that can be used include phosphorus oxyhalides, phosphorus trihalides, phosphorus pentahalides, thionyl chloride, dihalotrialkylphophoranes, dihalotriphenylphosphoranes, oxalyl chloride and phosgene. In various embodiments, the halogenating reagents are phosphorus oxyhalides and phosphorus pentahalides. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option.

Alternatively, compounds of Formula 18 wherein $R^4$ is halogen can be prepared by treating the corresponding compounds of Formula 18 wherein $R^4$ is a different halogen (e.g., Cl for making Formula 18 wherein $R^4$ is Br) or a sulfonate group such as methanesulfonate, benzenesulfonate or p-toluenesulfonate, with hydrogen bromide or hydrogen chloride, respectively. By this method the $R^4$ halogen or sulfonate substituent on the Formula 18 starting compound is replaced with Br or Cl from hydrogen bromide or hydrogen chloride, respectively. Starting compounds of Formula 18 wherein $R^4$ is Cl or Br can be prepared from corresponding compounds of Formula 20 as already described. Starting compounds of Formula 18 wherein $R^4$ is a sulfonate group can likewise be prepared from corresponding compounds of Formula 20 by standard methods such as treatment with a sulfonyl chloride (e.g., methanesulfonyl chloride, benzenesulfonyl chloride, or p-toluenesulfonyl chloride) and a base such as a tertiary amine (e.g., triethylamine) in a suitable solvent such as dichloromethane.

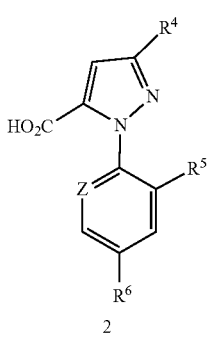

2

The oxidizing agent can be hydrogen peroxide, organic peroxides, potassium persulfate, sodium persulfate, ammonium persulfate, potassium monopersulfate (e.g., Oxone®) or potassium permanganate. This oxidation can be carried out in the presence of a solvent, including an ether, such as tetrahydrofuran, p-dioxane and the like, an organic ester, such as ethyl acetate, dimethyl carbonate and the like, or a polar aprotic organic such as N,N-dimethylformamide, acetonitrile and the like.

Halopyrazolines 18 wherein $R^4$ is Cl or Br can be prepared from pyrazolones of Formula 20 by treatment with an appropriate halogenating agent as shown in Scheme 8.

Pyrazolecarboxylic acids of Formula 2c wherein $R^4$ is $OCHF_2$ or $OCH_2CF_3$ can be prepared by the method outlined in Scheme 9.

Scheme 9

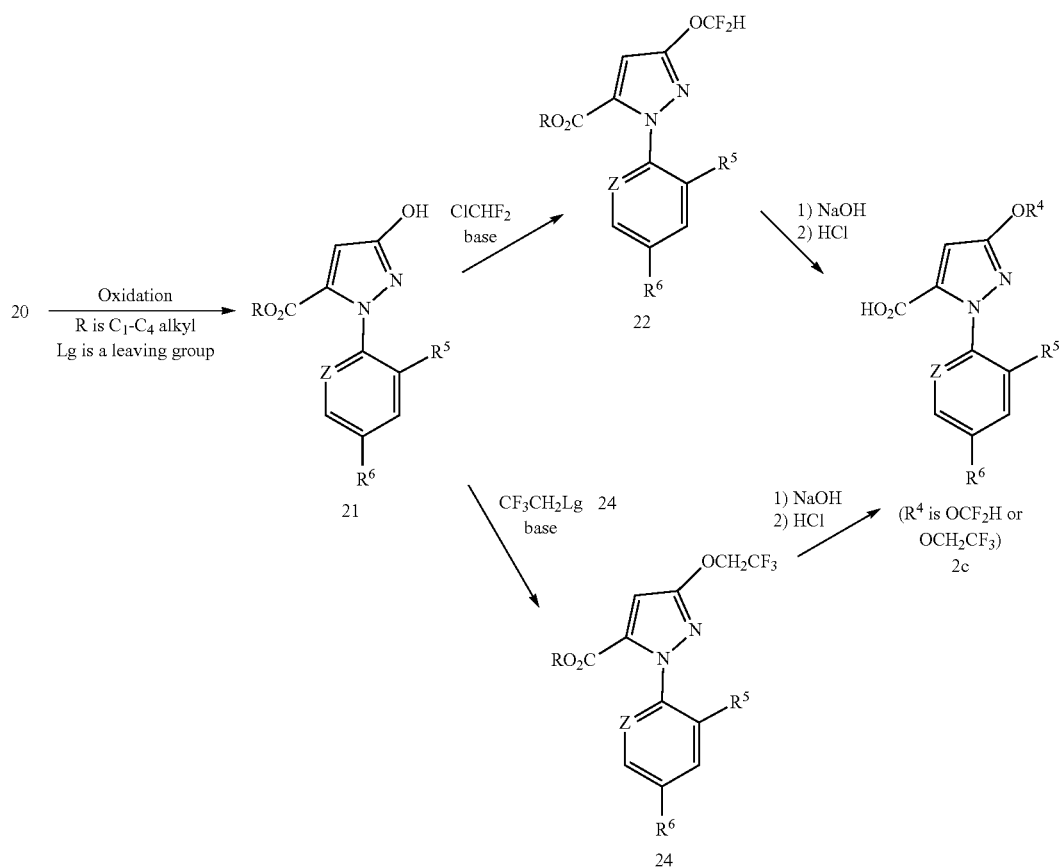

In this method, instead of being halogenated as shown in Scheme 8, the compound of Formula 20 is oxidized to the compound of Formula 21. The reaction conditions for this oxidation are as already described for the conversion of the compound of Formula 18 to the compound of Formula 19 in Scheme 7. The compound of Formula 21 can then be alkylated to form the compound of Formula 22 by contact with difluorocarbene, prepared in situ from $CHClF_2$ in the presence of a base. The compound of Formula 21 can also be alkylated to form the compound of Formula 24 by contact with an alkylating agent $CF_3CH_2Lg$ in the presence of a base. The alkylation reaction is generally conducted in a solvent, which can include ethers, such as tetrahydrofuran or dioxane, and polar aprotic solvents, such as acetonitrile, N,N-dimethylformamide, and the like. The base can be selected from inorganic bases such as potassium carbonate, sodium hydroxide or sodium hydride. In various embodiments, the reaction is conducted using potassium carbonate with N,N-dimethylformamide or acetonitrile as the solvent. In the alkylating agent $CF_3CH_2Lg$, Lg is a nucleofuge (i.e. leaving group) such as halogen (e.g., Br, I), $OS(O)_2CH_3$ (methanesulfonate), $OS(O)_2CF_3$, $OS(O)_2Ph$-p-$CH_3$ (p-toluenesulfonate), and the like. The product of Formula 22 can be isolated by conventional techniques such as extraction. The esters can then be converted to the carboxylic acids of Formula 2c by the methods already described for the conversion of Formula 12 to Formula 2b in Scheme 4.

Compounds of Formula 20 can be prepared from compounds of Formula 25 as outlined in Scheme 10.

Scheme 10

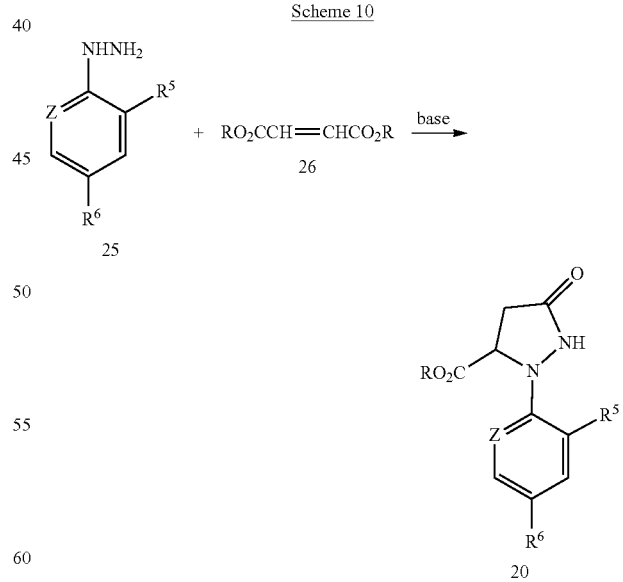

In this method, a hydrazine compound of Formula 25 is contacted with a compound of Formula 26 (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Polar protic and polar aprotic organic solvents can be used, such as alcohols, acetonitrile, tetrahydrofuran, N,N-dimethylformamide, dimethyl sulfoxide and the like. In various embodiments, the solvents are alcohols such as methanol and ethanol. In other embodiments, the alcohol corresponds to (i.e. be the same as that making up) the fumarate or maleate ester and the alkoxide base. Depending on the reaction conditions and the means of isolation, the —$CO_2R$ function on the compound of Formula 20 may be hydrolyzed to —$CO_2H$; for example, the presence of water in the reaction mixture can promote such hydrolysis. If the carboxylic acid (—$CO_2H$) is formed, it can be converted back to —$CO_2R$ wherein R is $C_1$-$C_4$ alkyl using esterification methods well known in the art. The desired product, a compound of Formula 20, can be isolated by methods known to those skilled in the art, such as crystallization, extraction or distillation.

Compounds of Formula 2d wherein $R^4$ is $C_1$-$C_4$ alkyl substituted with a 5- or 6-membered aromatic heterocycle substituted with Q can be prepared according to methods described in WO 2007/144100. Compounds of Formula 2e wherein $R^4$ is a $C_1$-$C_4$ alkyl substituted with a tetrazole optionally substituted with one or more substituents independently selected from the group consisting of halogen, $C_1$-$C_6$ alkyl, $C_3$-$C_6$ cycloalkyl and $C_1$-$C_6$ haloalkyl can be prepared according to methods described in WO 2010/069502.

As shown in Scheme 11, compounds of Formula 2e can be prepared, for example, by reacting pyrazolecarboxylic esters of Formula 27 in which Q, $R^5$ and $R^6$ have the meanings given above, R represents $C_1$-$C_4$ alkyl and $R^8$ represents H or $C_1$-$C_3$ alkyl, with an alkali metal hydroxide (for example sodium hydroxide or potassium hydroxide) in the presence of an inert diluent (for example dioxane/water or ethanol/water) followed by acidification. Pyrazolecarboxylic esters of Formula 27 can be prepared, for example, by reacting pyrazolecarboxylic ester derivatives of Formula 28 in which Q, R, $R^5$ and $R^6$ have the meanings given above and Z represents chlorine, bromine, iodine, methylsulfonyl or toluenesulfonyl, with a tetrazole of Formula 29 in which Q has the meaning given above, in the presence of a base (for example sodium hydroxide, potassium carbonate, sodium carbonate, cesium carbonate, sodium methoxide, triethylamine or sodium hydride) in the presence of a solvent (for example tetrahydrofuran, toluene, acetone, acetonitrile, methanol, dimethylformamide or dioxane). Representative procedures are disclosed in WO 2010/069502. Tetrazoles of Formula 29 are known, commercially available, or can be prepared by known processes (cf., for example, WO2004/020445; William P. Norris, J. Org. Chem., 1962, 27 (9), 3248-3251; Henry C. Brown, Robert J. Kassal, J. Org. Chem., 1967, 32 (6), 1871-1873; Dennis P. Curran, Sabine Hadida, Sun-Young Kim, Tetrahedron, 1999, 55 (29), 8997-9006; L. D. Hansen, E. J. Baca, P. Scheiner, Journal of Heterocyclic Chemistry, 1970, 7, 991-996). Alternatively, compounds of Formula 28a can be prepared from compounds of Formula 28 wherein Z is H by bromination or chlorination using active halogen compounds such as N-chlorosuccinimide or N-Bromosuccinimide in the presence of a radical initiator such as benzoyl peroxide or AIBN.

Representative procedures are disclosed in WO 2016014463, WO 2012112946 and WO 2016023832. Compounds of Formula 2f can be prepared from compounds of Formula 28a wherein Z is halogen by treatment with an alkali metal hydroxide (for example sodium hydroxide or potassium hydroxide) in the presence of an inert diluent (for example dioxane/water or ethanol/water).

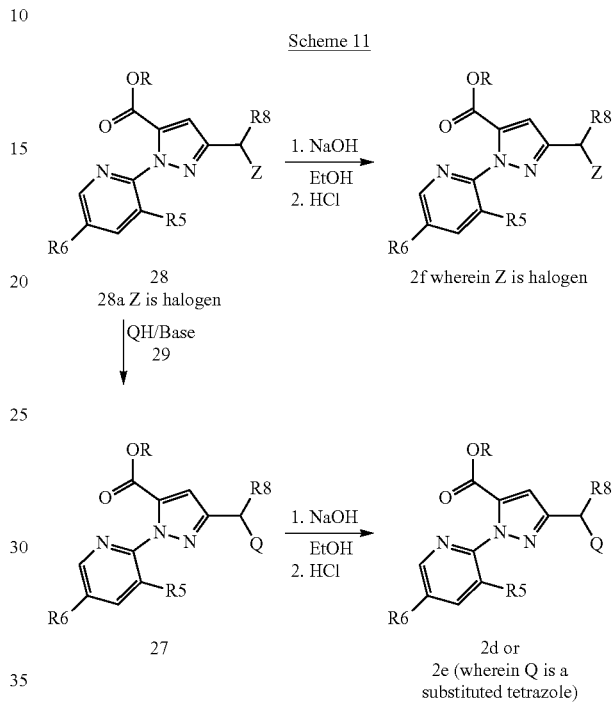

Scheme 11

As shown in Scheme 12, pyrazolecarboxylic esters of Formula 28 can be prepared, for example, by reacting alcohol derivatives of Formula 30 in which R, $R^5$, $R^6$ and $R^8$ have the meanings given above, with a sulfonyl chloride (for example methylsulfonyl chloride or toluenesulfonyl chloride) or a halogenating agent (for example thionyl chloride), if appropriate, in the presence of a solvent (for example dichloromethane) and, if appropriate, in the presence of a base (for example triethylamine or pyridine). Alcohol derivatives of Formula 30 can be prepared, for example, by reacting ketone derivatives of Formula 31 in which R, $R^5$, $R^6$ and $R^8$ have the meanings given above, with a suitable reducing agent (for example sodium borohydride) in the presence of a solvent (for example ethanol). Ketone derivatives of Formula 31 can be prepared, for example, by reacting pyrazole derivatives of Formula 32 in which R, $R^5$ and $R^6$ have the meanings given above and Y represents chlorine or bromine, with a tin derivative of Formula 33 in which $R^9$ represents H or $C_1$-$C_2$-alkyl in the presence of a transition metal (for example tetrakis(triphenylphosphine) palladium(0)) and a salt (for example lithium chloride) in the presence of a solvent (for example tetrahydrofuran). Tin derivatives of Formula 33 are known and/or commercially available. Pyrazole derivatives of the Formula 32 are known or can be obtained by known processes (see for example, WO2004/033468, WO2003/015518 and WO2003/016283).

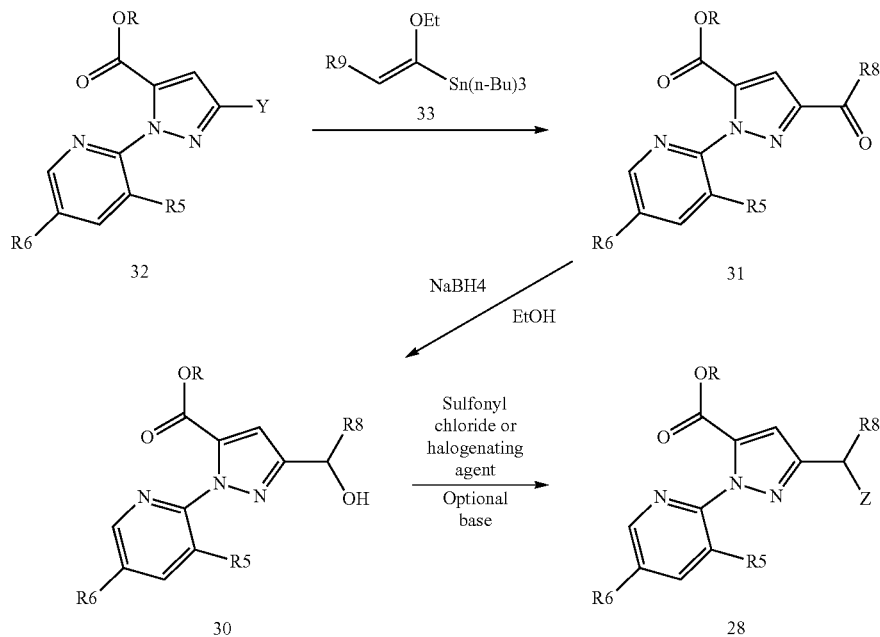

Scheme 12

Anilines of Formula 3a can be prepared from the reaction of isatoic anhydrides of Formula 34 with ammonia or alkylamines of formula 35, as shown in Scheme 13, by using procedures such as that described by L. H. Sternbach et al., *J. Org. Chem.* 1971, 36, 777-781.

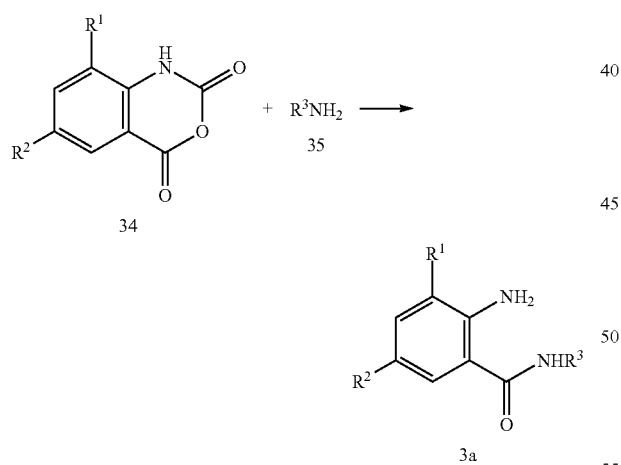

Scheme 13

Isatoic anhydrides of Formula 34 can be made by a variety of known methods that are well documented in the chemical literature. For example, isatoic anhydrides are available from the corresponding anthranilic acids via cyclization involving reaction of the anthranilic acid with phosgene or a phosgene equivalent. For leading references to the methods, see Coppola, *Synthesis* 1950, 505 and Fabis et al., *Tetrahedron*, 1995, 10789.

The synthesis of the isatoic anhydrides of Formula 34 can also be achieved from isatins of Formula 37 as outlined in Scheme 14.

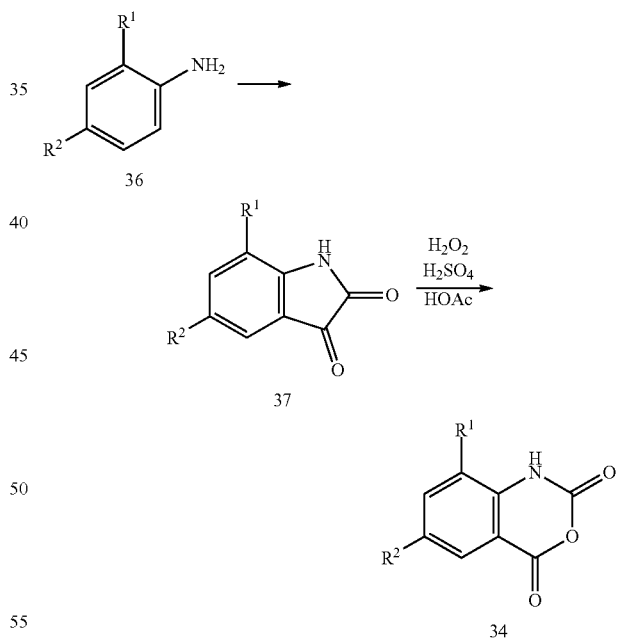

Scheme 14

Isatins of Formula 37 are available from aniline derivatives of Formula 36 following literature procedures such as F. D. Popp, *Adv. Heterocycl. Chem.* 1975, 18, 1-58 and J. F. M. Da Silva et al., *Journal of the Brazilian Chemical Society* 2001, 12(3), 273-324. Oxidation of isatin 30 with hydrogen peroxide generally affords good yields of the corresponding isatoic anhydride 28 (G. Reissenweber and D. Mangold, *Angew. Chem. Int. Ed Engl.* 1980, 19, 222-223).

As shown in Scheme 15, isatins of Formula 37 wherein $R^2$ is Cl, Br or I are also available from the 5-unsubstituted isatins of Formula 38 by halogenation. Cyanide displacement can then provide isatins of Formula 37a (Formula 37 where $R^2$ is CN).

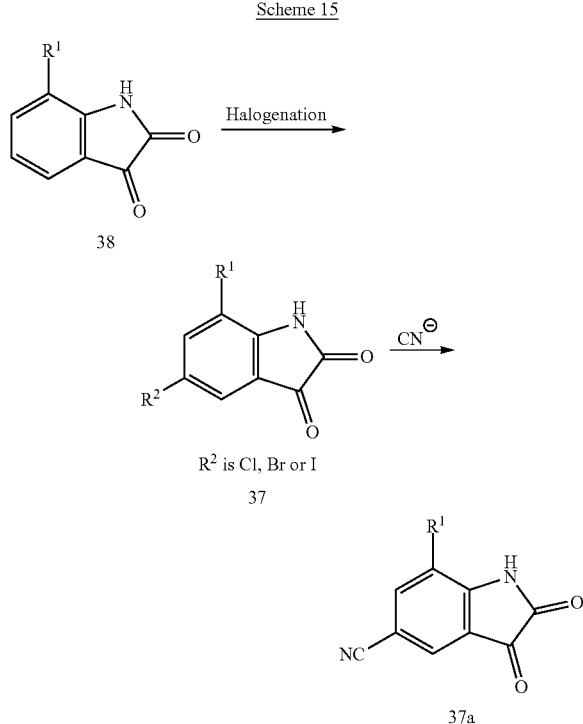

Scheme 15

38

37

$R^2$ is Cl, Br or I

37a

The halogenation reaction can be carried out using many reagents and procedures known in the literature. Suitable reagents include the elemental halogens (chlorine, bromine, or iodine), "positive-halogen" reagents such as trichloroisocyanuric acid, N-chlorosuccinimide (NCS), N-bromosuccinimide (NBS) or N-iodosuccinimide (NIS), and halogenating reagents such as the mixtures including hydrogen peroxide and a hydrogen halide. The halogen at the 5-position of isatins of Formula 37 wherein $R^2$ is Cl, Br or I can be displaced by cyanide using methods known in the literature. These methods include the use of a cyanide salt, usually employing a metal compound, and often in the presence of a ligand such as a substituted phosphine or a substituted bisphosphinoalkane. Suitable methods include those employing compounds of palladium such as those described by P. E. Maligres et al., *Tetrahedron Letters* 1999, 40, 8193-8195, and by M. Beller et al., *Chem. Eur. J.* 2003, 9(8), 1828-1836; those employing compounds of copper such as those described by S. L. Buchwald in *J. Am. Chem. Soc.* 2003, 125, 2890-2891; and those employing compounds of nickel such as those described in European Patent 384392, and by K. Sasaki in *Bull. Chem. Soc. Japan* 2004, 77, 1013-1019, and by R. K. Arvela and N. E. Leadbeater in *J. Org. Chem.* 2003, 68, 9122-9125. One versed in the art will appreciate that when $R^1$ is Cl, $R^2$ of Formula 27 may be Br or I to obtain selectivity in the cyanation (i.e. displacement of halogen by cyanide).

As shown in Scheme 16, anilines of Formula 3a are typically available from the corresponding 2-nitrobenzoic acids (or esters) of Formula 32 via catalytic hydrogenation of the nitro group followed by reaction of the anthranilic ester of Formula 33 with ammonia or an alkylamine.

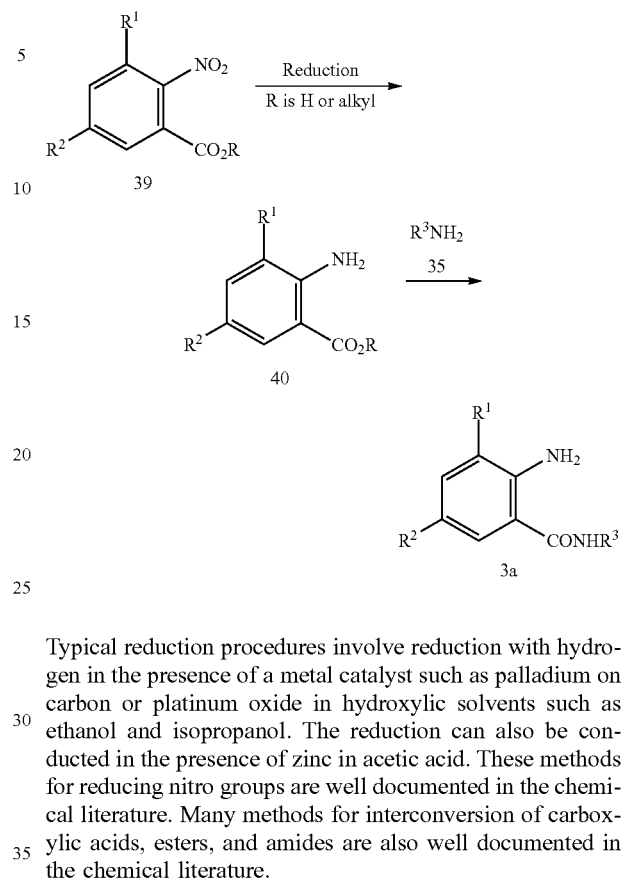

Scheme 16

39

40

3a

Typical reduction procedures involve reduction with hydrogen in the presence of a metal catalyst such as palladium on carbon or platinum oxide in hydroxylic solvents such as ethanol and isopropanol. The reduction can also be conducted in the presence of zinc in acetic acid. These methods for reducing nitro groups are well documented in the chemical literature. Many methods for interconversion of carboxylic acids, esters, and amides are also well documented in the chemical literature.

As shown in Scheme 17, anilines of Formula 3a are also available from the 5-unsubstituted anilines of Formula 41 by halogenation to provide anilines of Formula 3a wherein $R^2$ is Br, Cl or I, optionally followed by cyanide displacement to provide anilines of Formula 3c (Formula 3 where $R^2$ is CN).

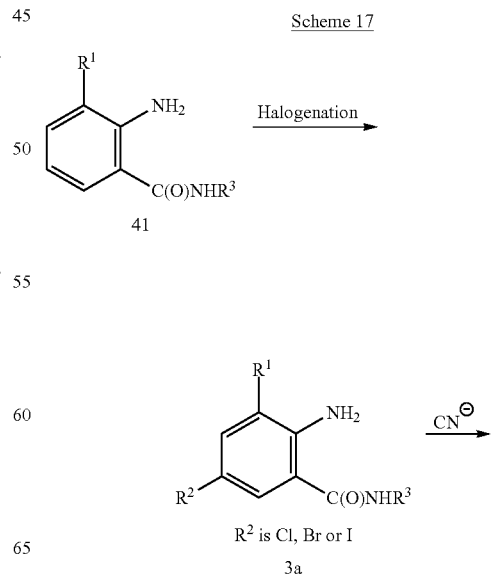

Scheme 17

41

$R^2$ is Cl, Br or I

3a

-continued

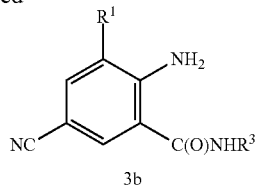
3b

Suitable methods and procedures are known in the literature and are similar to those described for the halogenations and cyanide displacements shown in Scheme 13. One skilled in the art will recognize that the halogenation and cyanation can also be carried out at other stages in the preparation of anilines of Formula 3.

Thioamides of formula 3c can be prepared by thionation of their amide analogs 3a (Scheme 18). Methods can be classified as either proceeding through direct treatment of the amide with the thionating reagent or by prior activation of the amide with an electrophilic reagent. Methods employing the former strategy include treatment of the amide with $P_4S_{10}$, either with or without additives, and use of diethylthiocarbamoyl chloride, ethylaluminum sulfide, boron sulfide, or Lawesson's reagent. A polymer-supported thionating reagent prepared from a commercially available diamine resin and ethyl dichlorothiophosphate has also recently been disclosed along with procedures involving microwave irradiation. Methods that proceed through prior activation of the amide include combinations of oxalyl chloride or phosphorus oxychloride with benzyltriethylammonium tetrathiomolybdate, phosphorus oxychloride with hexamethyldisilathiane, and trialkyloxonium tetrafluoroborates with sodium hydrosulfide and reaction of aqueous ammonium sulfide with pyridinium salts generated from the treatment of amides with pyridine and triflic anhydride. See Brillon, D. *Sulfur Rep.* 1992, 12, 297; Hartke, K.; Gerber, H.-D. *J. Prakt. Chem.* 1996, 338, 763; Raucher, S.; Klein, P. *J. Org. Chem.* 1981, 46, 3558; Scheeren, J. W.; Ooms, P. H. J.; Nivard, R. J. F. *Synthesis* 1973, 149; Brillon, D. *Synth. Commun.* 1990, 20, 3085; Goel, O. P.; Krolls, U. *Synthesis* 1987, 162; Curphey, T. J. J. *Org. Chem.* 2002, 67, 6461; Ogata, M.; Matsumoto, H. *Heterocycles* 1978, 11, 139; Hirabayashi, T.; Inoue, K.; Yokota, K. *J. Organomet. Chem.* 1975, 92, 139; Steliou, K.; Mrani, M. *J. Am. Chem. Soc.* 1982, 104, 3104; Wojtkowski, P. W.; Dolfini, J. E.; Kocy, O.; Cimarusti, C. M. *J. Am. Chem. Soc.* 1975, 97, 5628; Cava, M. P.; Levinson, M. I. *Tetrahedron* 1985, 41, 5061; Ley, S. V.; Leach, A. G.; Storer, R. I. *J. Chem. Soc., Perkin Trans.* 1 2001, 358; Varma, R. S.; Kumar, D. *Org. Lett.* 1999, 1, 697; Ilankumaran, P.; Ramesha, A. R.; Chandrasekaran, S. *Tetrahedron Lett.* 1995, 36, 8311; Smith, D. C.; Lee, S. W.; Fuchs, P. L. *J. Org. Chem.* 1994, 59, 348; Bodine, J. J.; Kaloustian, M. *Synth. Commun.* 1982, 12, 787 and Charette, A. B., Grenon. M., *J. Org. Chem.* 2003, 68, 5792-5794.

Scheme 18

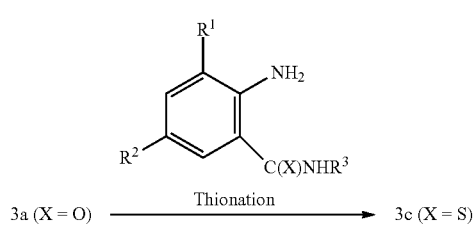

Compounds of Formula 1a wherein $R^4$ is $CH_2R^8$ (a subset of $R^4$ is $C_1$-$C_4$ alkyl) can be prepared using the continuous process from a compound of Formula 2 wherein $R^4$ is $CH_2R^8$, wherein $R^8$ is as previously defined with a suitable compound of Formula 3. As shown in Scheme 19, the compound of Formula 1a can be converted to a compound of 1b by halogenation as described above for a compound of Formula 28a. Alternatively, a compound of Formula 28b wherein R is H and Z is Cl or Br can be combined with a compound of Formula 2 using the continuous process to provide the compound of Formula 1b. The compound of Formula 1b can be treated with a tetrazole of Formula 29 to provide a compound of Formula 1c.

Scheme 19

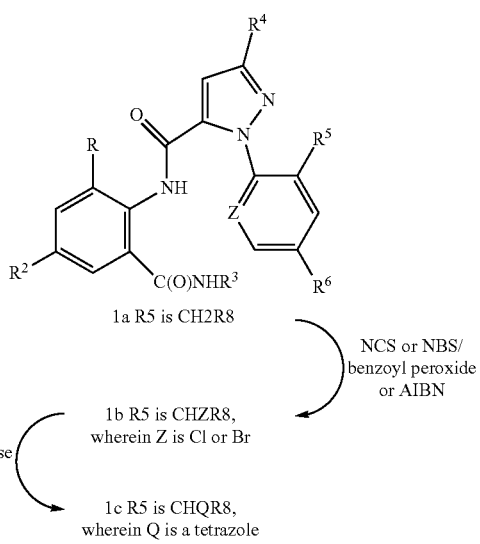

It is recognized that some reagents and reaction conditions described above for preparing compounds of Formulae 2 and 3 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formulae 2 and 3. One skilled in the art will also recognize that it may be necessary to perform a combination of the steps illustrated in the above schemes in an order other than that implied by the particular sequence presented to prepare the compounds of Formulae 2 and 3. One skilled in the art will also recognize that compounds of Formulae 2 and 3 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the method(s) of the present disclosure to its fullest extent. The following Examples are, therefore, to be construed as merely illustrative and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s is singlet, d is doublet, and m is multiplet. Quantitative HPLC of the product was performed using an Ace C18 or C4 Ultra Inert® chromatography column (reversed phase column manufactured by MacMod Analytical Inc., Chadds Ford, Pa. 19317) (3 µm particle size, 4.6 mm×15 cm, eluent 5-80% acetonitrile/pH 3 phosphate buffer).

Example 1

Preparation of 3-bromo-N-[4-chloro-2-methyl-6-[(methylamino)carbonyl]phenyl]-1-(3-chloro-2-pyridinyl)-1H-pyrazole-5-carboxamide Using a 2-Stage CSTR Reaction Zone Followed by a 1-Stage CSTR Quench Zone at Room Temperature Acetonitrile (262 g), 3-bromo-1-(3-chloro-2-pyridinyl)-1H-pyrazole-5-carboxylic acid (230 g, 0.8 mol), prepared as in PCT Patent Publication WO 2003/015519, and 2-amino-5-chloro-N,3-dimethylbenzamide (152 g, 0.77 mol), prepared as in PCT Patent Publication WO 2006/062978, and 3-picoline (180 g, 2 mol) were mixed together in a jacketed, agitated vessel. The mixture was heated until all the solids dissolved. This solution was then pumped continuously into Reactor 1 (Reaction Zone 1), a 200-mL jacketed, agitated vessel at a rate of 1.7 g/min. In addition, methanesulfonyl chloride was pumped into Reactor 1 at a rate of 0.21 g/min. The volume level in Reactor 1 was controlled at 100 mL and the temperature was maintained at 25° C. The contents of Reactor 1 were fed into Reactor 2 (Reaction Zone 2) at an average rate of 1.9 g/min. Reactor 2 was a 200-mL jacketed, agitated vessel, where the temperature was maintained at 25° C. and the level controlled at 100 mL. Material from Reactor 2 was pumped to Reactor 3 (Quench Zone) at an average rate of 1.9 g/min, and water was also pumped to Reactor 3 at an average of rate of 0.23 g/min. Reactor 3 was a 200-mL, jacketed, agitated vessel, where the temperature was maintained at 25° C. and the level at 100-mL. Product was taken out of reactor 3 at a continuous rate, where it was filtered. The recovered solids were washed with 5:1 acetonitrile:water, then with acetonitrile, and dried under nitrogen to afford the title compound as a light tan powder. Product purity was 98.6 wt % and yield was greater than 90%. Overall cake resistance was 6.7×10$^8$ ft/lb, compared with 15.9×10$^8$ ft/lb for a typical batch process.
$^1$H NMR (CDCl$_3$) δ 2.18 (s, 3H), 2.95 (s, 3H), 6.21 (m, 1H), 7.10 (s, 1H), 7.24 (m, 2H), 7.39 (m, 1H), 7.80 (d, 1H), 8.45 (d, 1H).

Example 2

Preparation of 3-bromo-N-[4-chloro-2-methyl-6-[(methylamino)carbonyl]phenyl]-1-(3-chloro-2-pyridinyl)-1H-pyrazole-5-carboxamide Using 2 CSTRs at Different Temperatures for the Reaction Zone Followed by a Single CSTR Quench Zone Acetonitrile (420 g), 3-bromo-1-(3-chloro-2-pyridinyl)-1H-pyrazole-5-carboxylic acid (249 g, 0.82 mol), prepared as in PCT Patent Publication WO 2003/015519, and 2-amino-5-chloro-N,3-dimethylbenzamide (168 g, 0.85 mol), prepared as in PCT Patent Publication WO 2006/062978, and 3-picoline (200 g, 2.14 mol) were mixed together in a jacketed, agitated vessel. The mixture was heated until all the solids dissolved. This solution was then pumped continuously into Reactor 1 (Reaction Zone 1), a 200-mL jacketed, agitated vessel at a rate of 1.4 g/min. In addition, methanesulfonyl chloride was pumped into Reactor 1 at a rate of 0.15 g/min. The volume level in Reactor 1 was controlled at 100 mL and the temperature was maintained at 50° C. The contents of Reactor 1 were fed into Reactor 2 (Reaction Zone 1) at an average rate of 1.55 g/min. Reactor 2 was a 200-mL jacketed, agitated vessel, where the temperature was maintained at 25° C. and the level controlled at 100 mL. Material from Reactor 2 was pumped to Reactor 3 (Quench Zone) at an average rate of 1.55 g/min, and water was also pumped to Reactor 3 at an average of rate of 0.17-g/min. Reactor 3 was a 200-mL, jacketed, agitated vessel, where the temperature was maintained at 25° C. and the level at 100-mL. Product was taken out of reactor 3 at a continuous rate, where it was filtered. The recovered solids were washed with 5:1 acetonitrile:water, then with acetonitrile, and dried under nitrogen to afford the title compound as a light tan powder. Product purity was 98.8 wt % and yield was greater than 90%. Overall cake resistance was 7.0×10$^8$ ft/lb, compared with 15.9×10$^8$ ft/lb for a typical batch process.
$^1$H NMR (CDCl$_3$) δ 2.18 (s, 3H), 2.95 (s, 3H), 6.21 (m, 1H), 7.10 (s, 1H), 7.24 (m, 2H), 7.39 (m, 1H), 7.80 (d, 1H), 8.45 (d, 1H).

Example 3

Preparation of 3-bromo-N-[4-chloro-2-methyl-6-[(methylamino)carbonyl]phenyl]-1-(3-chloro-2-pyridinyl)-1H-pyrazole-5-carboxamide Using a 2 CSTR Reaction Zone with a 12-Min Residence Time Followed by a Single CSTR Quench Zone Acetonitrile (532 g), 3-bromo-1-(3-chloro-2-pyridinyl)-1H-pyrazole-5-carboxylic acid (79 g, 0.26 mol), prepared as in PCT Patent Publication WO 2003/015519, and 2-amino-5-chloro-N,3-dimethylbenzamide (53 g, 0.27 mol), i.e. prepared as in PCT Patent Publication WO 2006/062978, and 3-picoline (63 g, 0.68 mol) were mixed together in a jacketed, agitated vessel. The mixture was heated until all the solids dissolved. This solution was then pumped continuously into Reactor 1 (Reaction Zone 1), a 200-mL jacketed, agitated vessel at a rate of 8.09 g/min. In addition, methanesulfonyl chloride was pumped into Reactor 1 at a rate of 0.40 g/min. The volume level in Reactor 1 was controlled at 100 mL and the temperature was maintained at 25° C. The contents of Reactor 1 were fed into Reactor 2 (Reaction Zone 1) at an average rate of 8.49 g/min. Reactor 2 was a 200-mL jacketed, agitated vessel, where the temperature was maintained at 25° C. and the level controlled at 100 mL. Material from Reactor 2 was pumped to Reactor 3 (Quench Zone) at an average rate of 8.49 g/min, and water was also pumped to Reactor 3 at an average of rate of 3.19 g/min. Reactor 3 was a 200-mL, jacketed, agitated vessel, where the temperature was maintained at 25° C. and the level at 150-mL. Product was taken out of reactor 3 at a continuous rate, where it was filtered. The recovered solids were washed with 5:1 acetonitrile:water, then with acetonitrile, and dried under nitrogen to afford the title compound as a light tan powder. Product purity was 98.5 wt % and yield was greater than 90%.

$^1$H NMR (CDCl$_3$) δ 2.18 (s, 3H), 2.95 (s, 3H), 6.21 (m, 1H), 7.10 (s, 1H), 7.24 (m, 2H), 7.39 (m, 1H), 7.80 (d, 1H), 8.45 (d, 1H).

Example 4

Preparation of 3-bromo-N-[4-chloro-2-methyl-6-[(methylamino)carbonyl]phenyl]-1-(3-chloro-2-pyridinyl)-1H-pyrazole-5-carboxamide Using a 2 CSTR Reaction Zone with a 2.5-Min Residence Time Followed by a Single CSTR Quench Zone Acetonitrile (1506 g), 3-bromo-1-(3-chloro-2-pyridinyl)-1H-pyrazole-5-carboxylic acid (175 g, 0.58 mol), prepared as in PCT Patent Publication WO 2003/015519, and 2-amino-5-chloro-N,3-dimethylbenzamide (119 g, 0.60 mol), prepared as in PCT Patent Publication WO 2006/062978, and 3-picoline (140 g, 1.51 mol) were mixed together in a jacketed, agitated vessel. The mixture was heated until all the solids dissolved. This solution was then pumped continuously into Reactor 1 (Reaction Zone 1), a 200-mL jacketed, agitated vessel at a rate of 32 g/min. In addition, methanesulfonyl chloride was pumped into Reactor 1 at a rate of 1.6 g/min. The volume level in Reactor 1 was controlled at 100 mL and the temperature was maintained at 35° C. The contents of Reactor 1 were fed into Reactor 2 (Reaction Zone 1) at an average rate of 51 g/min. Reactor 2 was a 200-mL jacketed, agitated vessel, where the temperature was maintained at 25° C. and the level controlled at 100 mL. Material from Reactor 2 was pumped to Reactor 3 (Quench Zone) at an average rate of 51 g/min, and water was also pumped to Reactor 3 at an average of rate of 13-g/min. Reactor 3 was a 200-mL, jacketed, agitated vessel, where the temperature was maintained at 25° C. and the level at 150-mL. Product was taken out of reactor 3 at a continuous rate, where it was filtered. The recovered solids were washed with 5:1 acetonitrile:water, then with acetonitrile, and dried under nitrogen to afford the title compound as a light tan powder. Product purity was 98.56 wt %.

$^1$H NMR (CDCl$_3$) δ 2.18 (s, 3H), 2.95 (s, 3H), 6.21 (m, 1H), 7.10 (s, 1H), 7.24 (m, 2H), 7.39 (m, 1H), 7.80 (d, 1H), 8.45 (d, 1H).

Example 5

Preparation of 3-bromo-1-(3-chloro-2-pyridinyl)-N-[4-cyano-2-methyl-6-[(methylamino)carbonyl]phenyl]-1H-pyrazole-5-carboxamide Using a 2 CSTR Reaction Zone Followed by a Single CSTR Quench Zone Acetonitrile (609 g), 3-bromo-1-(3-chloro-2-pyridinyl)-1H-pyrazole-5-carboxylic acid (36 g, 0.12 mol), prepared as in PCT Patent Publication WO 2003/015519, and 2-amino-5-cyano-N,3-dimethylbenzamide (24 g, 0.13 mol), and 3-picoline (33 g, 0.36 mol) were mixed together in a jacketed, agitated vessel. The mixture was heated until all the solids dissolved. This solution was then pumped continuously into Reactor 1 (Reaction Zone 1), a 200-mL jacketed, agitated vessel at a rate of 2.0 g/min. In addition, methanesulfonyl chloride was pumped into Reactor 1 at a rate of 0.05 g/min. The volume level in Reactor 1 was controlled at 130 mL and the temperature was maintained at 25° C. The contents of Reactor 1 were fed into Reactor 2 (Reaction Zone 1) at an average rate of 2.1 g/min. Reactor 2 was a 200-mL jacketed, agitated vessel, where the temperature was maintained at 25° C. and the level controlled at 130 mL. Material from Reactor 2 was pumped to Reactor 3 (Quench Zone) at an average rate of 2.1 g/min, and acidic water was also pumped to Reactor 3 at an average of rate of 0.21-g/min. Reactor 3 was a 200-mL, jacketed, agitated vessel, where the temperature was maintained at 25° C. and the level at 170-mL. Product was taken out of reactor 3 at a continuous rate, where it was neutralized with sodium hydroxide and filtered. The recovered solids were washed with 5:1 acetonitrile:water, then with acetonitrile, and dried under nitrogen to afford the title compound as a light tan powder. Product purity was 94.7 area %.

Example 6

Preparation of 3-bromo-N-[4-chloro-2-methyl-6-[(methylamino)carbonyl]phenyl]-1-(3-chloro-2-pyridinyl)-1H-pyrazole-5-carboxamide: Slurry Feed Using a 2 CSTR Reaction Zone with 2 MSC Feeds Followed by a Single CSTR Quench Zone Acetonitrile (420 g), 3-bromo-1-(3-chloro-2-pyridinyl)-1H-pyrazole-5-carboxylic acid (249 g, 0.82 mol), prepared as in PCT Patent Publication WO 2003/015519, and 2-amino-5-chloro-N,3-dimethylbenzamide (168 g, 0.85 mol), prepared as in PCT Patent Publication WO 2006/062978, and 3-picoline (200 g, 2.14 mol) are mixed together in a jacketed, agitated vessel at room temperature. This slurry is then pumped continuously into Reactor 1 (Reaction Zone 1), a 200-mL jacketed, agitated vessel at a rate of 1.4 g/min. In addition, methanesulfonyl chloride is pumped into Reactor 1 at a rate of 0.08 g/min. The volume level in Reactor 1 is controlled at 100 mL and the temperature is maintained at 25° C. The contents of Reactor 1 are fed into Reactor 2 (Reaction Zone 1) at an average rate of 1.48 g/min. In addition, a stream of methanesulfonyl chloride is pumped into Reactor 2 at a rate of 0.07-gmin. Reactor 2 is a 200-mL jacketed, agitated vessel, where the temperature was maintained at 25° C. and the level controlled at 200 mL. Material from Reactor 2 is pumped to Reactor 3 (Quench Zone) at an average rate of 1.55 g/min, and water is also pumped to Reactor 3 at an average of rate of 0.17-g/min. Reactor 3 is a 200-mL, jacketed, agitated vessel, where the temperature is maintained at 25° C. and the level at 50-mL. Product is taken out of reactor 3 at a continuous rate, where it is filtered. The recovered solids are washed with 5:1 acetonitrile:water, then with acetonitrile, and dried under nitrogen to afford the title compound as a light tan powder.

Example 7

Preparation of 3-bromo-N-[4-chloro-2-methyl-6-[(methylamino)carbonyl]phenyl]-1-(3-chloro-2-pyridinyl)-1H-pyrazole-5-carboxamide: Using a PFR and CSTR Combination Reaction Zone Followed by a Single CSTR Quench Zone Acetonitrile (420 g), 3-bromo-1-(3-chloro-2-pyridinyl)-1H-pyrazole-5-carboxylic acid (249 g, 0.82 mol), prepared as in PCT Patent Publication WO 2003/015519, and 2-amino-5-chloro-N,3-dimethylbenzamide (168 g, 0.85 mol), prepared as in PCT Patent Publication WO 2006/062978, and 3-picoline (200 g, 2.14 mol) are mixed together in a jacketed, agitated vessel at room temperature. This slurry is then pumped continuously into Reactor 1 (Reaction Zone 1), a 17-mL jacketed plug flow reactor with internal mixing zones, at a rate of 4.2 g/min. In addition, methanesulfonyl chloride is co-fed into Reactor 1 at a rate of 0.45 g/min. The temperature of Reactor 1 is maintained at 70° C., and the outlet of the reactor is fed into Reactor 2 (Reaction Zone 2) at an average rate of 4.65 g/min. Reactor 2 is a 200-mL jacketed, agitated vessel, where the temperature was maintained at 50° C. and the level controlled at 50 mL. Material from Reactor 2 is pumped to Reactor 3 (Quench Zone) at an average rate of 4.65 g/min, and water is also pumped to Reactor 3 at an average of rate of 0.61-g/min. Reactor 3 is a 200-mL, jacketed, agitated vessel, where the temperature is maintained at 25° C. and the level at 200-mL. Product is taken out of reactor 3 at a continuous rate, where it is filtered. The recovered solids are washed with 5:1 acetonitrile:water, then with acetonitrile, and dried under nitrogen to afford the title compound as a light tan powder.

Example 8

Preparation of 3-bromo-N-[4-chloro-2-methyl-6-[(methylamino)carbonyl]phenyl]-1-(3-chloro-2-pyridinyl)-1H-pyrazole-5-carboxamide: Using a Single CSTR Reaction Zone Followed by a Single CSTR Quench Zone Acetonitrile (420 g), 3-bromo-1-(3-chloro-2-pyridinyl)-1H-pyrazole-5-carboxylic acid (249 g, 0.82 mol), prepared as in PCT Patent Publication WO 2003/015519, and 2-amino-5-chloro-N,3-dimethylbenzamide (168 g, 0.85 mol), prepared as in PCT Patent Publication WO 2006/062978, and 3-picoline (200 g, 2.14 mol) are mixed together in a jacketed, agitated vessel at room temperature. This slurry is then pumped continuously into Reactor 1 (Reaction Zone), a 200-mL jacketed, agitated vessel at a rate of 1.4 g/min. In addition, methanesulfonyl chloride is pumped into Reactor 1 at a rate of 0.15 g/min. The volume level in Reactor 1 is controlled at 100 mL and the temperature is maintained at 25° C. The contents of Reactor 1 are fed into Reactor 2 (Quench Zone) at an average rate of 1.55 g/min, and water is also pumped to Reactor 2 at an average of rate of 0.17-g/min. Reactor 2 is a 200-mL, jacketed, agitated vessel, where the temperature is maintained at 10° C. and the level at 100-mL. Product is taken out of Reactor 2 at a continuous rate, where it is filtered. The recovered solids are washed with 5:1 acetonitrile:water, then with acetonitrile, and dried under nitrogen to afford the title compound as a light tan powder.

Using procedures similar to those in Examples 1-8, a compound of Formula 2, wherein Z is N, $R^4$ is $CH_2(5\text{-}CF_3\text{-}2H\text{-tetrazol-2-yl})$, $R^5$ is Cl and $R^6$ is H, and a compound of Formula 3 wherein X is O, $R^1$ is $CH_3$, $R^2$ is CN and $R^3$ is methyl are combined in a continuous process to prepare a compound of Formula 1 wherein X is O, Z is N, $R^1$ is $CH_3$, $R^2$ is CN, $R^3$ is methyl, $R^4$ is $CH_2(5\text{-}CF_3\text{-}2H\text{-tetrazol-2-yl})$, $R^5$ is Cl and $R^6$ is H (i.e. 1-(3-chloro-2-pyridinyl)-N-[4-cyano-2-methyl-6-[(methylamino)carbonyl]phenyl]-3-[[5-(trifluoromethyl)-2H-tetrazol-2-yl]methyl]-1H-pyrazole-5-carboxamide.

Using procedures similar to those in Examples 1-8, a compound of Formula 2, wherein Z is N, $R^4$ is Br, $R^5$ is $C_1$ and $R^6$ is H, and a compound of Formula 3 wherein X is O, $R^1$ is Br, $R^2$ is Cl and $R^3$ is 1-cyclopropylethyl are combined in a continuous process to prepare a compound of Formula 1 wherein X is O, Z is N, $R^1$ is Br, $R^2$ is Cl, $R^3$ is 1-cyclopropylethyl, $R^4$ is Br, $R^5$ is $C_1$ and $R^6$ is H (i.e. 3-bromo-N-[2-bromo-4-chloro-6-[[(1-cyclopropylethyl)amino]carbonyl]phenyl]-1-(3-chloro-2-pyridinyl)-1H-pyrazole-5-carboxamide).

By the procedures described herein together with methods known in the art, the following compounds of Tables 1 through 227 can be prepared and used in the method of the present disclosure. The following abbreviations are used in the Tables which follow: t means tertiary, s means secondary, n means normal, i means iso, Me means methyl, Et means ethyl, Pr means propyl, i-Pr means isopropyl, c-Pr means cyclopropyl and Bu means butyl.

TABLE 1

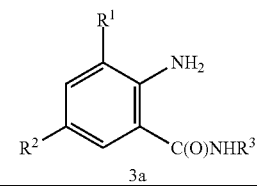

3a

| $R^1$ | $R^2$ | $R^3$ | $R^1$ | $R^2$ | $R^3$ | $R^1$ | $R^2$ | $R^3$ |
|---|---|---|---|---|---|---|---|---|
| $CH_3$ | Cl | H | $CH_3$ | CN | H | Cl | CN | H |
| $CH_3$ | Cl | Me | $CH_3$ | CN | Me | Cl | CN | Me |
| $CH_3$ | Cl | Et | $CH_3$ | CN | Et | Cl | CN | Et |
| $CH_3$ | Cl | i-Pr | $CH_3$ | CN | i-Pr | Cl | CN | i-Pr |
| $CH_3$ | Cl | t-Bu | $CH_3$ | CN | t-Bu | Cl | CN | t-Bu |
| $CH_3$ | Cl | n-Pr | $CH_3$ | CN | n-Pr | Cl | CN | n-Pr |
| $CH_3$ | Cl | n-Bu | $CH_3$ | CN | n-Bu | Cl | CN | n-Bu |
| $CH_3$ | Cl | s-Bu | $CH_3$ | CN | s-Bu | Cl | CN | s-Bu |
| $CH_3$ | Cl | i-Bu | $CH_3$ | CN | i-Bu | Cl | CN | i-Bu |
| $CH_3$ | Cl | $CH_2$-c-Pr | $CH_3$ | CN | $CH_2$-c-Pr | Cl | CN | $CH_2$-c-Pr |
| $CH_3$ | Cl | CH(Me)-c-Pr | $CH_3$ | CN | CH(Me)-c-Pr | Cl | CN | CH(Me)-c-Pr |
| $CH_3$ | Br | H | Cl | Cl | H | Br | Cl | H |
| $CH_3$ | Br | Me | Cl | Cl | Me | Br | Cl | Me |
| $CH_3$ | Br | Et | Cl | Cl | Et | Br | Cl | Et |
| $CH_3$ | Br | i-Pr | Cl | Cl | i-Pr | Br | Cl | i-Pr |
| $CH_3$ | Br | t-Bu | Cl | Cl | t-Bu | Br | Cl | t-Bu |
| $CH_3$ | Br | n-Pr | Cl | Cl | n-Pr | Br | Cl | n-Pr |
| $CH_3$ | Br | n-Bu | Cl | Cl | n-Bu | Br | Cl | n-Bu |
| $CH_3$ | Br | s-Bu | Cl | Cl | s-Bu | Br | Cl | s-Bu |
| $CH_3$ | Br | i-Bu | Cl | Cl | i-Bu | Br | Cl | i-Bu |
| $CH_3$ | Br | $CH_2$-c-Pr | Cl | Cl | CH2-c-Pr | Br | Cl | $CH_2$-c-Pr |
| $CH_3$ | Br | CH(Me)-c-Pr | Cl | Cl | CH(Me)-c-Pr | Br | Cl | CH(Me)-c-Pr |
| $CH_3$ | H | H | Cl | Br | H | Br | H | H |
| $CH_3$ | H | Me | Cl | Br | Me | Br | H | Me |
| $CH_3$ | H | Et | Cl | Br | Et | Br | H | Et |
| $CH_3$ | H | i-Pr | Cl | Br | i-Pr | Br | H | i-Pr |
| $CH_3$ | H | t-Bu | Cl | Br | t-Bu | Br | H | t-Bu |
| $CH_3$ | H | n-Pr | Cl | Br | n-Pr | Br | H | n-Pr |
| $CH_3$ | H | n-Bu | Cl | Br | n-Bu | Br | H | n-Bu |
| $CH_3$ | H | s-Bu | Cl | Br | s-Bu | Br | H | s-Bu |
| $CH_3$ | H | i-Bu | Cl | Br | i-Bu | Br | H | i-Bu |
| $CH_3$ | H | $CH_2$-c-Pr | Cl | Br | $CH_2$-c-Pr | Br | H | $CH_2$-c-Pr |
| $CH_3$ | H | CH(Me)-c-Pr | Cl | Br | CH(Me)-c-Pr | Br | H | CH(Me)-c-Pr |
| H | Cl | H | H | Cl | t-Bu | H | Cl | s-Bu |
| H | Cl | Me | H | Cl | n-Pr | H | Cl | i-Bu |
| H | Cl | Et | H | Cl | n-Bu | H | Cl | $CH_2$-c-Pr |
| H | Cl | i-Pr | H | Cl | CH(Me)-c-Pr | | | |

The present disclosure also includes Table 2, which is constructed the same as Table 1 above, except that Formula 3a is replaced with Formula 3c shown below. For example, the first entry in Table 2 is a compound of Formula 3c wherein $R^1$ is $CH_3$, $R^2$ is $C_1$ and $R^3$ is H.

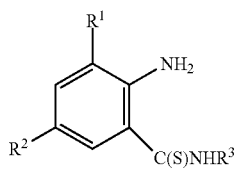

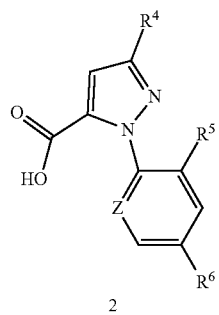

The present disclosure also includes Tables 4 through 7, each of which is constructed the same as Table 3 above, except that the Header Row in Table 3 (i.e. Z is N and) is replaced with the respective Header Row shown below in Tables 4 through 7. For example, the first entry in Table 4 is a compound of Formula 2 wherein Z is $CR^7$, $R^7$ is H, $R^4$ is $CF_3$, $R^5$ is F, and $R^6$ is H. Tables 5 through 7 are constructed similarly.

TABLE 3 wherein Z is N and

| $R^4$ | $R^5$ | $R^6$ | $R^4$ | $R^5$ | $R^6$ | $R^4$ | $R^5$ | $R^6$ |
|---|---|---|---|---|---|---|---|---|
| $CF_3$ | F | H | Br | F | H | $CF_2CF_2CF_3$ | F | H |
| $CF_3$ | F | F | Br | F | F | $CF_2CF_2CF_3$ | F | F |
| $CF_3$ | F | Cl | Br | F | Cl | $CF_2CF_2CF_3$ | F | Cl |
| $CF_3$ | Cl | H | Br | Cl | H | $CF_2CF_2CF_3$ | Cl | H |
| $CF_3$ | Cl | F | Br | Cl | F | $CF_2CF_2CF_3$ | Cl | F |
| $CF_3$ | Cl | Cl | Br | Cl | Cl | $CF_2CF_2CF_3$ | Cl | Cl |
| $CF_3$ | Br | H | Br | Br | H | $CF_2CF_2CF_3$ | Br | H |
| $CF_3$ | Br | F | Br | Br | F | $CF_2CF_2CF_3$ | Br | F |
| $CF_3$ | Br | Cl | Br | Br | Cl | $CF_2CF_2CF_3$ | Br | Cl |
| $CF_3$ | F | H | Cl | F | H | $CH_2CF_3$ | F | H |
| $CF_3$ | F | F | Cl | F | F | $CH_2CF_3$ | F | F |
| $CF_3$ | F | Cl | Cl | F | Cl | $CH_2CF_3$ | F | Cl |
| $CF_3$ | Cl | H | Cl | Cl | H | $CH_2CF_3$ | Cl | H |
| $CH_3$ | Cl | F | Cl | Cl | F | $CH_2CF_3$ | Cl | F |
| $CH_3$ | Cl | Cl | Cl | Cl | Cl | $CH_2CF_3$ | Cl | Cl |
| $CH_3$ | Br | H | Cl | Br | H | $CH_2CF_3$ | Br | H |
| $CH_3$ | Br | F | Cl | Br | F | $CH_2CF_3$ | Br | F |
| $CH_3$ | Br | Cl | Cl | Br | Cl | $CH_2CF_3$ | Br | Cl |
| $CHF_2$ | F | H | $OCF_2H$ | F | H | $CCl_2CF_3$ | F | H |
| $CHF_2$ | F | F | $OCF_2H$ | F | F | $CCl_2CF_3$ | F | F |
| $CHF_2$ | F | Cl | $OCF_2H$ | F | Cl | $CCl_2CF_3$ | F | Cl |
| $CHF_2$ | Cl | H | $OCF_2H$ | Cl | H | $CCl_2CF_3$ | Cl | H |
| $CHF_2$ | Cl | F | $OCF_2H$ | Cl | F | $CCl_2CF_3$ | Cl | F |
| $CHF_2$ | Cl | Cl | $OCF_2H$ | Cl | Cl | $CCl_2CF_3$ | Cl | Cl |
| $CHF_2$ | Br | H | $OCF_2H$ | Br | H | $CCl_2CF_3$ | Br | H |
| $CHF_2$ | Br | F | $OCF_2H$ | Br | F | $CCl_2CF_3$ | Br | F |
| $CHF_2$ | Br | Cl | $OCF_2H$ | Br | Cl | $CCl_2CF_3$ | Br | Cl |
| $CH_2F$ | F | H | $OCH_2CF_3$ | F | H | $CH_2$(2H-tetrazol-2-yl) | F | H |
| $CH_2F$ | F | F | $OCH_2CF_3$ | F | F | $CH_2$(2H-tetrazol-2-yl) | F | F |
| $CH_2F$ | F | Cl | $OCH_2CF_3$ | F | Cl | $CH_2$(2H-tetrazol-2-yl) | F | Cl |
| $CH_2F$ | Cl | H | $OCH_2CF_3$ | Cl | H | $CH_2$(2H-tetrazol-2-yl) | Cl | H |
| $CH_2F$ | Cl | F | $OCH_2CF_3$ | Cl | F | $CH_2$(2H-tetrazol-2-yl) | Cl | F |
| $CH_2F$ | Cl | Cl | $OCH_2CF_3$ | Cl | Cl | $CH_2$(2H-tetrazol-2-yl) | Cl | Cl |
| $CH_2F$ | Br | H | $OCH_2CF_3$ | Br | H | $CH_2$(2H-tetrazol-2-yl) | Br | H |
| $CH_2F$ | Br | F | $OCH_2CF_3$ | Br | F | $CH_2$(2H-tetrazol-2-yl) | Br | F |
| $CH_2F$ | Br | Cl | $OCH_2CF_3$ | Br | Cl | $CH_2$(2H-tetrazol-2-yl) | Br | Cl |
| $CH_2Br$ | F | H | $CF_2CF_3$ | F | H | $CH_2$(5-$CF_3$-2H-tetrazol-2-yl) | F | H |
| $CH_2Br$ | F | F | $CF_2CF_3$ | F | F | $CH_2$(5-$CF_3$-2H-tetrazol-2-yl) | F | F |
| $CH_2Br$ | F | Cl | $CF_2CF_3$ | F | Cl | $CH_2$(5-$CF_3$-2H-tetrazol-2-yl) | F | Cl |
| $CH_2Br$ | Cl | H | $CF_2CF_3$ | Cl | H | $CH_2$(5-$CF_3$-2H-tetrazol-2-yl) | Cl | H |
| $CH_2Br$ | Cl | F | $CF_2CF_3$ | Cl | F | $CH_2$(5-$CF_3$-2H-tetrazol-2-yl)) | Cl | F |
| $CH_2Br$ | Cl | Cl | $CF_2CF_3$ | Cl | Cl | $CH_2$(5-$CF_3$-2H-tetrazol-2-yl) | Cl | Cl |
| $CH_2Br$ | Br | H | $CF_2CF_3$ | Br | H | $CH_2$(5-$CF_3$-2H-tetrazol-2-yl) | Br | H |
| $CH_2Br$ | Br | F | $CF_2CF_3$ | Br | F | $CH_2$(5-$CF_3$-2H-tetrazol-2-yl) | Br | F |
| $CH_2Br$ | Br | Cl | $CF_2CF_3$ | Br | Cl | $CH_2$(5-$CF_3$-2H-tetrazol-2-yl) | Br | Cl |

| Table | Header row |
|---|---|
| 4 | Z is $CR^7$, $R^7$ is H and |
| 5 | Z is $CR^7$, $R^7$ is F and |
| 6 | Z is $CR^7$, $R^7$ is Cl and |
| 7 | Z is $CR^7$, $R^7$ is Br and |

Table 8 illustrates specific transformations to prepare compounds of Formula 1 according to a method of the present disclosure.

TABLE 8

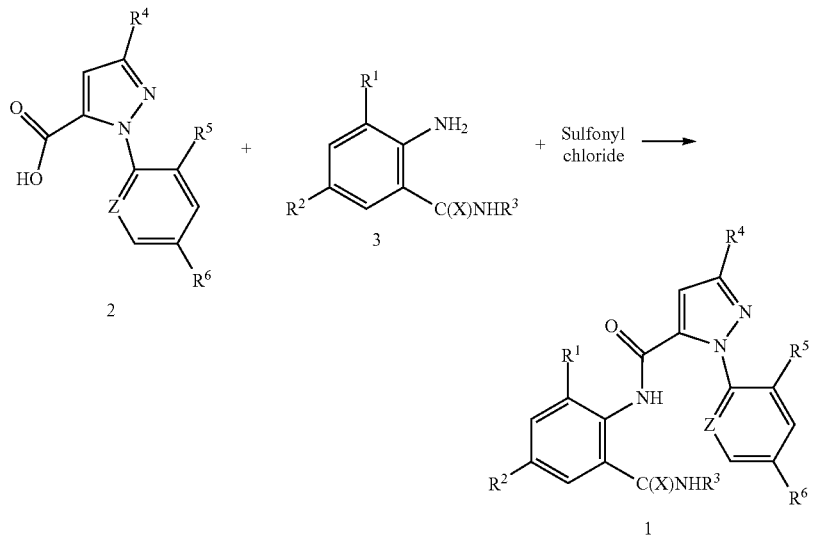

wherein
X is O, Z is N, $R^1$ is $CH_3$, $R^2$ is Cl, $R^3$ is H and

| $R^4$ | $R^5$ | $R^6$ | $R^4$ | $R^5$ | $R^6$ | $R^4$ | $R^5$ | $R^6$ |
|---|---|---|---|---|---|---|---|---|
| $CF_3$ | F | H | Br | F | H | $CF_2CF_2CF_3$ | F | H |
| $CF_3$ | F | F | Br | F | F | $CF_2CF_2CF_3$ | F | F |
| $CF_3$ | F | Cl | Br | F | Cl | $CF_2CF_2CF_3$ | F | Cl |
| $CF_3$ | Cl | H | Br | Cl | H | $CF_2CF_2CF_3$ | Cl | H |
| $CF_3$ | Cl | F | Br | Cl | F | $CF_2CF_2CF_3$ | Cl | F |
| $CF_3$ | Cl | Cl | Br | Cl | Cl | $CF_2CF_2CF_3$ | Cl | Cl |
| $CF_3$ | Br | H | Br | Br | H | $CF_2CF_2CF_3$ | Br | H |
| $CF_3$ | Br | F | Br | Br | F | $CF_2CF_2CF_3$ | Br | F |
| $CF_3$ | Br | Cl | Br | Br | Cl | $CF_2CF_2CF_3$ | Br | Cl |
| $CF_3$ | F | H | Cl | F | H | $CH_2CF_3$ | F | H |
| $CF_3$ | F | F | Cl | F | F | $CH_2CF_3$ | F | F |
| $CF_3$ | F | Cl | Cl | F | Cl | $CH_2CF_3$ | F | Cl |
| $CF_3$ | Cl | H | Cl | Cl | H | $CH_2CF_3$ | Cl | H |
| $CF_3$ | Cl | F | Cl | Cl | F | $CH_2CF_3$ | Cl | F |
| $CF_3$ | Cl | Cl | Cl | Cl | Cl | $CH_2CF_3$ | Cl | Cl |
| $CF_3$ | Br | H | Cl | Br | H | $CH_2CF_3$ | Br | H |
| $CF_3$ | Br | F | Cl | Br | F | $CH_2CF_3$ | Br | F |
| $CF_3$ | Br | Cl | Cl | Br | Cl | $CH_2CF_3$ | Br | Cl |
| $CHF_2$ | F | H | $OCF_2H$ | F | H | $CCl_2CF_3$ | F | H |
| $CHF_2$ | F | F | $OCF_2H$ | F | F | $CCl_2CF_3$ | F | F |
| $CHF_2$ | F | Cl | $OCF_2H$ | F | Cl | $CCl_2CF_3$ | F | Cl |
| $CHF_2$ | Cl | H | $OCF_2H$ | Cl | H | $CCl_2CF_3$ | Cl | H |
| $CHF_2$ | Cl | F | $OCF_2H$ | Cl | F | $CCl_2CF_3$ | Cl | F |
| $CHF_2$ | Cl | Cl | $OCF_2H$ | Cl | Cl | $CCl_2CF_3$ | Cl | Cl |
| $CHF_2$ | Br | H | $OCF_2H$ | Br | H | $CCl_2CF_3$ | Br | H |
| $CHF_2$ | Br | F | $OCF_2H$ | Br | F | $CCl_2CF_3$ | Br | F |
| $CHF_2$ | Br | Cl | $OCF_2H$ | Br | Cl | $CCl_2CF_3$ | Br | Cl |
| $CH_2F$ | F | H | $OCH_2CF_3$ | F | H | $CH_2$(2H-tetrazol-2-yl) | F | H |
| $CH_2F$ | F | F | $OCH_2CF_3$ | F | F | $CH_2$(2H-tetrazol-2-yl) | F | F |
| $CH_2F$ | F | Cl | $OCH_2CF_3$ | F | Cl | $CH_2$(2H-tetrazol-2-yl) | F | Cl |
| $CH_2F$ | Cl | H | $OCH_2CF_3$ | Cl | H | $CH_2$(2H-tetrazol-2-yl) | Cl | H |
| $CH_2F$ | Cl | F | $OCH_2CF_3$ | Cl | F | $CH_2$(2H-tetrazol-2-yl) | Cl | F |
| $CH_2F$ | Cl | Cl | $OCH_2CF_3$ | Cl | Cl | $CH_2$(2H-tetrazol-2-y1) | Cl | Cl |
| $CH_2F$ | Br | H | $OCH_2CF_3$ | Br | H | $CH_2$(2H-tetrazol-2-yl) | Br | H |
| $CH_2F$ | Br | F | $OCH_2CF_3$ | Br | F | $CH_2$(2H-tetrazol-2-yl) | Br | F |

TABLE 8-continued

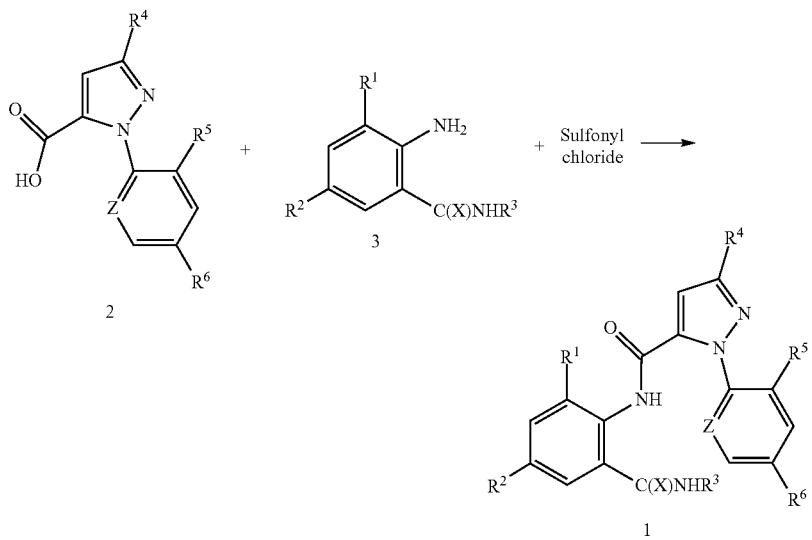

wherein
X is O, Z is N, R¹ is CH₃, R² is Cl, R³ is H and

| R⁴ | R⁵ | R⁶ | R⁴ | R⁵ | R⁶ | R⁴ | R⁵ | R⁶ |
|---|---|---|---|---|---|---|---|---|
| CH₂F | Br | Cl | OCH₂CF₃ | Br | Cl | CH₂(2H-tetrazol-2-yl) | Br | Cl |
| CH₂Br | F | H | CF₂CF₃ | F | H | CH₂(5-CF₃-2H-tetrazol-2-yl) | F | H |
| CH₂Br | F | F | CF₂CF₃ | F | F | CH₂(5-CF₃-2H-tetrazol-2-yl) | F | F |
| CH₂Br | F | Cl | CF₂CF₃ | F | Cl | CH₂(5-CF₃-2H-tetrazol-2-yl) | F | Cl |
| CH₂Br | Cl | H | CF₂CF₃ | Cl | H | CH₂(5-CF₃-2H-tetrazol-2-yl) | Cl | H |
| CH₂Br | Cl | F | CF₂CF₃ | Cl | F | CH₂(5-CF₃-2H-tetrazol-2-yl)) | Cl | F |
| CH₂Br | Cl | Cl | CF₂CF₃ | Cl | Cl | CH₂(5-CF₃-2H-tetrazol-2-yl) | Cl | Cl |
| CH₂Br | Br | H | CF₂CF₃ | Br | H | CH₂(5-CF₃-2H-tetrazol-2-yl) | Br | H |
| CH₂Br | Br | F | CF₂CF₃ | Br | F | CH₂(5-CF₃-2H-tetrazol-2-yl) | Br | F |
| CH₂Br | Br | Cl | CF₂CF₃ | Br | Cl | CH₂(5-CF₃-2H-tetrazol-2-yl) | Br | Cl |

The present disclosure also includes Tables 9 through 227, each of which is constructed the same as Table 8 above, except that the Header Row in Table 8 (i.e. X is O, Z is N, R¹ is CH₃, R² is Cl, R³ is H and) is replaced with the respective Header Row shown below in Tables 9 through 227. For example, the first entry in Table 9 is a compound of Formula 1 wherein X is O, Z is N, R¹ is CH₃, R² is Cl, R³ is H, R⁴ is CF₃, R⁵ is F, and R⁶ is H. Tables 10 through 227 are constructed similarly.

| Table | Header Row | | | | | |
|---|---|---|---|---|---|---|
| 9 | X is O, | Z is N, | R¹ is CH₃, | R² is Cl, | R³ is Me | and |
| 10 | X is O, | Z is N, | R¹ is CH₃, | R² is Cl, | R³ is Et | and |
| 11 | X is O, | Z is N, | R¹ is CH₃, | R² is Cl, | R³ is i-Pr | and |
| 12 | X is O, | Z is N, | R¹ is CH₃, | R² is Cl, | R³ is t-Bu | and |
| 13 | X is O, | Z is N, | R¹ is CH₃, | R² is Cl, | R³ is n-Pr | and |
| 14 | X is O, | Z is N, | R¹ is CH₃, | R² is Cl, | R³ is n-Bu | and |
| 15 | X is O, | Z is N, | R¹ is CH₃, | R² is Cl, | R³ is s-Bu | and |
| 16 | X is O, | Z is N, | R¹ is CH₃, | R² is Cl, | R³ is i-Bu | and |
| 17 | X is O, | Z is N, | R¹ is CH₃, | R² is Cl, | R³ is CH₂-c-Pr | and |
| 18 | X is O, | Z is N, | R¹ is CH₃, | R² is Cl, | R³ is CH(Me)-c-Pr | and |
| 19 | X is O, | Z is N, | R¹ is CH₃, | R² is Br, | R³ is H | and |
| 20 | X is O, | Z is N, | R¹ is CH₃, | R² is Br, | R³ is Me | and |
| 21 | X is O, | Z is N, | R¹ is CH₃, | R² is Br, | R³ is Et | and |
| 22 | X is O, | Z is N, | R¹ is CH₃, | R² is Br, | R³ is i-Pr | and |
| 23 | X is O, | Z is N, | R¹ is CH₃, | R² is Br, | R³ is t-Bu | and |
| 24 | X is O, | Z is N, | R¹ is CH₃, | R² is Br, | R³ is n-Pr | and |
| 25 | X is O, | Z is N, | R¹ is CH₃, | R² is Br, | R³ is n-Bu | and |
| 26 | X is O, | Z is N, | R¹ is CH₃, | R² is Br, | R³ is s-Bu | and |
| 27 | X is O, | Z is N, | R¹ is CH₃, | R² is Br, | R³ is i-Bu | and |
| 28 | X is O, | Z is N, | R¹ is CH₃, | R² is Br, | R³ is CH₂-c-Pr | and |
| 29 | X is O, | Z is N, | R¹ is CH₃, | R² is Br, | R³ is CH(Me)-c-Pr | and |
| 30 | X is O, | Z is N, | R¹ is CH₃, | R² is H, | R³ is H | and |
| 31 | X is O, | Z is N, | R¹ is CH₃, | R² is H, | R³ is Me | and |
| 32 | X is O, | Z is N, | R¹ is CH₃, | R² is H, | R³ is Et | and |
| 33 | X is O, | Z is N, | R¹ is CH₃, | R² is H, | R³ is i-Pr | and |

-continued

| Table | | | | | Header Row | |
|---|---|---|---|---|---|---|
| 34 | X is O, | Z is N, | R$^1$ is CH$_3$, | R$^2$ is H, | R$^3$ is t-Bu | and |
| 35 | X is O, | Z is N, | R$^1$ is CH$_3$, | R$^2$ is H, | R$^3$ is n-Pr | and |
| 36 | X is O, | Z is N, | R$^1$ is CH$_3$, | R$^2$ is H, | R$^3$ is n-Bu | and |
| 37 | X is O, | Z is N, | R$^1$ is CH$_3$, | R$^2$ is H, | R$^3$ is s-Bu | and |
| 38 | X is O, | Z is N, | R$^1$ is CH$_3$, | R$^2$ is H, | R$^3$ is i-Bu | and |
| 39 | X is O, | Z is N, | R$^1$ is CH$_3$, | R$^2$ is H, | R$^3$ is CH$_2$-c-Pr | and |
| 40 | X is O, | Z is N, | R$^1$ is CH$_3$, | R$^2$ is H, | R$^3$ is CH(Me)-c-Pr | and |
| 41 | X is O, | Z is N, | R$^1$ is CH$_3$, | R$^2$ is Cl, | R$^3$ is H | and |
| 42 | X is O, | Z is N, | R$^1$ is CH$_3$, | R$^2$ is Cl, | R$^3$ is Me | and |
| 43 | X is O, | Z is N, | R$^1$ is CH$_3$, | R$^2$ is Cl, | R$^3$ is Et | and |
| 44 | X is O, | Z is N, | R$^1$ is H, | R$^2$ is Cl, | R$^3$ is i-Pr | and |
| 45 | X is O, | Z is N, | R$^1$ is H, | R$^2$ is Cl, | R$^3$ is t-Bu | and |
| 46 | X is O, | Z is N, | R$^1$ is H, | R$^2$ is Cl, | R$^3$ is n-Pr | and |
| 47 | X is O, | Z is N, | R$^1$ is H, | R$^2$ is Cl, | R$^3$ is n-Bu | and |
| 48 | X is O, | Z is N, | R$^1$ is H, | R$^2$ is Cl, | R$^3$ is s-Bu | and |
| 49 | X is O, | Z is N, | R$^1$ is H, | R$^2$ is Cl, | R$^3$ is i-Bu | and |
| 50 | X is O, | Z is N, | R$^1$ is H, | R$^2$ is Cl, | R$^3$ is CH$_2$-c-Pr | and |
| 51 | X is O, | Z is N, | R$^1$ is H, | R$^2$ is Cl, | R$^3$ is CH(Me)-c-Pr | and |
| 52 | X is O, | Z is N, | R$^1$ is CH$_3$, | R$^2$ is CN, | R$^3$ is H | and |
| 53 | X is O, | Z is N, | R$^1$ is CH$_3$, | R$^2$ is CN, | R$^3$ is Me | and |
| 54 | X is O, | Z is N, | R$^1$ is CH$_3$, | R$^2$ is CN, | R$^3$ is Et | and |
| 55 | X is O, | Z is N, | R$^1$ is CH$_3$, | R$^2$ is CN, | R$^3$ is i-Pr | and |
| 56 | X is O, | Z is N, | R$^1$ is CH$_3$, | R$^2$ is CN, | R$^3$ is t-Bu | and |
| 57 | X is O, | Z is N, | R$^1$ is CH$_3$, | R$^2$ is CN, | R$^3$ is n-Pr | and |
| 58 | X is O, | Z is N, | R$^1$ is CH$_3$, | R$^2$ is CN, | R$^3$ is n-Bu | and |
| 59 | X is O, | Z is N, | R$^1$ is CH$_3$, | R$^2$ is CN, | R$^3$ is s-Bu | and |
| 60 | X is O, | Z is N, | R$^1$ is CH$_3$, | R$^2$ is CN, | R$^3$ is i-Bu | and |
| 61 | X is O, | Z is N, | R$^1$ is CH$_3$, | R$^2$ is CN, | R$^3$ is CH$_2$-c-Pr | and |
| 62 | X is O, | Z is N, | R$^1$ is CH$_3$, | R$^2$ is CN, | R$^3$ is CH(Me)-c-Pr | and |
| 63 | X is O, | Z is N, | R$^1$ is Cl, | R$^2$ is Cl, | R$^3$ is H | and |
| 64 | X is O, | Z is N, | R$^1$ is Cl, | R$^2$ is Cl, | R$^3$ is Me | and |
| 65 | X is O, | Z is N, | R$^1$ is Cl, | R$^2$ is Cl, | R$^3$ is Et | and |
| 66 | X is O, | Z is N, | R$^1$ is Cl, | R$^2$ is Cl, | R$^3$ is i-Pr | and |
| 67 | X is O, | Z is N, | R$^1$ is Cl, | R$^2$ is Cl, | R$^3$ is t-Bu | and |
| 68 | X is O, | Z is N, | R$^1$ is Cl, | R$^2$ is Cl, | R$^3$ is n-Pr | and |
| 69 | X is O, | Z is N, | R$^1$ is Cl, | R$^2$ is Cl, | R$^3$ is n-Bu | and |
| 70 | X is O, | Z is N, | R$^1$ is Cl, | R$^2$ is Cl, | R$^3$ is s-Bu | and |
| 71 | X is O, | Z is N, | R$^1$ is Cl, | R$^2$ is Cl, | R$^3$ is i-Bu | and |
| 72 | X is O, | Z is N, | R$^1$ is Cl, | R$^2$ is Cl, | R$^3$ is CH$_2$-c-Pr | and |
| 73 | X is O, | Z is N, | R$^1$ is Cl, | R$^2$ is Cl, | R$^3$ is CH(Me)-c-Pr | and |
| 74 | X is O, | Z is N, | R$^1$ is Cl, | R$^2$ is Br, | R$^3$ is H | and |
| 75 | X is O, | Z is N, | R$^1$ is Cl, | R$^2$ is Br, | R$^3$ is Me | and |
| 76 | X is O, | Z is N, | R$^1$ is Cl, | R$^2$ is Br, | R$^3$ is Et | and |
| 77 | X is O, | Z is N, | R$^1$ is Cl, | R$^2$ is Br, | R$^3$ is i-Pr | and |
| 78 | X is O, | Z is N, | R$^1$ is Cl, | R$^2$ is Br, | R$^3$ is t-Bu | and |
| 79 | X is O, | Z is N, | R$^1$ is Cl, | R$^2$ is Br, | R$^3$ is n-Pr | and |
| 80 | X is O, | Z is N, | R$^1$ is Cl, | R$^2$ is Br, | R$^3$ is n-Bu | and |
| 81 | X is O, | Z is N, | R$^1$ is Cl, | R$^2$ is Br, | R$^3$ is s-Bu | and |
| 82 | X is O, | Z is N, | R$^1$ is Cl, | R$^2$ is Br, | R$^3$ is i-Bu | and |
| 83 | X is O, | Z is N, | R$^1$ is Cl, | R$^2$ is Br, | R$^3$ is CH$_2$-c-Pr | and |
| 84 | X is O, | Z is N, | R$^1$ is Cl, | R$^2$ is Br, | R$^3$ is CH(Me)-c-Pr | and |
| 85 | X is O, | Z is N, | R$^1$ is Cl, | R$^2$ is CN, | R$^3$ is H | and |
| 86 | X is O, | Z is N, | R$^1$ is Cl, | R$^2$ is CN, | R$^3$ is Me | and |
| 87 | X is O, | Z is N, | R$^1$ is Cl, | R$^2$ is CN, | R$^3$ is Et | and |
| 88 | X is O, | Z is N, | R$^1$ is Cl, | R$^2$ is CN, | R$^3$ is i-Pr | and |
| 89 | X is O, | Z is N, | R$^1$ is Cl, | R$^2$ is CN, | R$^3$ is t-Bu | and |
| 90 | X is O, | Z is N, | R$^1$ is Cl, | R$^2$ is CN, | R$^3$ is n-Pr | and |
| 91 | X is O, | Z is N, | R$^1$ is Cl, | R$^2$ is CN, | R$^3$ is n-Bu | and |
| 92 | X is O, | Z is N, | R$^1$ is Cl, | R$^2$ is CN, | R$^3$ is s-Bu | and |
| 93 | X is O, | Z is N, | R$^1$ is Cl, | R$^2$ is CN, | R$^3$ is i-Bu | and |
| 94 | X is O, | Z is N, | R$^1$ is Cl, | R$^2$ is CN, | R$^3$ is CH$_2$-c-Pr | and |
| 95 | X is O, | Z is N, | R$^1$ is Cl, | R$^2$ is CN, | R$^3$ is CH(Me)-c-Pr | and |
| 96 | X is O, | Z is N, | R$^1$ is Br, | R$^2$ is Cl, | R$^3$ is H | and |
| 97 | X is O, | Z is N, | R$^1$ is Br, | R$^2$ is Cl, | R$^3$ is Me | and |
| 98 | X is O, | Z is N, | R$^1$ is Br, | R$^2$ is Cl, | R$^3$ is Et | and |
| 99 | X is O, | Z is N, | R$^1$ is Br, | R$^2$ is Cl, | R$^3$ is i-Pr | and |
| 100 | X is O, | Z is N, | R$^1$ is Br, | R$^2$ is Cl, | R$^3$ is t-Bu | and |
| 101 | X is O, | Z is N, | R$^1$ is Br, | R$^2$ is Cl, | R$^3$ is n-Pr | and |
| 102 | X is O, | Z is N, | R$^1$ is Br, | R$^2$ is Cl, | R$^3$ is n-Bu | and |
| 103 | X is O, | Z is N, | R$^1$ is Br, | R$^2$ is Cl, | R$^3$ is s-Bu | and |
| 104 | X is O, | Z is N, | R$^1$ is Br, | R$^2$ is Cl, | R$^3$ is i-Bu | and |
| 105 | X is O, | Z is N, | R$^1$ is Br, | R$^2$ is Cl, | R$^3$ is CH$_2$-c-Pr | and |
| 106 | X is O, | Z is N, | R$^1$ is Br, | R$^2$ is Cl, | R$^3$ is CH(Me)-c-Pr | and |
| 107 | X is O, | Z is N, | R$^1$ is Br, | R$^2$ is H, | R$^3$ is H | and |
| 108 | X is O, | Z is N, | R$^1$ is Br, | R$^2$ is H, | R$^3$ is Me | and |
| 109 | X is O, | Z is N, | R$^1$ is Br, | R$^2$ is H, | R$^3$ is Et | and |
| 110 | X is O, | Z is N, | R$^1$ is Br, | R$^2$ is H, | R$^3$ is i-Pr | and |

-continued

| Table | | | | | Header Row | |
|---|---|---|---|---|---|---|
| 111 | X is O, | Z is N, | R$^1$ is Br, | R$^2$ is H, | R$^3$ is t-Bu | and |
| 112 | X is O, | Z is N, | R$^1$ is Br, | R$^2$ is H, | R$^3$ is n-Pr | and |
| 113 | X is O, | Z is N, | R$^1$ is Br, | R$^2$ is H, | R$^3$ is n-Bu | and |
| 114 | X is O, | Z is N, | R$^1$ is Br, | R$^2$ is H, | R$^3$ is s-Bu | and |
| 115 | X is O, | Z is N, | R$^1$ is Br, | R$^2$ is H, | R$^3$ is i-Bu | and |
| 116 | X is O, | Z is N, | R$^1$ is Br, | R$^2$ is H, | R$^3$ is CH$_2$-c-Pr | and |
| 117 | X is O, | Z is N, | R$^1$ is Br, | R$^2$ is H, | R$^3$ is CH(Me)-c-Pr | and |
| 118 | X is S, | Z is N, | R$^1$ is CH$_3$, | R$^2$ is Cl, | R$^3$ is H | and |
| 119 | X is S, | Z is N, | R$^1$ is CH$_3$, | R$^2$ is Cl, | R$^3$ is Me | and |
| 120 | X is S, | Z is N, | R$^1$ is CH$_3$, | R$^2$ is Cl, | R$^3$ is Et | and |
| 121 | X is S, | Z is N, | R$^1$ is CH$_3$, | R$^2$ is Cl, | R$^3$ is i-Pr | and |
| 122 | X is S, | Z is N, | R$^1$ is CH$_3$, | R$^2$ is Cl, | R$^3$ is t-Bu | and |
| 123 | X is S, | Z is N, | R$^1$ is CH$_3$, | R$^2$ is Cl, | R$^3$ is n-Pr | and |
| 124 | X is S, | Z is N, | R$^1$ is CH$_3$, | R$^2$ is Cl, | R$^3$ is n-Bu | and |
| 125 | X is S, | Z is N, | R$^1$ is CH$_3$, | R$^2$ is Cl, | R$^3$ is s-Bu | and |
| 126 | X is S, | Z is N, | R$^1$ is CH$_3$, | R$^2$ is Cl, | R$^3$ is i-Bu | and |
| 127 | X is S, | Z is N, | R$^1$ is CH$_3$, | R$^2$ is Cl, | R$^3$ is CH$_2$-c-Pr | and |
| 128 | X is S, | Z is N, | R$^1$ is CH$_3$, | R$^2$ is Cl, | R$^3$ is CH(Me)-c-Pr | and |
| 129 | X is S, | Z is N, | R$^1$ is CH$_3$, | R$^2$ is Br, | R$^3$ is H | and |
| 130 | X is S, | Z is N, | R$^1$ is CH$_3$, | R$^2$ is Br, | R$^3$ is Me | and |
| 131 | X is S, | Z is N, | R$^1$ is CH$_3$, | R$^2$ is Br, | R$^3$ is Et | and |
| 132 | X is S, | Z is N, | R$^1$ is CH$_3$, | R$^2$ is Br, | R$^3$ is i-Pr | and |
| 133 | X is S, | Z is N, | R$^1$ is CH$_3$, | R$^2$ is Br, | R$^3$ is t-Bu | and |
| 134 | X is S, | Z is N, | R$^1$ is CH$_3$, | R$^2$ is Br, | R$^3$ is n-Pr | and |
| 135 | X is S, | Z is N, | R$^1$ is CH$_3$, | R$^2$ is Br, | R$^3$ is n-Bu | and |
| 136 | X is S, | Z is N, | R$^1$ is CH$_3$, | R$^2$ is Br, | R$^3$ is s-Bu | and |
| 137 | X is S, | Z is N, | R$^1$ is CH$_3$, | R$^2$ is Br, | R$^3$ is i-Bu | and |
| 138 | X is S, | Z is N, | R$^1$ is CH$_3$, | R$^2$ is Br, | R$^3$ is CH$_2$-c-Pr | and |
| 139 | X is S, | Z is N, | R$^1$ is CH$_3$, | R$^2$ is Br, | R$^3$ is CH(Me)-c-Pr | and |
| 140 | X is S, | Z is N, | R$^1$ is CH$_3$, | R$^2$ is H, | R$^3$ is H | and |
| 141 | X is S, | Z is N, | R$^1$ is CH$_3$, | R$^2$ is H, | R$^3$ is Me | and |
| 142 | X is S, | Z is N, | R$^1$ is CH$_3$, | R$^2$ is H, | R$^3$ is Et | and |
| 143 | X is S, | Z is N, | R$^1$ is CH$_3$, | R$^2$ is H, | R$^3$ is i-Pr | and |
| 144 | X is S, | Z is N, | R$^1$ is CH$_3$, | R$^2$ is H, | R$^3$ is t-Bu | and |
| 145 | X is S, | Z is N, | R$^1$ is CH$_3$, | R$^2$ is H, | R$^3$ is n-Pr | and |
| 146 | X is S, | Z is N, | R$^1$ is CH$_3$, | R$^2$ is H, | R$^3$ is n-Bu | and |
| 147 | X is S, | Z is N, | R$^1$ is CH$_3$, | R$^2$ is H, | R$^3$ is s-Bu | and |
| 148 | X is S, | Z is N, | R$^1$ is CH$_3$, | R$^2$ is H, | R$^3$ is i-Bu | and |
| 149 | X is S, | Z is N, | R$^1$ is CH$_3$, | R$^2$ is H, | R$^3$ is CH$_2$-c-Pr | and |
| 150 | X is S, | Z is N, | R$^1$ is CH$_3$, | R$^2$ is H, | R$^3$ is CH(Me)-c-Pr | and |
| 151 | X is S, | Z is N, | R$^1$ is CH$_3$, | R$^2$ is Cl, | R$^3$ is H | and |
| 152 | X is S, | Z is N, | R$^1$ is CH$_3$, | R$^2$ is Cl, | R$^3$ is Me | and |
| 153 | X is S, | Z is N, | R$^1$ is CH$_3$, | R$^2$ is Cl, | R$^3$ is Et | and |
| 154 | X is S, | Z is N, | R$^1$ is H, | R$^2$ is Cl, | R$^3$ is i-Pr | and |
| 155 | X is S, | Z is N, | R$^1$ is H, | R$^2$ is Cl, | R$^3$ is t-Bu | and |
| 156 | X is S, | Z is N, | R$^1$ is H, | R$^2$ is Cl, | R$^3$ is n-Pr | and |
| 157 | X is S, | Z is N, | R$^1$ is H, | R$^2$ is Cl, | R$^3$ is n-Bu | and |
| 158 | X is S, | Z is N, | R$^1$ is H, | R$^2$ is Cl, | R$^3$ is s-Bu | and |
| 159 | X is S, | Z is N, | R$^1$ is H, | R$^2$ is Cl, | R$^3$ is i-Bu | and |
| 160 | X is S, | Z is N, | R$^1$ is H, | R$^2$ is Cl, | R$^3$ is CH$_2$-c-Pr | and |
| 161 | X is S, | Z is N, | R$^1$ is H, | R$^2$ is Cl, | R$^3$ is CH(Me)-c-Pr | and |
| 162 | X is S, | Z is N, | R$^1$ is CH$_3$, | R$^2$ is CN, | R$^3$ is H | and |
| 163 | X is S, | Z is N, | R$^1$ is CH$_3$, | R$^2$ is CN, | R$^3$ is Me | and |
| 164 | X is S, | Z is N, | R$^1$ is CH$_3$, | R$^2$ is CN, | R$^3$ is Et | and |
| 165 | X is S, | Z is N, | R$^1$ is CH$_3$, | R$^2$ is CN, | R$^3$ is i-Pr | and |
| 166 | X is S, | Z is N, | R$^1$ is CH$_3$, | R$^2$ is CN, | R$^3$ is t-Bu | and |
| 167 | X is S, | Z is N, | R$^1$ is CH$_3$, | R$^2$ is CN, | R$^3$ is n-Pr | and |
| 168 | X is S, | Z is N, | R$^1$ is CH$_3$, | R$^2$ is CN, | R$^3$ is n-Bu | and |
| 169 | X is S, | Z is N, | R$^1$ is CH$_3$, | R$^2$ is CN, | R$^3$ is s-Bu | and |
| 170 | X is S, | Z is N, | R$^1$ is CH$_3$, | R$^2$ is CN, | R$^3$ is i-Bu | and |
| 171 | X is S, | Z is N, | R$^1$ is CH$_3$, | R$^2$ is CN, | R$^3$ is CH$_2$-c-Pr | and |
| 172 | X is S, | Z is N, | R$^1$ is CH$_3$, | R$^2$ is CN, | R$^3$ is CH(Me)-c-Pr | and |
| 173 | X is S, | Z is N, | R$^1$ is Cl, | R$^2$ is Cl, | R$^3$ is H | and |
| 174 | X is S, | Z is N, | R$^1$ is Cl, | R$^2$ is Cl, | R$^3$ is Me | and |
| 175 | X is S, | Z is N, | R$^1$ is Cl, | R$^2$ is Cl, | R$^3$ is Et | and |
| 176 | X is S, | Z is N, | R$^1$ is Cl, | R$^2$ is Cl, | R$^3$ is i-Pr | and |
| 177 | X is S, | Z is N, | R$^1$ is Cl, | R$^2$ is Cl, | R$^3$ is t-Bu | and |
| 178 | X is S, | Z is N, | R$^1$ is Cl, | R$^2$ is Cl, | R$^3$ is n-Pr | and |
| 179 | X is S, | Z is N, | R$^1$ is Cl, | R$^2$ is Cl, | R$^3$ is n-Bu | and |
| 180 | X is S, | Z is N, | R$^1$ is Cl, | R$^2$ is Cl, | R$^3$ is s-Bu | and |
| 181 | X is S, | Z is N, | R$^1$ is Cl, | R$^2$ is Cl, | R$^3$ is i-Bu | and |
| 182 | X is S, | Z is N, | R$^1$ is Cl, | R$^2$ is Cl, | R$^3$ is CH$_2$-c-Pr | and |
| 183 | X is S, | Z is N, | R$^1$ is Cl, | R$^2$ is Cl, | R$^3$ is CH(Me)-c-Pr | and |
| 184 | X is S, | Z is N, | R$^1$ is Cl, | R$^2$ is Br, | R$^3$ is H | and |
| 185 | X is S, | Z is N, | R$^1$ is Cl, | R$^2$ is Br, | R$^3$ is Me | and |
| 186 | X is S, | Z is N, | R$^1$ is Cl, | R$^2$ is Br, | R$^3$ is Et | and |
| 187 | X is S, | Z is N, | R$^1$ is Cl, | R$^2$ is Br, | R$^3$ is i-Pr | and |

-continued

| Table | | | Header Row | | |
|---|---|---|---|---|---|
| 188 | X is S, | Z is N, | $R^1$ is Cl, | $R^2$ is Br, | $R^3$ is t-Bu | and |
| 189 | X is S, | Z is N, | $R^1$ is Cl, | $R^2$ is Br, | $R^3$ is n-Pr | and |
| 190 | X is S, | Z is N, | $R^1$ is Cl, | $R^2$ is Br, | $R^3$ is n-Bu | and |
| 191 | X is S, | Z is N, | $R^1$ is Cl, | $R^2$ is Br, | $R^3$ is s-Bu | and |
| 192 | X is S, | Z is N, | $R^1$ is Cl, | $R^2$ is Br, | $R^3$ is i-Bu | and |
| 193 | X is S, | Z is N, | $R^1$ is Cl, | $R^2$ is Br, | $R^3$ is $CH_2$-c-Pr | and |
| 194 | X is S, | Z is N, | $R^1$ is Cl, | $R^2$ is Br, | $R^3$ is CH(Me)-c-Pr | and |
| 195 | X is S, | Z is N, | $R^1$ is Cl, | $R^2$ is CN, | $R^3$ is H | and |
| 196 | X is S, | Z is N, | $R^1$ is Cl, | $R^2$ is CN, | $R^3$ is Me | and |
| 197 | X is S, | Z is N, | $R^1$ is Cl, | $R^2$ is CN, | $R^3$ is Et | and |
| 198 | X is S, | Z is N, | $R^1$ is Cl, | $R^2$ is CN, | $R^3$ is i-Pr | and |
| 199 | X is S, | Z is N, | $R^1$ is Cl, | $R^2$ is CN, | $R^3$ is t-Bu | and |
| 201 | X is S, | Z is N, | $R^1$ is Cl, | $R^2$ is CN, | $R^3$ is n-Pr | and |
| 202 | X is S, | Z is N, | $R^1$ is Cl, | $R^2$ is CN, | $R^3$ is n-Bu | and |
| 203 | X is S, | Z is N, | $R^1$ is Cl, | $R^2$ is CN, | $R^3$ is s-Bu | and |
| 204 | X is S, | Z is N, | $R^1$ is Cl, | $R^2$ is CN, | $R^3$ is $CH_2$-c-Pr | and |
| 205 | X is S, | Z is N, | $R^1$ is Cl, | $R^2$ is CN, | $R^3$ is CH(Me)-c-Pr | and |
| 206 | X is S, | Z is N, | $R^1$ is Br, | $R^2$ is Cl, | $R^3$ is H | and |
| 207 | X is S, | Z is N, | $R^1$ is Br, | $R^2$ is Cl, | $R^3$ is Me | and |
| 208 | X is S, | Z is N, | $R^1$ is Br, | $R^2$ is Cl, | $R^3$ is Et | and |
| 209 | X is S, | Z is N, | $R^1$ is Br, | $R^2$ is Cl, | $R^3$ is i-Pr | and |
| 210 | X is S, | Z is N, | $R^1$ is Br, | $R^2$ is Cl, | $R^3$ is t-Bu | and |
| 211 | X is S, | Z is N, | $R^1$ is Br, | $R^2$ is Cl, | $R^3$ is n-Pr | and |
| 212 | X is S, | Z is N, | $R^1$ is Br, | $R^2$ is Cl, | $R^3$ is n-Bu | and |
| 213 | X is S, | Z is N, | $R^1$ is Br, | $R^2$ is Cl, | $R^3$ is s-Bu | and |
| 214 | X is S, | Z is N, | $R^1$ is Br, | $R^2$ is Cl, | $R^3$ is i-Bu | and |
| 215 | X is S, | Z is N, | $R^1$ is Br, | $R^2$ is Cl, | $R^3$ is $CH_2$-c-Pr | and |
| 216 | X is S, | Z is N, | $R^1$ is Br, | $R^2$ is Cl, | $R^3$ is CH(Me)-c-Pr | and |
| 217 | X is S, | Z is N, | $R^1$ is Br, | $R^2$ is H, | $R^3$ is H | and |
| 218 | X is S, | Z is N, | $R^1$ is Br, | $R^2$ is H, | $R^3$ is Me | and |
| 219 | X is S, | Z is N, | $R^1$ is Br, | $R^2$ is H, | $R^3$ is Et | and |
| 220 | X is S, | Z is N, | $R^1$ is Br, | $R^2$ is H, | $R^3$ is i-Pr | and |
| 221 | X is S, | Z is N, | $R^1$ is Br, | $R^2$ is H, | $R^3$ is t-Bu | and |
| 222 | X is S, | Z is N, | $R^1$ is Br, | $R^2$ is H, | $R^3$ is n-Pr | and |
| 223 | X is S, | Z is N, | $R^1$ is Br, | $R^2$ is H, | $R^3$ is n-Bu | and |
| 224 | X is S, | Z is N, | $R^1$ is Br, | $R^2$ is H, | $R^3$ is s-Bu | and |
| 225 | X is S, | Z is N, | $R^1$ is Br, | $R^2$ is H, | $R^3$ is i-Bu | and |
| 226 | X is S, | Z is N, | $R^1$ is Br, | $R^2$ is H, | $R^3$ is $CH_2$-c-Pr | and |
| 227 | X is S, | Z is N, | $R^1$ is Br, | $R^2$ is H, | $R^3$ is CH(Me)-c-Pr | |

What is claimed is:

1. A method for preparing a compound of Formula 1

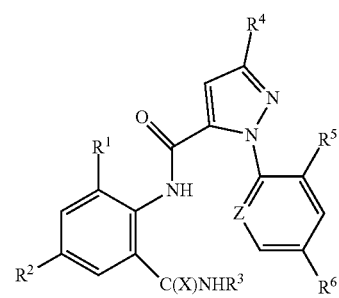

wherein
X is O;
Z is N;
$R^1$ is H, $CH_3$, Cl or Br;
$R^2$ is H, Br, Cl or CN;
$R^3$ is H, $C_1$-$C_4$ alkyl or $C_4$-$C_{10}$ cycloalkylalkyl;
$R^4$ is Cl, or Br; or
$C_1$-$C_4$ alkyl substituted with Q;
$R^5$ is F, Cl or Br;
$R^6$ is H, F or Cl;

Q is a 5- or 6-membered aromatic heterocyclic ring optionally substituted with one or more substituents independently selected from the group consisting of halogen, $C_1$-$C_6$ alkyl, $C_3$-$C_6$ cycloalkyl and $C_1$-$C_6$ haloalkyl;

comprising:

combining (1) a carboxylic acid compound of Formula 2,

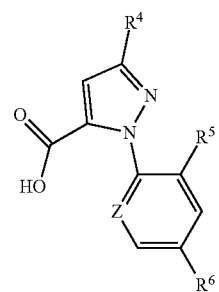

wherein Z, $R^4$, $R^5$, $R^6$, $R^7$, and Q are as defined for the compound of Formula 1; and (2) an aniline compound of Formula 3,

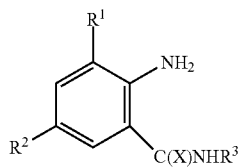

wherein X, $R^1$, $R^2$ and $R^3$ are as defined for the compound of Formula 1;
(3) a sulfonyl chloride to form the compound of Formula 1; wherein the method comprises a continuous process comprising combining the compound of Formula 2, the compound of Formula 3, the sulfonyl chloride continuously in a reaction zone; and removing the compound of Formula 1 continuously in an isolation step further wherein the reaction zone comprises one or more continuous reaction vessels; and
(4) optionally in the presence of a base or solvent.

2. The method of claim 1 wherein the sulfonyl chloride is of Formula 4

wherein $R^8$ is $C_1$-$C_4$ alkyl, $C_1$-$C_2$ haloalkyl, or phenyl optionally substituted with 1 to 3 substituents selected from the group consisting of halogen, $C_1$-$C_3$ alkyl and nitro.

3. The method of claim 2 wherein the sulfonyl chloride is methanesulfonyl chloride.

4. The method of claim 1 wherein the carboxylic acid of Formula 2 is combined with the aniline of Formula 3 to form a mixture, and then the mixture is combined with the sulfonyl chloride.

5. The method of claim 1 further comprising a base, wherein the base is combined with the compounds of Formulae 2 and 3 to form the mixture before combining with the sulfonyl chloride.

6. The method of claim 5 wherein the base is selected from 2-picoline, 3-picoline, 2,6-lutidine and pyridine.

7. The method of claim 1 further comprising a solvent, wherein the solvent is combined with the compounds of Formulae 2 and 3 and the sulfonyl chloride.

8. The method of claim 1 wherein a compound of Formula 1 is prepared, and the compound is selected from the group consisting of:

3-bromo-N-[4-chloro-2-methyl-6-[(methylamino) carbonyl]phenyl]-1-(3-chloro-2-pyridinyl)-1H-pyrazole-5-carboxamide, 3-bromo-1-(3-chloro-2-pyridinyl)-N-[4-cyano-2-methyl-6-[(methylamino) carbonyl]phenyl]-1H-pyrazole-5-carboxamide, 1-(3-chloro-2-pyridinyl)-N-[4-cyano-2-methyl-6-[(methylamino) carbonyl]phenyl]-3-[[5-(trifluoromethyl)-2H-tetrazol-2-yl]methyl]-1H-pyrazole-5-carboxamide, and 3-bromo-N-[2-bromo-4-chloro-6-[[(1-cyclopropylethyl]amino]carbonyl]phenyl]-1-(3-chloro-2-pyridinyl)-1H-pyrazole-5-carboxamide.

9. The method of claim 1, wherein the reaction vessels are selected from the group consisting of continuous stirred tank reactors, plug flow reactors, and combinations thereof.

10. The method of claim 9, wherein the reaction zone comprises two continuous reaction vessels in series.

11. The method of claim 9, wherein the reaction zone comprises one continuous reaction vessel.

12. The method of claim 9, wherein each of the one or more reaction vessels in the reaction zone is operated at an independent residence time and temperature.

13. The method of claim 9, wherein an average residence time for moieties in each reaction vessel in the reaction zone is 2 hours or less.

14. The method of claim 9, wherein the isolation step comprises:
quenching a reaction mass comprising the compound of Formula 1 obtained from the reaction zone in a quench zone to precipitate the compound of Formula 1; and
separating the compound of Formula 1 from the quenched reaction mass by filtration to form collected solid compound of Formula 1.

15. The method of claim 14, wherein quenching the reaction mass comprises continuously adding an antisolvent to the reaction mass in the quench zone.

16. The method of claim 14, wherein the quench zone consists of one or more continuous quench vessels.

17. The method of claim 9, wherein the isolation step yields a filtrate, and wherein the filtrate is recycled back into the reaction zone.

18. The method of claim 1, wherein the molar ratio of the compound of Formula 2 to the compound of Formula 3 is from about 1.2:1 to about 1:1.2.

19. The method of claim 1, wherein the carboxylic acid compound of Formula 2, the aniline compound of Formula 3 and sulfonyl chloride are combined at a temperature between about −70 and about 100° C.

* * * * *